US012723241B2

(12) United States Patent
Chatterjee et al.

(10) Patent No.: US 12,723,241 B2
(45) Date of Patent: Sep. 1, 2026

(54) CHIMERIC THERMOSTABLE AMINOACYL-tRNA SYNTHETASE FOR ENHANCED UNNATURAL AMINO ACID INCORPORATION

(71) Applicant: Trustees of Boston College, Chestnut Hill, MA (US)

(72) Inventors: Abhishek Chatterjee, Lexington, MA (US); Katherine Grasso, Boston, MA (US)

(73) Assignee: Trustees of Boston College

( * ) Notice: Subject to any disclaimer, the term of this patent is extended or adjusted under 35 U.S.C. 154(b) by 943 days.

(21) Appl. No.: 17/768,408

(22) PCT Filed: Oct. 15, 2020

(86) PCT No.: PCT/US2020/055834
§ 371 (c)(1),
(2) Date: Apr. 12, 2022

(87) PCT Pub. No.: WO2021/076795
PCT Pub. Date: Apr. 22, 2021

(65) Prior Publication Data

US 2023/0279378 A1 Sep. 7, 2023

Related U.S. Application Data

(60) Provisional application No. 62/973,599, filed on Oct. 15, 2019.

(51) Int. Cl.
*C12N 9/00* (2006.01)
*C12N 1/205* (2026.01)
*C12N 15/70* (2006.01)

(52) U.S. Cl.
CPC ............... *C12N 9/93* (2013.01); *C12N 1/205* (2021.05); *C12N 15/70* (2013.01); *C12Y 601/01* (2013.01)

(58) Field of Classification Search
None
See application file for complete search history.

(56) References Cited

U.S. PATENT DOCUMENTS

| | | | | |
|---|---|---|---|---|
| 6,255,090 | B1 * | 7/2001 | Famodu ............. | C12N 15/8274 800/278 |
| 8,207,316 | B1 * | 6/2012 | Bentwich ........... | C12N 15/1131 435/375 |
| 10,717,975 | B2 | 7/2020 | Chatterjee et al. | |
| 10,781,437 | B2 * | 9/2020 | First ........................ | C12P 21/00 |
| 2025/0027130 | A1 * | 1/2025 | Shrader ................... | C12P 19/34 |
| 2025/0043267 | A1 * | 2/2025 | Chatterjee ............ | C12Y 601/01 |

FOREIGN PATENT DOCUMENTS

| | | |
|---|---|---|
| JP | 2004537984 | 12/2004 |
| JP | 2007514447 | 6/2007 |
| JP | 2007525943 | 9/2007 |
| JP | 2022537960 | 8/2022 |
| JP | 2022551483 | 12/2022 |
| WO | WO 2002086075 A2 | 10/2002 |
| WO | WO 2004094593 A2 | 11/2004 |
| WO | WO2020257668 | 12/2020 |

OTHER PUBLICATIONS

Park et al. (PNAS, 2008, vol. 105, No. 32, pp. 11043-11049).*
Brick, P., et al., "Structure of tyrosyl-tRNA synthetase refined at 2.3 A resolution. Interaction of the enzyme with the tyrosyl adenylate intermediate," J. Mol. Biol., 208(1): 83-98 (1989).
Chatterjee, A., et al., "A Tryptophanyl-tRNA Synthetase/tRNA Pair for Unnatural Amino Acid Mutagenesis in *E. coli*," Angewandte Chemie International Edition 52(19): 5106-5109 (2013).
Chin, J. W., "Expanding and reprogramming the genetic code," Nature 550(7674): 53-60 (2017).
Chin, J. W., et al., "An expanded eukaryotic genetic code," Science, 301(5635): 964-967 (2003).
Guez-Ivanier, V., et al., "Mapping the stability determinants of bacterial tyrosyl transfer RNA synthetases by an experimental evolutionary approach," Journal of molecular biology 234(1): 209-221 (1993).
Hino, N., et al., "Protein photo-cross-linking in mammalian cells by site-specific incorporation of a photoreactive amino acid," Nature methods 2(3): 201-206 (2005).
Italia, J. S., et al. "An orthogonalized platform for genetic code expansion in both bacteria and eukaryotes," Nature chemical biology 13(4): 446-450 (2017).
Italia, J., et al., "Expanding the genetic code of mammalian cells," Biochemical Society transactions, 45(2): 555-562 (2017).
Molina, D.M., et al., "The cellular thermal shift assay: a novel biophysical assay for in situ drug target engagement and mechanistic biomarker studies," Annual review of pharmacology and toxicology, 56: 141-161 (2016).
Molina, D.M., et al., "Monitoring drug target engagement in cells and tissues using the cellular thermal shift assay," Science (New York, NY) 341(6141): 84-87 (2013).
Meyer, A.J., et al., "Library Generation by Gene Shuffling," Curr Protoc Mol Biol., 105, Unit-15.12 (2015).
Sakurama, H., et al., "Two crystal structures of lysyl-tRNA synthetase from Bacillus stearothermophilus in complex with lysyladenylate-like compounds: insights into the irreversible formation of the enzyme-bound adenylate of L-lysine hydroxamate," Journal of biochemistry, 145(5): 555-563 (2009).

(Continued)

*Primary Examiner* — Hope A Robinson
(74) *Attorney, Agent, or Firm* — HoustonHogle LLP

(57) ABSTRACT

The present invention describes methods to create chimeric aminoacyl-tRNA synthetases (aaRS) derived from bacteria which show optimal activity and high thermostability. These chimeric aaRSs can be more aggressively engineered to generate a wider assortment of Uaa-selective mutants that are stable at the physiological temperature. The invention further describes the composition of chimeric TyrRSs, generated from *E. coli* and *G. stearothermophilus* TyrRSs, which demonstrate enhanced stability relative to EcTyrRS and higher activity relative to both TyrRS enzymes.

8 Claims, 29 Drawing Sheets

Specification includes a Sequence Listing.

(56) References Cited

OTHER PUBLICATIONS

Tokuriki, N., et al., "Protein dynamism and evolvability," Science, 324(5924): 203-207 (2009).
Tokuriki, N., et al., "Stability effects of mutations and protein evolvability," Current opinion in structural biology, 19(5): 596-604 (2009).
Trudeau, D. L., et al., "Protein engineers turned evolutionists-the quest for the optimal starting point," Current opinion in biotechnology, 60: 46-52 (2019).
Wilkins, B. J., et al., "A cascade of histone modifications induces chromatin condensation in mitosis," Science, 343(6166): 77-80 (2014).
Wolf-Watz, M., et al., Linkage between dynamics and catalysis in a thermophilic-mesophilic enzyme pair, Nature structural & molecular biology, 11(10): 945-949 (2004).
Wu, N., et al., "A genetically encoded photocaged amino acid," Journal of the American Chemical Society, 126(44): 14306-14307 (2004).
Zhao, H., et al., "In vitro 'sexual' evolution through the PCR-based staggered extension process (StEP)," Nature Protocols, 1(4): 1865-1871 (2006).
Zheng, Y., et al., "Virus-Enabled Optimization and Delivery of the Genetic Machinery for Efficient Unnatural Amino Acid Mutagenesis in Mammalian Cells and Tissues," ACS synthetic biology, 6(1): 13-18 (2017).
International Preliminary Report on Patentability mailed on Apr. 28, 2022, from International Application No. PCT/US2020/055834, filed on Oct. 15, 2020. 9 pages.
International Search Report and Written Opinion of the International Searching Authority, mailed on Feb. 15, 2021, from International Application No. PCT/US2020/055834, filed on Oct. 15, 2020. 16 pages.
Chatterjee, A., et al., "Efficient viral delivery system for unnatural amino acid mutagenesis in mammalian cells," Proceedings of the National Academy of Sciences of the United States of America 110(29): 11803-11808 (2013).
Chin, J. W., et al., "Addition of a photocrosslinking amino acid to the genetic code of *Escherichia coli*," Proceedings of the National Academy of Sciences, 99(17): 11020-11024 (2002).
Dugan, A., et al., "Discovery of Enzymatic Targets of Transcriptional Activators via in Vivo Covalent Chemical Capture," Journal of the American Chemical Society, 138(38): 12629-12635 (2016).
Dumas, A., et al., "Designing logical codon reassignment—Expanding the chemistry in biology," Chemical Science 6(1): 50-69 (2015).
Italia, J.S., et al., "Resurrecting the bacterial tyrosy1-tRNA Synthetase/tRNA pair for expanding the genetic code of both *E. coli* and eukaryotes," Cell Chemical Biology, 25(10): 1304-1312. e1305 (2018).
Jermutus, L., et al., "Structure-based chimeric enzymes as an alternative to directed enzyme evolution: phytase as a test case," Journal of Biotechnology, 85: 15-24 (2001).
Krishnamurthy, M., et al., "Caught in the act: Covalent cross-linking captures activator—coactivator interactions in vivo," ACS Chemical Biology, 6(12): 1321-1326 (2011).
Laowanapiban, P., et al., "Independent saturation of three TrpRS subsites generates a partially assembled state similar to those observed in molecular simulations," Proceedings of the National Academy of Sciences of the United States of America, 106(6): 1790-1795 (2009).
Li, Y., et al., "A diverse family of thermostable cytochrome P450s created by recombination of stabilizing fragments," Nature biotechnology 25, 1051-1056 (2007).
Mukai, T., et al., "Rewriting the genetic code," Annual review of microbiology 71, 557-577 (2017).
Sakamoto, K., et al., "Site-specific incorporation of an unnatural amino acid into proteins in mammalian cells," Nucleic acids research, 30(21): 4692-4699 (2002).
Socha, R. D., et al., "Modulating protein stability-directed evolution strategies for improved protein function," The FEBS journal, 280(22): 5582-5595 (2013).
Vargas-Rodriguez, O., et al., "Upgrading aminoacyl-tRNA synthetases for genetic code expansion," Current Opinion in Chemical Biology, 46: 115-122 (2018).
Wang, Q., et al., "Expanding the Genetic Code for Biological Studies," Chemistry and Biology, 16(3): 323-336 (2009).
Wrenbeck, E.E., et al., "An Automated Data-Driven Pipeline for Improving Heterologous Enzyme Expression," ACS Synth. Biol., 8(3): 474-481 (2019).
Young, D. D., et al., "An evolved aminoacyl-tRNA synthetase with atypical polysubstrate specificity," Biochemistry, 50(11): 1894-1900 (2011).
Young, D. D., et al., "Playing with the molecules of life," ACS chemical biology, 13(4): 854-870 (2018).
Zheng, Y., et al., "Defining the current scope and limitations of dual noncanonical amino acid mutagenesis in mammalian cells," Chem Sci, 8(10): 7211-7217 (2017).
Zheng, Y., et al., "Expanding the scope of single-and double-noncanonical amino acid mutagenesis in mammalian cells using orthogonal polyspecific leucyl-tRNA synthetases," Biochemistry, 57(4): 441-445 (2018).
Examiner requisition received for Canadian Patent Application No. 3,154,273 mailed on Feb. 28, 2024, 6 Pages.
Notice of Reasons for Refusal received for Japanese Patent Application No. 2022-520264 mailed on Oct. 1, 2024, 16 Pages.

* cited by examiner

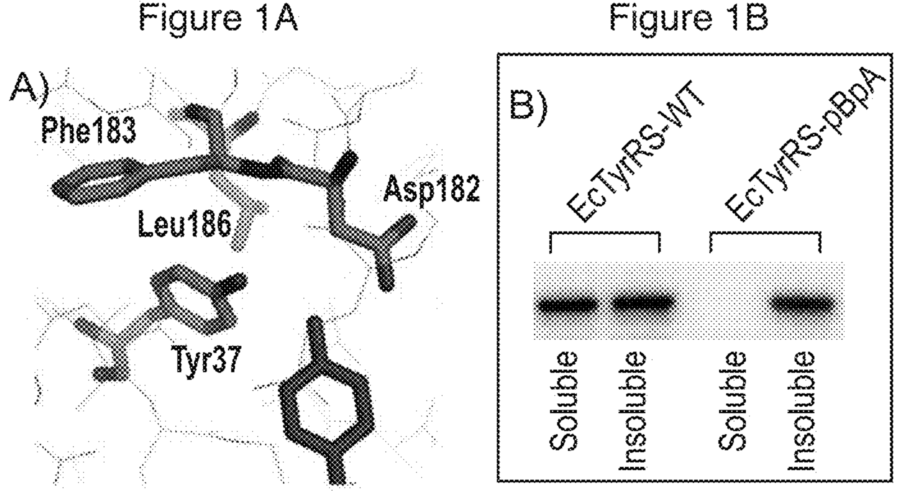
| | Tyr37 | Asp182 | Phe183 | Leu186 |
|---|---|---|---|---|
| **EcTyrRS-pBpA** | Gly | Gly | Phe | Ala |
| **EcTyrRS-Poly** | Val | Ser | Met | Ala |
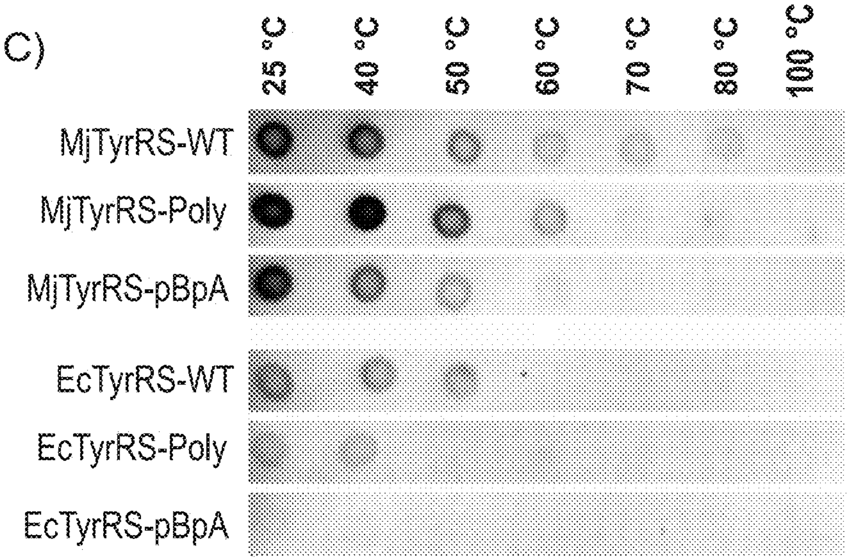
Figure 1C ChTyrRS-H2 sequence:

atgGCAAGCAGTAACTTGATTAAACAATTGCAAGAGCGGGGGCTGGTAGCCCAGGTGACGGACGAGGAAGCGT
TAGCAGAGCGACTGGCGCAAGGCCCGATCGCGCTCTATTGCGGCTTCGATCCTACCGCTGACAGCTTGCATTT
GGGGCATCTTGTTCCATTGTTATGCCTGAAACGCTTCCAGCAGGCGGGTCACCGTCCGATCGCGCTGGTTGGT
GGTGCGACCGGTCTGATTGGCGACCCGAGCGGCAAGAAAAGCGAGCGTACCCTGAACGCGAAGGAAACCGTTG
AAGCGTGGAGCGCGCGTATCAAAGAACAGCTGGGTCGTTTCCTGGACTTTGAGGCGGATGGCAACCCGGCGAA
GATTAAAAACAACTATGACTGGATCGGTCCGCTGGATGTGATTACCTTCCTGCGTGATGTGGGCAAGCACTTT
AGCGTTAACTACATGATGGCGAAAGAGAGCGTTCAGAGCCGTATCGAAACCGGTATTAGCTTCACCGAGTTTA
GCTACATGATGCTGCAAGCGTATGATTTCCTGCGTCTGTACGAAACCGAAGGCTGCCGTCTGCAGATCGGTGG
CAGCGATCAATGGGGTAACATCACCGCGGGCCTGGAACTGATTCGTAAGACCAAAGGTGAAGCGCGTGCGTTT
GGCCTGACCATCCCGCTGGTGACCAAGGCGGACGGTACCAAGTTTGGCAAAACCGAAAGCGGTACCATTTGGC
TGGATAAGGAGAAAACCAGCCCGTACGAATTCTATCAGTTTTGGATCAACACCGACGATCGTGACGTTATTCG
TTACCTGAAGTATTTCACCTTTCTGAGCAAAGAGGAAATCGAAGCGCTGGAGCAGGAACTGCGTGAGGCGCCG
GAAAAGCGTGCGGCGCAAAAAGCGCTGGCGGAGGAAGTGACCAAACTGGTTCACGGTGAGGAAGCGCTGCGTC
AGGCGATCCGTATTAGCGAAGCGCTGTTTAGCGGTGATATCGCGAACCTGACCGCGGCGGAGATTGAACAAGG
CTTCAAGGACGTGCCGAGCTTTGTTCACGAAGGTGGCGATGTGCCGCTGGTTGAGCTGCTGGTTAGCGCGGGT
ATCAGCCCGAGCAAACGTCAGGCGCGTGAAGACATCCAAAACGGTGCGATTTACGTGAACGGCGAGCGTCTGC
AAGATGTTGGCGCGATTCTGACCGCGGAACACCGTCTGGAAGGTCGTTTTACCGTTATCCGTCGTGGCAAGAA
GAAATACTATCTGATTCGTTATGCGTAA ChTyrRS-H6 sequence:

atgGCAAGCAGTAACTTGATTAAACAATTGCAAGAGCGGGGGCTGGTAGCCCAGGTGACGGACGAGGAAGCG
TTAGCAGAGCGACTGGCGCAAGGCCCGATCGCGCTCTATTGCGGCTTCGATCCTACCGCTGACAGCTTGCAT
TTGGGGCATCTTGTTCCATTGTTATGCCTGAAACGCTTCCAGCAGGCGGGCCACAAGCCGGTTGCGCTGGTA
GGCGGCGCGACGGGTCTGATTGGCGACCCGAGTTTCAAAGCTGCCGAGCGTAAGCTGAACACCGAAGAAACT
GTTCAGGAGTGGGTGGACAAAATCCGTAAGCAGGTTGCCCCGTTCCTCGATTTCGACTGTGGAGAAAACTCT
GCTATCGCGGCGAACAACTATGACTGGTTCGGCAATATGAATGTGCTGACCTTCCTGCGCGATATTGGCAAA
CACTTCTCCGTTAACCAGATGATCAACAAAGAAGCGGTTAAGCAGCGTCTCAACCGTGAAGATCAGGGGATT
TCGTTCACTGAGTTTTCCTACAGCCTGTTGCAGGGTTATGACTTCGCCTGTCTGAACAAACAGTACGGTGTG
GTGCTGCAAATTGGTGGTTCTGACCAGTGGGGTAACATCACTTCTGGTATCGACCTGACCCGTCGTCTGCAT
CAGAATCAGGTGTTTGGCCTGACCGTTCCGCTGATCACTAAAGCAGATGGCACCAAATTTGGCAAAACCGAA
AGCGGTACCATTTGGCTGGATAAGGAGAAAACCAGCCCGTACGAATTCTATCAGTTTTGGATCAACACCGAC
GATCGTGACGTTATTCGTTACCTGAAGTATTTCACCTTTCTGAGCAAAGAGGAAATCGAAGCGCTGGAGCAG
GAACTGCGTGAGGCGCCGGAAAAGCGTGCGGCGCAAAAAGCGCTGGCGGAGGAAGTGACCAAACTGGTTCAC
GGTGAGGAAGCGCTGCGTCAGGCGATCCGTATTAGCGAAGCGCTGTTTAGCGGTGATATCGCGAACCTGACC
GCGGCGGAGATTGAACAAGGCTTCAAGGACGTGCCGAGCTTTGTTCACGAAGGTGGCGATGTGCCGCTGGTT
GAGCTGCTGGTTAGCGCGGGTATCAGCCCGAGCAAACGTCAGGCGCGTGAAGACATCCAAAACGGTGCGATT
TACGTGAACGGCGAGCGTCTGCAAGATGTTGGCGCGATTCTGACCGCGGAACACCGTCTGGAAGGTCGTTTT
ACCGTTATCCGTCGTGGCAAGAAGAAATACTATCTGATTCGTTATGCGTAA

Figure 5

| | Tyr32 | Leu65 | Glu107 | Phe108 | Gln109 | Asp158 | Ile159 |
|---|---|---|---|---|---|---|---|
| MjTyrRS-pBpA | Gly | Leu | Pro | Phe | Gln | Thr | Ser |
| MjTyrRS-Poly | Leu | Val | Glu | Trp | Met | Gly | Ala |

pBK MCS GsYRS wt

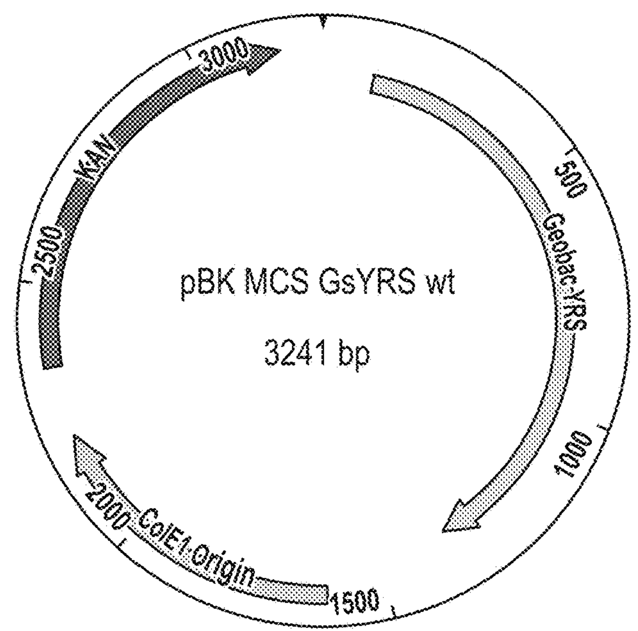

cttttgctgagttgaaggatccgcggccgctcgggttgtcagcctgtcccgcttataagatcatacgccgttatacgttgtttacgctttga
ggaatcccatatgATGGACCTGCTGGCGGAACTGCAATGGCGTGGCCTGGTTAATCAGA
CCACCGACGAAGATGGCCTGCGTAAACTGCTGAACGAGGAACGTGTGACCCTGT
ATTGCGGTTTCGACCCGACCGCGGATAGCCTGCACATCGGCAACCTGGCGGCGA
TTCTGACCCTGCGTCGTTTTCAGCAAGCGGGTCACCGTCCGATCGCGCTGGTTGG
TGGTGCGACCGGTCTGATTGGCGACCCGAGCGGCAAGAAAAGCGAGCGTACCCT
GAACGCGAAGGAAACCGTTGAAGCGTGGAGCGCGCGTATCAAAGAACAGCTGG
GTCGTTTCCTGGACTTTGAGGCGGATGGCAACCCGGCGAAGATTAAAAACAACT
ATGACTGGATCGGTCCGCTGGATGTGATTACCTTCCTGCGTGATGTGGGCAAGCA
CTTTAGCGTTAACTACATGATGGCGAAAGAGAGCGTTCAGAGCCGTATCGAAAC
CGGTATTAGCTTCACCGAGTTTAGCTACATGATGCTGCAAGCGTATGACTTCCTG
CGTCTGTACGAAACCGAAGGCTGCCGTCTGCAGATCGGTGGCAGCGATCAATGG
GGTAACATCACCGCGGGCCTGGAACTGATTCGTAAGACCAAAGGTGAAGCGCGT
GCGTTTGGCCTGACCATCCCGCTGGTGACCAAGGCGGACGGTACCAAGTTTGGCA
AAACCGAAAGCGGTACCATTTGGCTGGATAAGGAGAAAACCAGCCCGTACGAAT
TCTATCAGTTTTGGATCAACACCGACGATCGTGACGTTATTCGTTACCTGAAGTA
TTTCACCTTTCTGAGCAAAGAGGAAATCGAAGCGCTGGAGCAGGAACTGCGTGA
GGCGCCGGAAAAGCGTGCGGCGCAAAAAGCGCTGGCGGAGGAAGTGACCAAAC
TGGTTCACGGTGAGGAAGCGCTGCGTCAGGCGATCCGTATTAGCGAAGCGCTGTT
TAGCGGTGATATCGCGAACCTGACCGCGGCGGAGATTGAACAAGGCTTCAAGGA
CGTGCCGAGCTTTGTTCACGAAGGTGGCGATGTGCCGCTGGTTGAGCTGCTGGTT
AGCGCGGGTATCAGCCCGAGCAAACGTCAGGCGCGTGAAGACATCCAAAACGGT
GCGATTTACGTGAACGGCGAGCGTCTGCAAGATGTTGGCGCGATTCTGACCGCG
GAACACCGTCTGGAAGGTCGTTTTACCGTTATCCGTCGTGGCAAGAAGAAATACT
ATCTGATTCGTTATGCGTAAggtaccatggctgcagtttcaaacgctaaattgcctgatgcgctacgcttatcaggcc

Figure 12 tacatgatctctgcaatatattgagtttgcgtgcttttgtaggccggataaggcgttcacgccgcatccggcaagaaacagcaaacaatc
caaaacgccgcgttcagcggcgtttttctgctttcttcgcgaattaattccgcttcgcacatgtgagcaaaaggccagcaaaaggcca
ggaaccgtaaaaaggccgcgttgctggcgtttttccataggctccgcccccctgacgagcatcacaaaaatcgacgctcaagtcaga
ggtggcgaaacccgacaggactataaagataccaggcgtttccccctggaagctccctcgtgcgctctcctgttccgaccctgccgctt
accggatacctgtccgcctttctcccttcgggaagcgtggcgctttctcatagctcacgctgtaggtatctcagttcggtgtaggtcgttcg
ctccaagctgggctgtgtgcacgaaccccccgttcagcccgaccgctgcgccttatccggtaactatcgtcttgagtccaacccggtaa
gacacgacttatcgccactggcagcagccactggtaacaggattagcagagcgaggtatgtaggcggtgctacagagttcttgaagt
ggtggcctaactacggctacactagaaggacagtatttggtatctgcgctctgctgaagccagttaccttcggaaaaagagttggtagct
cttgatccggcaaacaaaccaccgctggtagcggtggtttttttgtttgcaagcagcagattacgcgcagaaaaaaaggatctcaagaa
gatcctttgatcttttctacggggtctgacgctcagtggaacgaaaactcacgttaagggattttggtcatgaacaataaaactgtctgctt
acataaacagtaatacaaggggtgttatgagccatattcaacgggaaacgtcttgctcgaggccgcgattaaattccaacatggatgct
gatttatatgggtataaatgggctcgcgataatgtcgggcaatcaggtgcgacaatctatcgattgtatgggaagcccgatgcgccaga
gttgtttctgaaacatggcaaaggtagcgttgccaatgatgttacagatgagatggtcagactaaactggctgacggaatttatgcctctt
ccgaccatcaagcattttatccgtactcctgatgatgcatggttactcaccactgcgatccccgggaaaacagcattccaggtattagaa
gaatatcctgattcaggtgaaaatattgttgatgcgctggcagtgttcctgcgccggttgcattcgattcctgtttgtaattgtccttttaaca
gcgatcgcgtatttcgtctcgctcaggcgcaatcacgaatgaataacggtttggttgatgcgagtgattttgatgacgagcgtaatggct
ggcctgttgaacaagtctggaaagaaatgcataagcttttgccattctcaccggattcagtcgtcactcatggtgatttctcacttgataac
cttatttttgacgaggggaaattaataggttgtattgatgttggacgagtcggaatcgcagaccgataccaggatcttgccatcctatgga
actgcctcggtgagttttctccttcattacagaaacggctttttcaaaaatatggtattgataatcctgatatgaataaattgcagtttcatttga
tgctcgatgagtttttctaatcagaattggttaattggttgtaacactggcagagcattacgctgacttgacgggacggcggctttgttgaat
aaatcgaa pBK MCS Gs-BPA-RS
Same as above but with the following active site mutations:
Y34G, D176G, L180A pBK MCS Chimera H2-YRS
Same as above but with the following aaRS sequence:
atgGCAAGCAGTAACTTGATTAAACAATTGCAAGAGCGGGGGCTGGTAGCCCAGG
TGACGGACGAGGAAGCGTTAGCAGAGCGACTGGCGCAAGGCCCGATCGCGCTCT
ATTGCGGCTTCGATCCTACCGCTGACAGCTTGCATTTGGGGCATCTTGTTCCATTG
TTATGCCTGAAACGCTTCCAGCAGGCGGGTCACCGTCCGATCGCGCTGGTTGGTG
GTGCGACCGGTCTGATTGGCGACCCGAGCGGCAAGAAAAGCGAGCGTACCCTGA
ACGCGAAGGAAACCGTTGAAGCGTGGAGCGCGCGTATCAAAGAACAGCTGGGTC
GTTTCCTGGACTTTGAGGCGGATGGCAACCCGGCGAAGATTAAAAACAACTATG
ACTGGATCGGTCCGCTGGATGTGATTACCTTCCTGCGTGATGTGGGCAAGCACTT
TAGCGTTAACTACATGATGGCGAAAGAGAGCGTTCAGAGCCGTATCGAAACCGG
TATTAGCTTCACCGAGTTTAGCTACATGATGCTGCAAGCGTATGATTTCCTGCGTC
TGTACGAAACCGAAGGCTGCCGTCTGCAGATCGGTGGCAGCGATCAATGGGGTA
ACATCACCGCGGGCCTGGAACTGATTCGTAAGACCAAAGGTGAAGCGCGTGCGT
TTGGCCTGACCATCCCGCTGGTGACCAAGGCGGACGGTACCAAGTTTGGCAAAA
CCGAAAGCGGTACCATTTGGCTGGATAAGGAGAAAACCAGCCCGTACGAATTCT
ATCAGTTTTGGATCAACACCGACGATCGTGACGTTATTCGTTACCTGAAGTATTT
CACCTTTCTGAGCAAAGAGGAAATCGAAGCGCTGGAGCAGGAACTGCGTGAGGC
GCCGGAAAAGCGTGCGGCGCAAAAAGCGCTGGCGGAGGAAGTGACCAAACTGG

Figure 12 continued

TTCACGGTGAGGAAGCGCTGCGTCAGGCGATCCGTATTAGCGAAGCGCTGTTTAG
CGGTGATATCGCGAACCTGACCGCGGCGGAGATTGAACAAGGCTTCAAGGACGT
GCCGAGCTTTGTTCACGAAGGTGGCGATGTGCCGCTGGTTGAGCTGCTGGTTAGC
GCGGGTATCAGCCCGAGCAAACGTCAGGCGCGTGAAGACATCCAAAACGGTGCG
ATTTACGTGAACGGCGAGCGTCTGCAAGATGTTGGCGCGATTCTGACCGCGGAA
CACCGTCTGGAAGGTCGTTTTACCGTTATCCGTCGTGGCAAGAAGAAATACTATC
TGATTCGTTATGCGTAA pBK MCS Chimera H2-BPA-RS
Same as Chimera H2-YRS but with the following active site mutations:
Y37G, D179G, L183A pBK MCS Chimera H6-YRS
Same as above but with the following aaRS sequence:
atgGCAAGCAGTAACTTGATTAAACAATTGCAAGAGCGGGGGCTGGTAGCCCAGG
TGACGGACGAGGAAGCGTTAGCAGAGCGACTGGCGCAAGGCCCGATCGCGCTCT
ATTGCGGCTTCGATCCTACCGCTGACAGCTTGCATTTGGGGCATCTTGTTCCATTG
TTATGCCTGAAACGCTTCCAGCAGGCGGGCCACAAGCCGGTTGCGCTGGTAGGC
GGCGCGACGGGTCTGATTGGCGACCCGAGTTTCAAAGCTGCCGAGCGTAAGCTG
AACACCGAAGAAACTGTTCAGGAGTGGGTGGACAAAATCCGTAAGCAGGTTGCC
CCGTTCCTCGATTTCGACTGTGGAGAAAACTCTGCTATCGCGGCGAACAACTATG
ACTGGTTCGGCAATATGAATGTGCTGACCTTCCTGCGCGATATTGGCAAACACTT
CTCCGTTAACCAGATGATCAACAAAGAAGCGGTTAAGCAGCGTCTCAACCGTGA
AGATCAGGGGATTTCGTTCACTGAGTTTTCCTACAGCCTGTTGCAGGGTTATGAC
TTCGCCTGTCTGAACAAACAGTACGGTGTGGTGCTGCAAATTGGTGGTTCTGACC
AGTGGGGTAACATCACTTCTGGTATCGACCTGACCCGTCGTCTGCATCAGAATCA
GGTGTTTGGCCTGACCGTTCCGCTGATCACTAAAGCAGATGGCACCAAATTTGGC
AAAACCGAAAGCGGTACCATTTGGCTGGATAAGGAGAAAACCAGCCCGTACGAA
TTCTATCAGTTTTGGATCAACACCGACGATCGTGACGTTATTCGTTACCTGAAGT
ATTTCACCTTTCTGAGCAAAGAGGAAATCGAAGCGCTGGAGCAGGAACTGCGTG
AGGCGCCGGAAAAGCGTGCGGCGCAAAAAGCGCTGGCGGAGGAAGTGACCAAA
CTGGTTCACGGTGAGGAAGCGCTGCGTCAGGCGATCCGTATTAGCGAAGCGCTG
TTTAGCGGTGATATCGCGAACCTGACCGCGGCGGAGATTGAACAAGGCTTCAAG
GACGTGCCGAGCTTTGTTCACGAAGGTGGCGATGTGCCGCTGGTTGAGCTGCTGG
TTAGCGCGGGTATCAGCCCGAGCAAACGTCAGGCGCGTGAAGACATCCAAAACG
GTGCGATTTACGTGAACGGCGAGCGTCTGCAAGATGTTGGCGCGATTCTGACCGC
GGAACACCGTCTGGAAGGTCGTTTTACCGTTATCCGTCGTGGCAAGAAGAAATAC
TATCTGATTCGTTATGCGTAA pBK MCS Chimera H6-BPA-RS
Same as Chimera H6-YRS but with the following active site mutations:
Y37G, D182G, L186A

Figure 12 continued pET22b 10X N-term His GsYRS

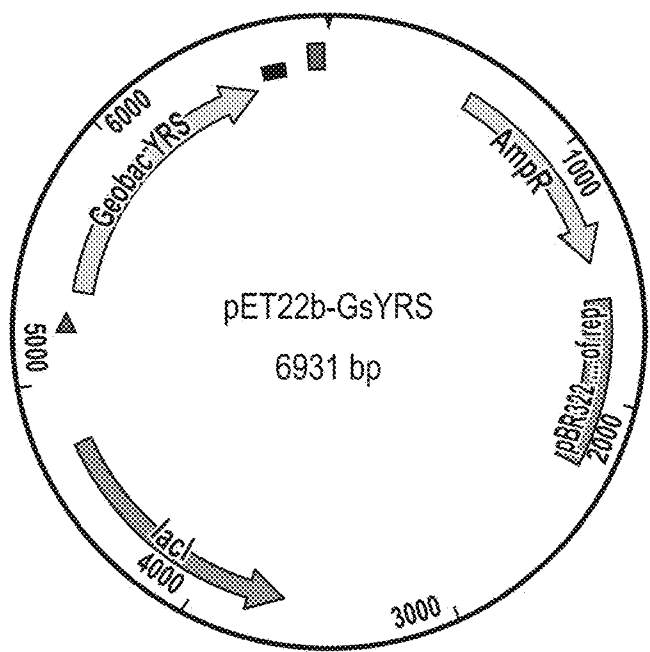

tggcgaatgggacgcgccctgtagcggcgcattaagcgcggcgggtgtggtggttacgcgcagcgtgaccgctacacttgccagcg
ccctagcgcccgctcctttcgctttcttcccttcctttctcgccacgttcgccggctttccccgtcaagctctaaatcgggggctccctttag
ggttccgatttagtgctttacggcacctcgaccccaaaaaacttgattagggtgatggttcacgtagtgggccatcgccctgatagacgg
tttttcgccctttgacgttggagtccacgttctttaatagtggactcttgttccaaactggaacaacactcaaccctatctcggtctattcttttg
atttataagggattttgccgatttcggcctattggttaaaaaatgagctgatttaacaaaaatttaacgcgaattttaacaaaatattaacgttt
acaatttcaggtggcacttttcggggaaatgtgcgcggaacccctatttgtttatttttctaaatacattcaaatatgtatccgctcatgagac
aataaccctgataaatgcttcaataatattgaaaaaggaagagtatgagtattcaacatttccgtgtcgcccttattcccttttttgcggcattt
tgccttcctgtttttgctcacccagaaacgctggtgaaagtaaaagatgctgaagatcagttgggtgcacgagtgggttacatcgaactg
gatctcaacagcggtaagatccttgagagttttcgccccgaagaacgttttccaatgatgagcacttttaaagttctgctatgtggcgcgg
tattatcccgtattgacgccgggcaagagcaactcggtcgccgcatacactattctcagaatgacttggttgagtactcaccagtcacag
aaaagcatcttacggatggcatgacagtaagagaattatgcagtgctgccataaccatgagtgataacactgcggccaacttacttctga
caacgatcggaggaccgaaggagctaaccgcttttttgcacaacatgggggatcatgtaactcgccttgatcgttgggaaccggagct
gaatgaagccataccaaacgacgagcgtgacaccacgatgcctgcagcaatggcaacaacgttgcgcaaactattaactggcgaact
acttactctagcttcccggcaacaattaatagactggatggaggcggataaagttgcaggaccacttctgcgctcggcccttccggctg
gctggtttattgctgataaatctggagccggtgagcgtgggtctcgcggtatcattgcagcactggggccagatggtaagccctcccgt
atcgtagttatctacacgacggggagtcaggcaactatggatgaacgaaatagacagatcgctgagataggtgcctcactgattaagc
attggtaactgtcagaccaagtttactcatatatactttagattgatttaaaacttcatttttaatttaaaaggatctaggtgaagatcctttttga
taatctcatgaccaaaatcccttaacgtgagttttcgttccactgagcgtcagaccccgtagaaaagatcaaaggatcttcttgagatcct
ttttttctgcgcgtaatctgctgcttgcaaacaaaaaaaccaccgctaccagcggtggtttgtttgccggatcaagagctaccaactctttt
ccgaaggtaactggcttcagcagagcgcagataccaaatactgtccttctagtgtagccgtagttaggccaccacttcaagaactctgta
gcaccgcctacatacctcgctctgctaatcctgttaccagtggctgctgccagtggcgataagtcgtgtcttaccgggttggactcaaga
cgatagttaccggataaggcgcagcggtcgggctgaacggggggttcgtgcacacagcccagcttggagcgaacgacctacaccg
aactgagatacctacagcgtgagctatgagaaagcgccacgcttcccgaagggagaaaggcggacaggtatccggtaagcggcag
ggtcggaacaggagagcgcacgagggagcttccagggggaaacgcctggtatctttatagtcctgtcgggtttcgccacctctgactt
gagcgtcgatttttgtgatgctcgtcaggggggcggagcctatggaaaaacgccagcaacgcggcctttttacggttcctggcctttgc

Figure 13 tggcctttgctcacatgttctttcctgcgttatcccctgattctgtggataaccgtattaccgcctttgagtgagctgataccgctcgccgca
gccgaacgaccgagcgcagcgagtcagtgagcgaggaagcggaagagcgcctgatgcggtattttctccttacgcatctgtgcggt
atttcacaccgcatatatggtgcactctcagtacaatctgctctgatgccgcatagttaagccagtatacactccgctatcgctacgtgact
gggtcatggctgcgccccgacacccgccaacacccgctgacgcgccctgacgggcttgtctgctcccggcatccgcttacagacaa
gctgtgaccgtctccgggagctgcatgtgtcagaggttttcaccgtcatcaccgaaacgcgcgaggcagctgcggtaaagctcatcag
cgtggtcgtgaagcgattcacagatgtctgcctgttcatccgcgtccagctcgttgagtttctccagaagcgttaatgtctggcttctgata
aagcgggccatgttaagggcggttttttcctgtttggtcactgatgcctccgtgtaagggggatttctgttcatgggggtaatgataccgat
gaaacgagagaggatgctcacgatacgggttactgatgatgaacatgcccggttactggaacgttgtgagggtaaacaactggcggt
atggatgcggcgggaccagagaaaaatcactcagggtcaatgccagcgcttcgttaatacagatgtaggtgttccacagggtagcca
gcagcatcctgcgatgcagatccggaacataatggtgcagggcgctgacttccgcgtttccagactttacgaaacacggaaaccgaa
gaccattcatgttgttgctcaggtcgcagacgttttgcagcagcagtcgcttcacgttcgctcgcgtatcggtgattcattctgctaaccag
taaggcaaccccgccagcctagccgggtcctcaacgacaggagcacgatcatgcgcacccgtggggccgccatgccggcgataat
ggcctgcttctcgccgaaacgtttggtggcgggaccagtgacgaaggcttgagcgagggcgtgcaagattccgaataccgcaagcg
acaggccgatcatcgtcgcgctccagcgaaagcggtcctcgccgaaaatgacccagagcgctgccggcacctgtcctacgagttgc
atgataaagaagacagtcataagtgcggcgacgatagtcatgccccgcgcccaccggaaggagctgactgggttgaaggctctcaa
gggcatcggtcgagatcccggtgcctaatgagtgagctaacttacattaattgcgttgcgcgtggtgaatgtgaaaccagtaacgttata
cgatgtcgcagagtatgccggtgtctcttatcagaccgtttcccgcgtggtgaaccaggccagccacgtttctgcgaaaacgcgggaa
aaagtggaagcggcgatggcggagctgaattacattcccaaccgcgtggcacaacaactggcgggcaaacagtcgttgctgattgg
cgttgccacctccagtctggccctgcacgcgccgtcgcaaattgtcgcggcgattaaatctcgcgccgatcaactgggtgccagcgtg
gtggtgtcgatggtagaacgaagcggcgtcgaagcctgtaaagcggcggtgcacaatcttctcgcgcaacgcgtcagtgggctgatc
attaactatccgctggatgaccaggatgccattgctgtggaagctgcctgcactaatgttccggcgttatttcttgatgtctctgaccagac
acccatcaacagtattattttctcccatgaagacggtacgcgactgggcgtggagcatctggtcgcattgggtcaccagcaaatcgcgc
tgttagcgggcccattaagttctgtctcggcgcgtctgcgtctggctggctggcataaatatctcactcgcaatcaaattcagccgatagc
ggaacgggaaggcgactggagtgccatgtccggttttcaacaaaccatgcaaatgctgaatgagggcatcgttcccactgcgatgctg
gttgccaacgatcagatggcgctgggcgcaatgcgcgccattaccgagtccgggctgcgcgttggtgcggatatctcggtagtggga
tacgacgataccgaagacagctcatgttatatcccgccgttaaccaccatcaaacaggattttcgcctgctggggcaaaccagcgtgg
accgcttgctgcaactctctcagggccaggcggtgaagggcaatcagctgttgcccgtctcactggtgaaaagaaaaaccaccctgg
cgcccaatacgcaaaccgcctctccccgcgcgttggccgattcattaatgcagctggcacgacaggtttcccgactggaaagcgggc
agtgacctgaattgactctcttccgggcgctatcatgccataccgcgaaaggttttgcgccattcgatggtgtccgggatctcgacgctct
ccttatgcgactcctgcattaggaagcagcccagtagtaggttgaggccgttgagcaccgccgccgcaaggaatggtgcatgcaag
gagatggcgcccaacagtcccccggccacggggcctgccaccatacccacgccgaaacaagcgctcatgagcccgaagtggcga
gcccgatcttccccatcggtgatgtcggcgatataggcgccagcaaccgcacctgtggcgccggtgatgccggccacgatgcgtcc
ggcgtagaggatcgagatctcgatcccgcgaaattaatacgactcactataggggaattgtgagcggataacaattcccctctagagttt
gacagcattatcatcgatctcgagaaatcataaaaaatttatttgctttgtgagcggataacaattataatagattcaattgtgagcggataa
caatttcacacagaattcattaaagaggagaaattacatatgcatcatcaccatcaccatcatcatcatcacgcaagcagtaacttgattaa
acaattgcaagagGACCTGCTGGCGGAACTGCAATGGCGTGGCCTGGTTAATCAGACCA
CCGACGAAGATGGCCTGCGTAAACTGCTGAACGAGGAACGTGTGACCCTGTATT
GCGGTTTCGACCCGACCGCGGATAGCCTGCACATCGGCAACCTGGCGGCGATTCT
GACCCTGCGTCGTTTTCAGCAAGCGGGTCACCGTCCGATCGCGCTGGTTGGTGGT
GCGACCGGTCTGATTGGCGACCCGAGCGGCAAGAAAAGCGAGCGTACCCTGAAC
GCGAAGGAAACCGTTGAAGCGTGGAGCGCGCGTATCAAAGAACAGCTGGGTCGT
TTCCTGGACTTTGAGGCGGATGGCAACCCGGCGAAGATTAAAAACAACTATGAC
TGGATCGGTCCGCTGGATGTGATTACCTTCCTGCGTGATGTGGGCAAGCACTTTA
GCGTTAACTACATGATGGCGAAAGAGAGCGTTCAGAGCCGTATCGAAACCGGTA

Figure 13 continued

TTAGCTTCACCGAGTTTAGCTACATGATGCTGCAAGCGTATGACTTCCTGCGTCT
GTACGAAACCGAAGGCTGCCGTCTGCAGATCGGTGGCAGCGATCAATGGGGTAA
CATCACCGCGGGCCTGGAACTGATTCGTAAGACCAAAGGTGAAGCGCGTGCGTT
TGGCCTGACCATCCCGCTGGTGACCAAGGCGGACGGTACCAAGTTTGGCAAAAC
CGAAAGCGGTACCATTTGGCTGGATAAGGAGAAAACCAGCCCGTACGAATTCTA
TCAGTTTTGGATCAACACCGACGATCGTGACGTTATTCGTTACCTGAAGTATTTC
ACCTTTCTGAGCAAAGAGGAAATCGAAGCGCTGGAGCAGGAACTGCGTGAGGCG
CCGGAAAAGCGTGCGGCGCAAAAAGCGCTGGCGGAGGAAGTGACCAAACTGGT
TCACGGTGAGGAAGCGCTGCGTCAGGCGATCCGTATTAGCGAAGCGCTGTTTAG
CGGTGATATCGCGAACCTGACCGCGGCGGAGATTGAACAAGGCTTCAAGGACGT
GCCGAGCTTTGTTCACGAAGGTGGCGATGTGCCGCTGGTTGAGCTGCTGGTTAGC
GCGGGTATCAGCCCGAGCAAACGTCAGGCGCGTGAAGACATCCAAAACGGTGCG
ATTTACGTGAACGGCGAGCGTCTGCAAGATGTTGGCGCGATTCTGACCGCGGAA
CACCGTCTGGAAGGTCGTTTTACCGTTATCCGTCGTGGCAAGAAGAAATACTATC
TGATTCGTTATGCGTAAaagcttaattagctgagcttggactcctgttgatagatccagtaatgacctcagaactccatct
ggatttgttcagaacgctcggttgccgccgggcgtttttattggtgagaatccaagctagcttggcggcggccgcactcgagcaccac
caccaccaccactgagatccggctgctaacaaagcccgaaaggaagctgagttggctgctgccaccgctgagcaataactagcataa
ccccttggggcctctaaacgggtcttgaggggttttttgctgaaaggaggaactatatccggat pET22b 10X N-term His Gs-BPA-RS
Same as GsYRS wt but with the following active site mutations:
Y34G, D176G, L180A pET22b 10X N-term His MjYRS wt
Same as above but with the following aaRS sequence:
gacgaatttgaaatgataaagagaaacacatctgaaattatcagcgaggaagagttaagagaggttttaaaaaaagatgaaaaatctgc
tnnnataggttttgaaccaagtggtaaaatacatttagggcattatctccaaataaaaaagatgattgatttacaaaatgctggatttgatat
aattatannntggctgatttannngcctatttaaaccagaaaggagagttggatgagattagaaaaataggagattataacagaaaagt
ttttgaagcaatggggttaaaggcaaaatatgtttatggaagtgaannnnnnncttgataaggattatacactgaatgtctatagattggctt
taaaaactaccttaaaaagagcaagaaggagtatggaacttatagcaagagaggatgaaaatccaaaggttgctgaagttatctatcca
ataatgnnngttaatnnnnnncattatnnnggcgttgatgttgcagttggagggatggagcagagaaaaatacacatgttagcaagg
gagctttaccaaaaaaggttgtttgtattcacaaccctgtcttaacgggtttggatggagaaggaaagatgagttcttcaaaagggaatt
ttatagctgttgatgactctccagaagagattagggctaagataaagaaagcatactgcccagctggagttgttgaaggaaatccaataat
ggagatagctaaatacttccttgaatatcctttaaccataaaaaggccagaaaaatttggtggagatttgacagttaatagctatgaggag
ttagagagtttatttaaaaataaggaattgcatccaatggatttaaaaaatgctgtagctgaagaacttataaagatttagagccaattaga
aagagattataa pET22b 10X N-term His Mj-CNF-RS
Same as MjYRS wt but with the following active site mutations:

Y32L, L65V, F108W, Q109M, D158G, I159A pET22b 10X N-term His EcYRS wt
Same as above but with the following aaRS sequence:
GCAAGCAGTAACTTGATTAAACAATTGCAAGAGCGGGGGCTGGTAGCCCAGGTG
ACGGACGAGGAAGCGTTAGCAGAGCGACTGGCGCAAGGCCCGATCGCGCTCTAT
TGCGGCTTCGATCCTACCGCTGACAGCTTGCATTTGGGGCATCTTGTTCCATTGTT

Figure 13 continued

ATGCCTGAAACGCTTCCAGCAGGCGGGCCACAAGCCGGTTGCGCTGGTAGGCGG
CGCGACGGGTCTGATTGGCGACCCGAGCTTCAAAGCTGCCGAGCGTAAGCTGAA
CACCGAAGAAACTGTTCAGGAGTGGGTGGACAAAATCCGTAAGCAGGTTGCCCC
GTTCCTCGATTTCGACTGTGGAGAAAACTCTGCTATCGCGGCGAACAACTATGAC
TGGTTCGGCAATATGAATGTGCTGACCTTCCTGCGCGATATTGGCAAACACTTCT
CCGTTAACCAGATGATCAACAAAGAAGCGGTTAAGCAGCGTCTCAACCGTGAAG
ATCAGGGGATTTCGTTCACTGAGTTTTCCTACAACCTGTTGCAGGGTTATGACTTC
GCaTGTCTGAACAAACAGTACGGTGTGGTGCTGCAAATTGGTGGTTCTGACCAGT
GGGGTAACATCACTTCTGGTATCGACCTGACCCGTCGTCTGCATCAGAATCAGGT
GTTTGGCCTGACCGTTCCGCTGATCACTAAAGCAGATGGCACCAAATTTGGTAAA
ACTGAAGGCGGCGCAGTCTGGTTaGATCCGAAGAAAACCAGCCCGTACAAATTCT
ACCAGTTCTGGATCAACACTGCGGACGCCGACGTTTACCGCTTCCTGAAGTTCTT
CACCTTTATGAGCATTGAAGAGATCAACGCCCTGGAAGAAGAAGATAAAAACAG
CGGTAAAGCACCGCGCGCCCAGTATGTACTGGCGGAGCAGGTGACTCGTCTGGT
TCACGGTGAAGAAGGTTTACAGGCGGCAAAACGTATTACCGAATGCCTGTTCAG
CGGTTCTTTGAGTGCGCTGAGTGAAGCGGACTTCGAACAGCTGGCGCAGGACGG
CGTACCGATGGTTGAGATGGAAAAGGGCGCAGACCTGATGCAGGCACTGGTCGA
TTCTGAACTGCAACCTTCCCGTGGTCAGGCACGTAAAACTATCGCCTCCAATGCC
ATCACCATTAACGGTGAAAAACAGTCCGATCCTGAATACTTCTTTAAAGAAGAA
GATCGTCTGTTTGGTCGTTTTACCTTACTGCGTCGCGGTAAAAAGAATTACTGTCT
GATTTGCTGGAAAtaa pET22b 10X N-term His Ec-BPA-RS
Same as EcYRS wt but with the following active site mutations:
Y37G, D182G, L186A pET22b 10X N-term His Ec-OMeYRS
Same as EcYRS wt but with the following active site mutations:
Y37V, D182S, F183M, L186A pET22b 10X N-term His Chimera H2-YRS
Same as above but with the following aaRS sequence:
GCAAGCAGTAACTTGATTAAACAATTGCAAGAGCGGGGGCTGGTAGCCCAGGTG
ACGGACGAGGAAGCGTTAGCAGAGCGACTGGCGCAAGGCCCGATCGCGCTCTAT
TGCGGCTTCGATCCTACCGCTGACAGCTTGCATTTGGGGCATCTTGTTCCATTGTT
ATGCCTGAAACGCTTCCAGCAGGCGGGTCACCGTCCGATCGCGCTGGTTGGTGGT
GCGACCGGTCTGATTGGCGACCCGAGCGGCAAGAAAAGCGAGCGTACCCTGAAC
GCGAAGGAAACCGTTGAAGCGTGGAGCGCGCGTATCAAAGAACAGCTGGGTCGT
TTCCTGGACTTTGAGGCGGATGGCAACCCGGCGAAGATTAAAAACAACTATGAC
TGGATCGGTCCGCTGGATGTGATTACCTTCCTGCGTGATGTGGGCAAGCACTTTA
GCGTTAACTACATGATGGCGAAAGAGAGCGTTCAGAGCCGTATCGAAACCGGTA
TTAGCTTCACCGAGTTTAGCTACATGATGCTGCAAGCGTATGATTTCCTGCGTCTG
TACGAAACCGAAGGCTGCCGTCTGCAGATCGGTGGCAGCGATCAATGGGGTAAC
ATCACCGCGGGCCTGGAACTGATTCGTAAGACCAAAGGTGAAGCGCGTGCGTTT
GGCCTGACCATCCCGCTGGTGACCAAGGCGGACGGTACCAAGTTTGGCAAAACC

Figure 13 continued

GAAAGCGGTACCATTTGGCTGGATAAGGAGAAAACCAGCCCGTACGAATTCTAT
CAGTTTTGGATCAACACCGACGATCGTGACGTTATTCGTTACCTGAAGTATTTCA
CCTTTCTGAGCAAAGAGGAAATCGAAGCGCTGGAGCAGGAACTGCGTGAGGCGC
CGGAAAAGCGTGCGGCGCAAAAAGCGCTGGCGGAGGAAGTGACCAAACTGGTT
CACGGTGAGGAAGCGCTGCGTCAGGCGATCCGTATTAGCGAAGCGCTGTTTAGC
GGTGATATCGCGAACCTGACCGCGGCGGAGATTGAACAAGGCTTCAAGGACGTG
CCGAGCTTTGTTCACGAAGGTGGCGATGTGCCGCTGGTTGAGCTGCTGGTTAGCG
CGGGTATCAGCCCGAGCAAACGTCAGGCGCGTGAAGACATCCAAAACGGTGCGA
TTTACGTGAACGGCGAGCGTCTGCAAGATGTTGGCGCGATTCTGACCGCGGAAC
ACCGTCTGGAAGGTCGTTTTACCGTTATCCGTCGTGGCAAGAAGAAATACTATCT
GATTCGTTATGCGTAA pET 22b 10X N-term His Chimera H2-BPA-RS
Same as H2-YRS but with the following active site mutations:
Y37G, D179G, L183A pET22b 10X N-term His Chimera H6-YRS
Same as above but with the following aaRS sequence:
GCAAGCAGTAACTTGATTAAACAATTGCAAGAGCGGGGGCTGGTAGCCCAGGTG
ACGGACGAGGAAGCGTTAGCAGAGCGACTGGCGCAAGGCCCGATCGCGCTCTAT
TGCGGCTTCGATCCTACCGCTGACAGCTTGCATTTGGGGCATCTTGTTCCATTGTT
ATGCCTGAAACGCTTCCAGCAGGCGGGCCACAAGCCGGTTGCGCTGGTAGGCGG
CGCGACGGGTCTGATTGGCGACCCGAGTTTCAAAGCTGCCGAGCGTAAGCTGAA
CACCGAAGAAACTGTTCAGGAGTGGGTGGACAAAATCCGTAAGCAGGTTGCCCC
GTTCCTCGATTTCGACTGTGGAGAAAACTCTGCTATCGCGGCGAACAACTATGAC
TGGTTCGGCAATATGAATGTGCTGACCTTCCTGCGCGATATTGGCAAACACTTCT
CCGTTAACCAGATGATCAACAAAGAAGCGGTTAAGCAGCGTCTCAACCGTGAAG
ATCAGGGGATTTCGTTCACTGAGTTTTCCTACAGCCTGTTGCAGGGTTATGACTTC
GCCTGTCTGAACAAACAGTACGGTGTGGTGCTGCAAATTGGTGGTTCTGACCAGT
GGGGTAACATCACTTCTGGTATCGACCTGACCCGTCGTCTGCATCAGAATCAGGT
GTTTGGCCTGACCGTTCCGCTGATCACTAAAGCAGATGGCACCAAATTTGGCAAA
ACCGAAAGCGGTACCATTTGGCTGGATAAGGAGAAAACCAGCCCGTACGAATTC
TATCAGTTTTGGATCAACACCGACGATCGTGACGTTATTCGTTACCTGAAGTATTT
CACCTTTCTGAGCAAAGAGGAAATCGAAGCGCTGGAGCAGGAACTGCGTGAGGC
GCCGGAAAAGCGTGCGGCGCAAAAAGCGCTGGCGGAGGAAGTGACCAAACTGG
TTCACGGTGAGGAAGCGCTGCGTCAGGCGATCCGTATTAGCGAAGCGCTGTTTAG
CGGTGATATCGCGAACCTGACCGCGGCGGAGATTGAACAAGGCTTCAAGGACGT
GCCGAGCTTTGTTCACGAAGGTGGCGATGTGCCGCTGGTTGAGCTGCTGGTTAGC
GCGGGTATCAGCCCGAGCAAACGTCAGGCGCGTGAAGACATCCAAAACGGTGCG
ATTTACGTGAACGGCGAGCGTCTGCAAGATGTTGGCGCGATTCTGACCGCGGAA
CACCGTCTGGAAGGTCGTTTTACCGTTATCCGTCGTGGCAAGAAGAAATACTATC
TGATTCGTTATGCGTAA pET22b 10X N-term His Chimera H6-BPA-RS
Same as H6-YRS but with the following active site mutations:
Y37G, D182G, L186A

Figure 13 continued pB1U Gs-BPA-RS

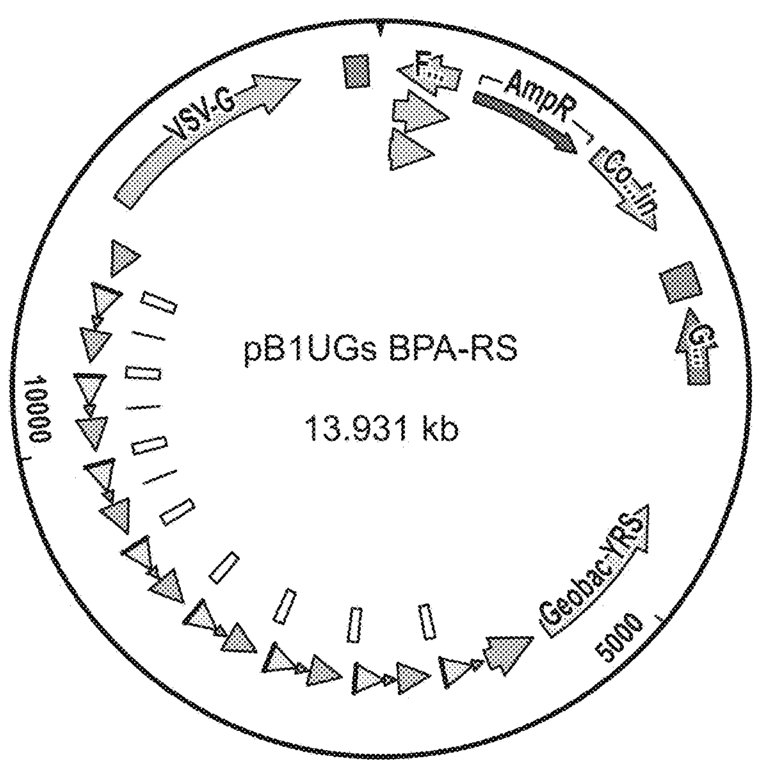

ttctctgtcacagaatgaaaatttttctgtcatctcttcgttattaatgtttgtaattgactgaatatcaacgcttatttgcagcctgaatggcga
atgggacgcgccctgtagcggcgcattaagcgcggcgggtgtggtggttacgcgcagcgtgaccgctacacttgccagcgccctag
cgcccgctcctttcgctttcttcccttcctttctcgccacgttcgccggctttccccgtcaagctctaaatcgggggctccctttagggttcc
gatttagtgctttacggcacctcgaccccaaaaaacttgattagggtgatggttcacgtagtgggccatcgccctgatagacggtttttcg
ccctttgacgttggagtccacgttctttaatagtggactcttgttccaaactggaacaacactcaaccctatctcggtctattcttttgatttat
aagggattttgccgatttcggcctattggttaaaaaatgagctgatttaacaaaaatttaacgcgaattttaacaaaatattaacgtttacaat
ttcaggtggcacttttcggggaaatgtgcgcggaacccctatttgtttatttttctaaatacattcaaatatgtatccgctcatgagacaataa
ccctgataaatgcttcaataatattgaaaaaggaagagtatgagtattcaacatttccgtgtcgcccttattcccttttttgcggcattttgcct
tcctgtttttgctcacccagaaacgctggtgaaagtaaaagatgctgaagatcagttgggtgcacgagtgggttacatcgaactggatct
caacagcggtaagatccttgagagttttcgccccgaagaacgttttccaatgatgagcacttttaaagttctgctatgtggcgcggtattat
cccgtattgacgccgggcaagagcaactcggtcgccgcatacactattctcagaatgacttggttgagtactcaccagtcacagaaaa
gcatcttacggatggcatgacagtaagagaattatgcagtgctgccataaccatgagtgataacactgcggccaacttacttctgacaac
gatcggaggaccgaaggagctaaccgcttttttgcacaacatgggggatcatgtaactcgccttgatcgttgggaaccggagctgaat
gaagccataccaaacgacgagcgtgacaccacgatgcctgtagcaatggcaacaacgttgcgcaaactattaactggcgaactactt
actctagcttcccggcaacaattaatagactggatggaggcggataaagttgcaggaccacttctgcgctcggcccttccggctggctg
gtttattgctgataaatctggagccggtgagcgtgggtctcgcggtatcattgcagcactggggccagatggtaagccctcccgtatcgt
agttatctacacgacggggagtcaggcaactatggatgaacgaaatagacagatcgctgagataggtgcctcactgattaagcattggt
aactgtcagaccaagtttactcatatatactttagattgatttaaaacttcatttttaatttaaaaggatctaggtgaagatcctttttgataatct
catgaccaaaatcccttaacgtgagttttcgttccactgagcgtcagaccccgtagaaaagatcaaaggatcttcttgagatcctttttttct
gcgcgtaatctgctgcttgcaaacaaaaaaaccaccgctaccagcggtggtttgtttgccggatcaagagctaccaactctttttccgaa
ggtaactggcttcagcagagcgcagataccaaatactgtccttctagtgtagccgtagttaggccaccacttcaagaactctgtagcacc
gcctacatacctcgctctgctaatcctgttaccagtggctgctgccagtggcgataagtcgtgtcttaccgggttggactcaagacgata

Figure 14 gttaccggataaggcgcagcggtcgggctgaacggggggttcgtgcacacagcccagcttggagcgaacgacctacaccgaactg
agatacctacagcgtgagcattgagaaagcgccacgcttcccgaagggagaaaggcggacaggtatccggtaagcggcagggtcg
gaacaggagagcgcacgagggagcttccagggggaaacgcctggtatctttatagtcctgtcgggtttcgccacctctgacttgagcg
tcgatttttgtgatgctcgtcaggggggcggagcctatggaaaaacgccagcaacgcggcctttttacggttcctggccttttgctggcc
ttttgctcacatgttctttcctgcgttatcccctgattctgtggataaccgtattaccgcctttgagtgagctgataccgctcgccgcagccg
aacgaccgagcgcagcgagtcagtgagcgaggaagcggaagagcgcctgatgcggtattttctccttacgcatctgtgcggtatttca
caccgcagaccagccgcgtaacctggcaaaatcggttacggttgagtaataaatggatgccctgcgtaagcgggtgtgggcggaca
ataaagtcttaaactgaacaaaatagatctaaactatgacaataaagtcttaaactagacagaatagttgtaaactgaaatcagtccagtta
tgctgtgaaaaagcatactggacttttgttatggctaaagcaaactcttcattttctgaagtgcaaattgcccgtcgtattaaagaggggcg
tggccaagggcatggtaaagactatattcgcggcgttgtgacaatttaccgaacaactccgcggccgggaagccgatctcggcttgaa
cgaattgatgttacgcagcagcaacgatgttacgcagcagggcagtcgccctaaaacaaagttaggtggctcaagtatgggcatcatt
cgcacatgtaggctcggccctgaccaagtcaaatccatgcgggctgctcttgatcttttcggtcgtgagttcggagacgtagccaccta
ctcccaacatcagccggactccgattacctcgggaacttgctccgtagtaagacattcatcgcgcttgctgccttcgaccaagaagcgg
ttgttggcgctctcgcggcttacgttctgcccaggtttgagcagccgcgtagtgagatctatatctatgatctcgcagtctccggcgagca
ccggaggcagggcattgccaccgcgctcatcaatctcctcaagcatgaggccaacgcgcttggtgcttatgtgatctacgtgcaagca
gattacggtgacgatcccgcagtggctctctatacaaagttgggcatacgggaagaagtgatgcactttgatatcgacccaagtaccgc
cacctaacgttgctgctccataacatcaaacatcgacccacggcgtaacgcgcttgctgcttggatgcccgaggcatagactgtacaaa
aaaacagtcataacaagccatgaaaaccgccactgcgccgttaccaccgctgcgttcggtcaaggttctggaccagttgcgtgagcg
catacgctacttgcattacagtttacgaaccgaacaggcttatgtcaactgggttcgtgccttcatccgtttccacggtgtgcgtcacccg
gcaaccttgggcagcagcgaagtcgaggcatttctgtcctggctggcgaacgagcgcaaggtttcggtctccacgcatcgtcaggca
ttggcggccttgctgttcttctacggcaaggtgctgtgcacggatctgccctggcttcaggagatcggtagacctcggccgtcgcggcg
cttgccggtggtgctgaccccggatgaagtggttcgcatcctcggttttctggaaggcgagcatcgtttgttcgcccaggactctagcta
tagttctagtggttggctacgtacccgtagtggctatggcagggcttgcgcttaatgcgccgctacagggcgcgtggggataccccta
gagccccagctggttctttccgcctcagaagccatagagcccaccgcatccccagcatgcctgctattgtcttcccaatcctcccccttg
ctgtcctgccccaccccaccccccagaatagaatgacacctactcagacaatgcgatgcaatttcctcattttattaggaaaggacagtg
ggagtggcaccttccagggtcaaggaaggcacgggggaggggcaaacaacagatggctggcaactagaaggcacagtcgaggc
tgatcagcgggtttaaacgggccctctagactcgagttaaagtcgacttaacgcgttgaattcTTACGCATAACGAATC
AGATAGTATTTCTTCTTGCCACGACGGATAACGGTAAAACGACCTTCCAGACGGT
GTTCCGCGGTCAGAATCGCGCCAACATCTTGCAGACGCTCGCCGTTCACGTAAAT
CGCACCGTTTTGGATGTCTTCACGCGCCTGACGTTTGCTCGGGCTGATACCCGCG
CTAACCAGCAGCTCAACCAGCGGCACATCGCCACCTTCGTGAACAAAGCTCGGC
ACGTCCTTGAAGCCTTGTTCAATCTCCGCCGCGGTCAGGTTCGCGATATCACCGC
TAAACAGCGCTTCGCTAATACGGATCGCCTGACGCAGCGCTTCCTCACCGTGAAC
CAGTTTGGTCACTTCCTCCGCCAGCGCTTTTTGCGCCCGCACGCTTTTCCGGCGCCT
CACGCAGTTCCTGCTCCAGCGCTTCGATTTCCTCTTTGCTCAGAAAGGTGAAATA
CTTCAGGTAACGAATAACGTCACGATCGTCGGTGTTGATCCAAAACTGATAGAAT
TCGTACGGGCTGGTTTTCTCCTTATCCAGCCAAATGGTACCGCTTTCGGTTTTGCC
AAACTTGGTACCGTCCGCCTTGGTCACCAGCGGGATGGTCAGGCCAAACGCACG
CGCTTCACCTTTGGTCTTACGAATCAGTTCCAGGCCCGCGGTGATGTTACCCCATT
GATCGCTGCCACCGATCTGCAGACGGCAGCCTTCGGTTTCGTAGGCACGCAGGA
AACCATACGCTTGCAGCATCATGTAGCTAAACTCGGTGAAGCTAATACCGGTTTC
GATACGGCTCTGAACGCTCTCTTTCGCCATCATGTAGTTAACGCTAAAGTGCTTG
CCCACATCACGCAGGAAGGTAATCACATCCAGCGGACCGATCCAGTCATAGTTG
TTTTTAATCTTCGCCGGGTTGCCATCCGCCTCAAAGTCCAGGAAACGACCCAGCT
GTTCTTTGATACGCGCGCTCCACGCTTCAACGGTTTCCTTCGCGTTCAGGGTACGC

Figure 14 continued

TCGCTTTTCTTGCCGCTCGGGTCGCCAATCAGACCGGTCGCACCACCAACCAGCG
CGATCGGACGGTGACCCGCTTGCTGAAAACGACGCAGGGTCAGAATCGCCGCCA
GGTTGCCGATGTGCAGGCTATCCGCGGTCGGGTCGAAACCGCAACCCAGGGTCA
CACGTTCCTCGTTCAGCAGTTTACGCAGGCCATCTTCGTCGGTGGTCTGATTAACC
AGGCCACGCCATTGCAGTTCCGCCAGCAGGTCCATggtggcgctagccagcttgggtctccctatag
tgagtcgtattaatttcgataagccagtaagcagtgggttctctagttagccagagagctCtagaccaagtgacgatcacagcgatcca
caaacaagaaccgcgacccaaatcccggctgcgacggaactagctgtgccacacccggcgcgtccttatataatcatcggcgttcac
cgccccacggagatccctccgcagaatcgccgagaagggactacttttcctcgcctgttccgctctctggaaagaaaaccagtgccct
agagtcacccaagtcccgtcctaaaatgtccttctgctgatactggggttctaaggccgagtcttatgagcagcgggccgctgtcctga
gcgtccgggcggaaggatcaggacgctcgctgcgcccttcgtctgacgtggcagcgctcgccgtgaggagggggcgcccgcgg
gaggcgccaaaacccggcgcggaggccttcgaacggCCActagcaaaaaaTGGAgGGGGACGGATTCGAA
CCGCCGAACCCAAAGGGAGCGGATTtgaAGTCCGCCGCGTTTAGCCACTTCGCTAC
CCCTCCgggGATCTGTGGTCTCATACAGAACTTATAAGATTCCCAAATCCAAAGAC
ATTTCACGTTTATGGTGATTTCCCAGAACACATAGCGACATGCAAATATTGCAGG
GCGCCACTCCCCTGTCCCTCACAGCCATCTTCCTGCCAGGGCGCACGCGCGCTGG
GTGTTCCCGCCTAGTGACACTGGGCCCGCGATTCCTTGGAGCGGGTTGATGACGT
CAGCGTTCGAATTCCTAGCAAAAAATGGTGGGGGAAGGATTCGAACCTTCGAAG
TCTGTGACGGCAGATTTgaAGTCTGCTCCCTTTGGCCGCTCGGGAACCCCACCGGT
GTTTCGTCCTTTCCACAAGATATATAAAGCCAAGAAATCGAAATACTTTCAAGTT
ACGGTAAGCATATGATAGTCCATTTTAAAACATAATTTTAAAACTGCAAACTACC
CAAGAAATTATTACTTTCTACGTCACGTATTTTGTACTAATATCTTTGTGTTTACA
GTCAAATTAATTCTAATTATCTCTCTAACAGCCTTGTATCGTATATGCAAATATGA
AGGAATCATGGGAAATAGGCCCTCTTCCTGCCCGACCTAGcaaaaaaTGGAgGGGGA
CGGATTCGAACCGCCGAACCCAAAGGGAGCGGATTtgaAGTCCGCCGCGTTTAGC
CACTTCGCTACCCCTCCgggGATCTGTGGTCTCATACAGAACTTATAAGATTCCCA
AATCCAAAGACATTTCACGTTTATGGTGATTTCCCAGAACACATAGCGACATGCA
AATATTGCAGGGCGCCACTCCCCTGTCCCTCACAGCCATCTTCCTGCCAGGGCGC
ACGCGCGCTGGGTGTTCCCGCCTAGTGACACTGGGCCCGCGATTCCTTGGAGCGG
GTTGATGACGTCAGCGTTCGAATTCCTAGCAAAAAATGGTGGGGGAAGGATTCG
AACCTTCGAAGTCTGTGACGGCAGATTTgaAGTCTGCTCCCTTTGGCCGCTCGGGA
ACCCCACCGGTGTTTCGTCCTTTCCACAAGATATATAAAGCCAAGAAATCGAAAT
ACTTTCAAGTTACGGTAAGCATATGATAGTCCATTTTAAAACATAATTTTAAAAC
TGCAAACTACCCAAGAAATTATTACTTTCTACGTCACGTATTTTGTACTAATATCT
TTGTGTTTACAGTCAAATTAATTCTAATTATCTCTCTAACAGCCTTGTATCGTATA
TGCAAATATGAAGGAATCATGGGAAATAGGCCCTCTTCCTGCCCGACctagcaaaaaaT
GGAgGGGGACGGATTCGAACCGCCGAACCCAAAGGGAGCGGATTtgaAGTCCGCC
GCGTTTAGCCACTTCGCTACCCCTCCgggGATCTGTGGTCTCATACAGAACTTATA
AGATTCCCAAATCCAAAGACATTTCACGTTTATGGTGATTTCCCAGAACACATAG
CGACATGCAAATATTGCAGGGCGCCACTCCCCTGTCCCTCACAGCCATCTTCCTG
CCAGGGCGCACGCGCGCTGGGTGTTCCCGCCTAGTGACACTGGGCCCGCGATTCC
TTGGAGCGGGTTGATGACGTCAGCGTTCGAATTCCTAGCAAAAAATGGTGGGGG
AAGGATTCGAACCTTCGAAGTCTGTGACGGCAGATTTgaAGTCTGCTCCCTTTGGC
CGCTCGGGAACCCCACCGGTGTTTCGTCCTTTCCACAAGATATATAAAGCCAAGA
AATCGAAATACTTTCAAGTTACGGTAAGCATATGATAGTCCATTTTAAAACATAA
TTTTAAAACTGCAAACTACCCAAGAAATTATTACTTTCTACGTCACGTATTTTGTA

Figure 14 continued

CTAATATCTTTGTGTTTACAGTCAAATTAATTCTAATTATCTCTCTAACAGCCTTG
TATCGTATATGCAAATATGAAGGAATCATGGGAAATAGGCCCTCTTCCTGCCCGA
CCTAGcaaaaaaGGAGGGGTAGCGAAGTGGCTAAACGCGGCGGACTtcaAATCCGCTC
CCTTTGGGTTCGGCGGTTCGAATCCGTCCCCcTCCAgggGATCTGTGGTCTCATACA
GAACTTATAAGATTCCCAAATCCAAAGACATTTCACGTTTATGGTGATTTCCCAG
AACACATAGCGACATGCAAATATTGCAGGGCGCCACTCCCCTGTCCCTCACAGCC
ATCTTCCTGCCAGGGCGCACGCGCGCTGGGTGTTCCCGCCTAGTGACACTGGGCC
CGCGATTCCTTGGAGCGGGTTGATGACGTCAGCGTTCGAATTCCTAGCAAAAAAT
GGTGGGGGAAGGATTCGAACCTTCGAAGTCTGTGACGGCAGATTTgaAGTCTGCT
CCCTTTGGCCGCTCGGGAACCCCACCGGTGTTTCGTCCTTTCCACAAGATATATA
AAGCCAAGAAATCGAAATACTTTCAAGTTACGGTAAGCATATGATAGTCCATTTT
AAAACATAATTTTAAAACTGCAAACTACCCAAGAAATTATTACTTTCTACGTCAC
GTATTTTGTACTAATATCTTTGTGTTTACAGTCAAATTAATTCTAATTATCTCTCTA
ACAGCCTTGTATCGTATATGCAAATATGAAGGAATCATGGGAAATAGGCCCTCTT
CCTGCCCGACctagcaaaaaaGGAGGGGTAGCGAAGTGGCTAAACGCGGCGGACTtcaA
ATCCGCTCCCTTTGGGTTCGGCGGTTCGAATCCGTCCCCcTCCAgggGATCTGTGGT
CTCATACAGAACTTATAAGATTCCCAAATCCAAAGACATTTCACGTTTATGGTGA
TTTCCCAGAACACATAGCGACATGCAAATATTGCAGGGCGCCACTCCCCTGTCCC
TCACAGCCATCTTCCTGCCAGGGCGCACGCGCGCTGGGTGTTCCCGCCTAGTGAC
ACTGGGCCCGCGATTCCTTGGAGCGGGTTGATGACGTCAGCGTTCGAATTCCTAG
CAAAAAATGGTGGGGGAAGGATTCGAACCTTCGAAGTCTGTGACGGCAGATTTga
AGTCTGCTCCCTTTGGCCGCTCGGGAACCCCACCGGTGTTTCGTCCTTTCCACAA
GATATATAAAGCCAAGAAATCGAAATACTTTCAAGTTACGGTAAGCATATGATA
GTCCATTTTAAAACATAATTTTAAAACTGCAAACTACCCAAGAAATTATTACTTT
CTACGTCACGTATTTTGTACTAATATCTTTGTGTTTACAGTCAAATTAATTCTAAT
TATCTCTCTAACAGCCTTGTATCGTATATGCAAATATGAAGGAATCATGGGAAAT
AGGCCCTCTTCCTGCCCGACCTAGcaaaaaaTGGAgGGGACGGATTCGAACCGCCG
AACCCAAAGGGAGCGGATTtgaAGTCCGCCGCGTTTAGCCACTTCGCTACCCCTCC
gggGATCTGTGGTCTCATACAGAACTTATAAGATTCCCAAATCCAAAGACATTTCA
CGTTTATGGTGATTTCCCAGAACACATAGCGACATGCAAATATTGCAGGGCGCCA
CTCCCCTGTCCCTCACAGCCATCTTCCTGCCAGGGCGCACGCGCGCTGGGTGTTC
CCGCCTAGTGACACTGGGCCCGCGATTCCTTGGAGCGGGTTGATGACGTCAGCGT
TCGAATTCCTAGCAAAAAATGGTGGGGGAAGGATTCGAACCTTCGAAGTCTGTG
ACGGCAGATTTgaAGTCTGCTCCCTTTGGCCGCTCGGGAACCCCACCGGTGTTTCG
TCCTTTCCACAAGATATATAAAGCCAAGAAATCGAAATACTTTCAAGTTACGGTA
AGCATATGATAGTCCATTTTAAAACATAATTTTAAAACTGCAAACTACCCAAGAA
ATTATTACTTTCTACGTCACGTATTTTGTACTAATATCTTTGTGTTTACAGTCAAA
TTAATTCTAATTATCTCTCTAACAGCCTTGTATCGTATATGCAAATATGAAGGAAT
CATGGGAAATAGGCCCTCTTCCTGCCCGACctagcaaaaaaGGAGGGGTAGCGAAGTG
GCTAAACGCGGCGGACTtcaAATCCGCTCCCTTTGGGTTCGGCGGTTCGAATCCGT
CCCCcTCCAgggGATCTGTGGTCTCATACAGAACTTATAAGATTCCCAAATCCAAA
GACATTTCACGTTTATGGTGATTTCCCAGAACACATAGCGACATGCAAATATTGC
AGGGCGCCACTCCCCTGTCCCTCACAGCCATCTTCCTGCCAGGGCGCACGCGCGC
TGGGTGTTCCCGCCTAGTGACACTGGGCCCGCGATTCCTTGGAGCGGGTTGATGA
CGTCAGCGTTCGAATTCCTAGCAAAAAATGGTGGGGGAAGGATTCGAACCTTCG

Figure 14 continued

AAGTCTGTGACGGCAGATTTgaAGTCTGCTCCCTTTGGCCGCTCGGGAACCCCACC
GGTGTTTCGTCCTTTCCACAAGATATATAAAGCCAAGAAATCGAAATACTTTCAA
GTTACGGTAAGCATATGATAGTCCATTTTAAAACATAATTTTAAAACTGCAAACT
ACCCAAGAAATTATTACTTTCTACGTCACGTATTTTGTACTAATATCTTTGTGTTT
ACAGTCAAATTAATTCTAATTATCTCTCTAACAGCCTTGTATCGTATATGCAAATA
TGAAGGAATCATGGGAAATAGGCCCTCTTCCTGCCCGACCTAGcaaaaaaGGAGGGG
TAGCGAAGTGGCTAAACGCGGCGGACTtcaAATCCGCTCCCTTTGGGTTCGGCGGT
TCGAATCCGTCCCCcTCCAgggGATCTGTGGTCTCATACAGAACTTATAAGATTCCC
AAATCCAAAGACATTTCACGTTTATGGTGATTTCCCAGAACACATAGCGACATGC
AAATATTGCAGGGCGCCACTCCCCTGTCCCTCACAGCCATCTTCCTGCCAGGGCG
CACGCGCGCTGGGTGTTCCCGCCTAGTGACACTGGGCCCGCGATTCCTTGGAGCG
GGTTGATGACGTCAGCGTTCGAATTCCTAGCAAAAAATGGTGGGGGAAGGATTC
GAACCTTCGAAGTCTGTGACGGCAGATTTgaAGTCTGCTCCCTTTGGCCGCTCGGG
AACCCCACCGGTGTTTCGTCCTTTCCACAAGATATATAAAGCCAAGAAATCGAAA
TACTTTCAAGTTACGGTAAGCATATGATAGTCCATTTTAAAACATAATTTTAAAA
CTGCAAACTACCCAAGAAATTATTACTTTCTACGTCACGTATTTTGTACTAATATC
TTTGTGTTTACAGTCAAATTAATTCTAATTATCTCTCTAACAGCCTTGTATCGTAT
ATGCAAATATGAAGGAATCATGGGAAATAGGCCCTCTTCCTGCCCGACctagtcaataat
caatgtcaacgcgtatatctggcccgtacatcgcgaagcagcgcaaaacGGATCCtgcaggtatttGCGGCCGCggtccg
tatactccggaatattaatagatcatggagataattaaaatgataaccatctcgcaaataaataagtattttactgttttcgtaacagttttgta
ataaaaaaacctataaatattccggattattcataccgtcccaccatcgggcgcgAACTCCTAAAAAACCGCCACCa
tgaagtgccttttgtacttagcctttttattcattggggtgaattgcaagttcaccatagtttttccacacaaccaaaaaggaaactggaaaa
atgttccttctaattaccattattgcccgtcaagctcagatttaaattggcataatgacttaataggcacagccttacaagtcaaaatgccca
agagtcacaaggctattcaagcagacggttggatgtgtcatgcttccaaatgggtcactacttgtgatttccgctggtatggaccgaagt
atataacacattccatccgatccttcactccatctgtagaacaatgcaaggaaagcattgaacaaacgaaacaaggaacttggctgaatc
caggcttccctcctcaaagttgtggatatgcaactgtgacggatgccgaagcagtgattgtccaggtgactcctcaccatgtgctggttg
atgaatacacaggagaatgggttgattcacagttcatcaacggaaaatgcagcaattacatatgccccactgtccataactctacaacct
ggcattctgactataaggtcaaagggctatgtgattctaacctcatttccatggacatcaccttcttctcagaggacggagagctatcatcc
ctgggaaaggagggcacagggttcagaagtaactactttgcttatgaaactggaggcaaggcctgcaaaatgcaatactgcaagcatt
ggggagtcagactcccatcaggtgtctggttcgagatggctgataaggatctctttgctgcagccagattccctgaatgcccagaaggg
tcaagtatctctgctccatctcagacctcagtggatgtaagtctaattcaggacgttgagaggatcttggattattccctctgccaagaaac
ctggagcaaaatcagagcgggtcttccaatctctccagtggatctcagctatcttgctcctaaaaacccaggaaccggtcctgctttcac
cataatcaatggtaccctaaaatactttgagaccagatacatcagagtcgatattgctgctccaatcctctcaagaatggtcggaatgatc
agtggaactaccacagaaagggaactgtgggatgactgggcaccatatgaagacgtggaaattggacccaatggagttctgaggac
cagttcaggatataagtttcctttatacatgattggacatggtatgttggactccgatcttcatcttagctcaaaggctcaggtgttcgaacat
cctcacattcaagacgctgcttcgcaacttcctgatgatgagagtttatttttggtgatactgggctatccaaaaatccaatcgagcttgta
gaaggttggttcagtagttggaaaagctctattgcctctttttctttatcatagggttaatcattggactattcttggttctccgagttggtatc
catctttgcattaaattaaagcacaccaagaaaagacagatttatacagacatagagatgaaccgacttggaaagtgataaggccaggc
cggccaagcttgtcgagaagtactagaggatcataatcagccataccacatttgtagaggttttacttgctttaaaaaacctcccacacct
ccccctgaacctgaaacataaaatgaatgcaattgttgttgttaacttgtttattgcagcttataatggttacaaataaagcaatagcatcac
aaatttcacaaataaagcatttttttcactgcattctagttgtggtttgtccaaactcatcaatgtatcttatcatgtctggatctgatcactgctt
gagcctaggagatccgaaccagataagtgaaatctagttccaaactattttgtcatttttaattttcgtattagcttacgacgctacacccag
ttcccatctattttgtcactcttccctaaataatccttaaaaactccatttccacccctcccagttcccaactattttgtccgcccacagcggg
gcatttttcttcctgttatgttttaatcaaacatcctgccaactccatgtgacaaaccgtcatcttcggctacttt

Figure 14 continued pB1U Ec-BPA-RS
Same as above but with the following aaRS sequence:
atgGCAAGCAGTAACTTGATTAAACAATTGCAAGAGCGGGGGCTGGTAGCCCAGG
TGACGGACGAGGAAGCGTTAGCAGAGCGACTGGCGCAAGGCCCGATCGCGCTCG
GTTGCGGCTTCGATCCTACCGCTGACAGCTTGCATTTGGGGCATCTTGTTCCATTG
TTATGCCTGAAACGCTTCCAGCAGGCGGGCCACAAGCCGGTTGCGCTGGTAGGC
GGCGCGACGGGTCTGATTGGCGACCCGAGCTTCAAAGCTGCCGAGCGTAAGCTG
AACACCGAAGAAACTGTTCAGGAGTGGGTGGACAAAATCCGTAAGCAGGTTGCC
CCGTTCCTCGATTTCGACTGTGGAGAAAACTCTGCTATCGCGGCGAACAACTATG
ACTGGTTCGGCAATATGAATGTGCTGACCTTCCTGCGCGATATTGGCAAACACTT
CTCCGTTAACCAGATGATCAACAAAGAAGCGGTTAAGCAGCGTCTCAACCGTGA
AGATCAGGGGATTTCGTTCACTGAGTTTTCCTACAACCTGTTGCAGGGTTATGGT
TTCGCaTGTGCTAACAAACAGTACGGTGTGGTGCTGCAAATTGGTGGTTCTGACC
AGTGGGGTAACATCACTTCTGGTATCGACCTGACCCGTCGTCTGCATCAGAATCA
GGTGTTTGGCCTGACCGTTCCGCTGATCACTAAAGCAGATGGCACCAAATTTGGT
AAAACTGAAGGCGGCGCAGTCTGGTTaGATCCGAAGAAAACCAGCCCGTACAAA
TTCTACCAGTTCTGGATCAACACTGCGCGTGCCGACGTTTACCGCTTCCTGAAGTT
CTTCACCTTTATGAGCATTGAAGAGATCAACGCCCTGGAAGAAGAAGATAAAAA
CAGCGGTAAAGCACCGCGCGCCCAGTATGTACTGGCGGAGCAGGTGACTCGTCT
GGTTCACGGTGAAGAAGGTTTACAGGCGGCAAAACGTATTACCGAATGCCTGTT
CAGCGGTTCTTTGAGTGCGCTGAGTGAAGCGGACTTCGAACAGCTGGCGCAGGA
CGGCGTACCGATGGTTGAGATGGAAAAGGGCGCAGACCTGATGCAGGCACTGGT
CGATTCTGAACTGCAACCTTCCCGTGGTCAGGCACGTAAAACTATCGCCTCCAAT
GCCATCACCATTAACGGTGAAAAACAGTCCGATCCTGAATACTTCTTTAAAGAAG
AAGATCGTCTGTTTGGTCGTTTTACCTTACTGCGTCGCGGTAAAAAGAATTACTG
TCTGATTTGCTGGAAAtaa pB1U Ec-OMeY-RS
Same as Ec-BPA-RS but with the following active site mutations:
Y37V, D182S, F183M, L186A pB1U H2-BPA-RS
Same as above but with the following aaRS sequence:
atgGCAAGCAGTAACTTGATTAAACAATTGCAAGAGCGGGGGCTGGTAGCCCAGG
TGACGGACGAGGAAGCGTTAGCAGAGCGACTGGCGCAAGGCCCGATCGCGCTCG
GGTGCGGCTTCGATCCTACCGCTGACAGCTTGCATTTGGGGCATCTTGTTCCATTG
TTATGCCTGAAACGCTTCCAGCAGGCGGGTCACCGTCCGATCGCGCTGGTTGGTG
GTGCGACCGGTCTGATTGGCGACCCGAGCGGCAAGAAAAGCGAGCGTACCCTGA
ACGCGAAGGAAACCGTTGAAGCGTGGAGCGCGCGTATCAAAGAACAGCTGGGTC
GTTTCCTGGACTTTGAGGCGGATGGCAACCCGGCGAAGATTAAAAACAACTATG
ACTGGATCGGTCCGCTGGATGTGATTACCTTCCTGCGTGATGTGGGCAAGCACTT
TAGCGTTAACTACATGATGGCGAAAGAGAGCGTTCAGAGCCGTATCGAAACCGG
TATTAGCTTCACCGAGTTTAGCTACATGATGCTGCAAGCGTATGGTTTCCTGCGT
GCCTACGAAACCGAAGGCTGCCGTCTGCAGATCGGTGGCAGCGATCAATGGGGT
AACATCACCGCGGGCCTGGAACTGATTCGTAAGACCAAAGGTGAAGCGCGTGCG

Figure 14 continued

TTTGGCCTGACCATCCCGCTGGTGACCAAGGCGGACGGTACCAAGTTTGGCAAA
ACCGAAAGCGGTACCATTTGGCTGGATAAGGAGAAAACCAGCCCGTACGAATTC
TATCAGTTTTGGATCAACACCGACGATCGTGACGTTATTCGTTACCTGAAGTATTT
CACCTTTCTGAGCAAAGAGGAAATCGAAGCGCTGGAGCAGGAACTGCGTGAGGC
GCCGGAAAAGCGTGCGGCGCAAAAAGCGCTGGCGGAGGAAGTGACCAAACTGG
TTCACGGTGAGGAAGCGCTGCGTCAGGCGATCCGTATTAGCGAAGCGCTGTTTAG
CGGTGATATCGCGAACCTGACCGCGGCGGAGATTGAACAAGGCTTCAAGGACGT
GCCGAGCTTTGTTCACGAAGGTGGCGATGTGCCGCTGGTTGAGCTGCTGGTTAGC
GCGGGTATCAGCCCGAGCAAACGTCAGGCGCGTGAAGACATCCAAAACGGTGCG
ATTTACGTGAACGGCGAGCGTCTGCAAGATGTTGGCGCGATTCTGACCGCGGAA
CACCGTCTGGAAGGTCGTTTTACCGTTATCCGTCGTGGCAAGAAGAAATACTATC
TGATTCGTTATGCGTAA pB1U H2-OMeY-RS
Same as H2-BPA-RS but with the following active site mutations:
Y37V, D176S, F180M, L183A pB1U H6 BPA-RS
Same as above but with the following aaRS sequence:
atgGCAAGCAGTAACTTGATTAAACAATTGCAAGAGCGGGGGCTGGTAGCCCAGG
TGACGGACGAGGAAGCGTTAGCAGAGCGACTGGCGCAAGGCCCGATCGCGCTCG
GGTGCGGCTTCGATCCTACCGCTGACAGCTTGCATTTGGGGCATCTTGTTCCATTG
TTATGCCTGAAACGCTTCCAGCAGGCGGGCCACAAGCCGGTTGCGCTGGTAGGC
GGCGCGACGGGTCTGATTGGCGACCCGAGTTTCAAAGCTGCCGAGCGTAAGCTG
AACACCGAAGAAACTGTTCAGGAGTGGGTGGACAAAATCCGTAAGCAGGTTGCC
CCGTTCCTCGATTTCGACTGTGGAGAAAACTCTGCTATCGCGGCGAACAACTATG
ACTGGTTCGGCAATATGAATGTGCTGACCTTCCTGCGCGATATTGGCAAACACTT
CTCCGTTAACCAGATGATCAACAAAGAAGCGGTTAAGCAGCGTCTCAACCGTGA
AGATCAGGGGATTTCGTTCACTGAGTTTTCCTACAGCCTGTTGCAGGGTTATGGG
TTCGCCTGTGCTAACAAACAGTACGGTGTGGTGCTGCAAATTGGTGGTTCTGACC
AGTGGGGTAACATCACTTCTGGTATCGACCTGACCCGTCGTCTGCATCAGAATCA
GGTGTTTGGCCTGACCGTTCCGCTGATCACTAAAGCAGATGGCACCAAATTTGGC
AAAACCGAAAGCGGTACCATTTGGCTGGATAAGGAGAAAACCAGCCCGTACGAA
TTCTATCAGTTTTGGATCAACACCGACGATCGTGACGTTATTCGTTACCTGAAGT
ATTTCACCTTTCTGAGCAAAGAGGAAATCGAAGCGCTGGAGCAGGAACTGCGTG
AGGCGCCGGAAAAGCGTGCGGCGCAAAAAGCGCTGGCGGAGGAAGTGACCAAA
CTGGTTCACGGTGAGGAAGCGCTGCGTCAGGCGATCCGTATTAGCGAAGCGCTG
TTTAGCGGTGATATCGCGAACCTGACCGCGGCGGAGATTGAACAAGGCTTCAAG
GACGTGCCGAGCTTTGTTCACGAAGGTGGCGATGTGCCGCTGGTTGAGCTGCTGG
TTAGCGCGGGTATCAGCCCGAGCAAACGTCAGGCGCGTGAAGACATCCAAAACG
GTGCGATTTACGTGAACGGCGAGCGTCTGCAAGATGTTGGCGCGATTCTGACCGC
GGAACACCGTCTGGAAGGTCGTTTTACCGTTATCCGTCGTGGCAAGAAGAAATAC
TATCTGATTCGTTATGCGTAA

Figure 14 continued

Ch2TyrRS-WT

Nucleotide sequence:

atgGCAAGCAGTAACTTGATTAAACAATTGCAAGAGCGGGGGCTGGTAGCCCAGG
TGACGGACGAGGAAGCGTTAGCAGAGCGACTGGCGCAAGGCCCGATCGCGCTCT
ATTGCGGCTTCGATCCTACCGCTGACAGCTTGCATTTGGGGCATCTTGTTCCATTG
TTATGCCTGAAACGCTTCCAGCAGGCGGGTCACCGTCCGATCGCGCTGGTTGGTG
GTGCGACCGGTCTGATTGGCGACCCGAGCGGCAAGAAAAGCGAGCGTACCCTGA
ACGCGAAGGAAACCGTTGAAGCGTGGAGCGCGCGTATCAAAGAACAGCTGGGTC
GTTTCCTGGACTTTGAGGCGGATGGCAACCCGGCGAAGATTAAAAACAACTATG
ACTGGATCGGTCCGCTGGATGTGATTACCTTCCTGCGTGATGTGGGCAAGCACTT
TAGCGTTAACTACATGATGGCGAAAGAGAGCGTTCAGAGCCGTATCGAAACCGG
TATTAGCTTCACCGAGTTTAGCTACATGATGCTGCAAGCGTATGACTTCCTGCGT
CTGTACGAAACCGAAGGCTGCCGTCTGCAGATCGGTGGCAGCGATCAATGGGGT
AACATCACCGCGGGCCTGGAACTGATTCGTAAGACCAAAGGTGAAGCGCGTGCG
TTTGGCCTGACCATCCCGCTGGTGACCAAGGCGGACGGTACCAAGTTTGGCAAA
ACCGAAAGCGGTACCATTTGGCTGGATAAGGAGAAAACCAGCCCGTACGAATTC
TATCAGTTTTGGATCAACACCGACGATCGTGACGTTATTCGTTACCTGAAGTATTT
CACCTTTCTGAGCAAAGAGGAAATCGAAGCGCTGGAGCAGGAACTGCGTGAGGC
GCCGGAAAAGCGTGCGGCGCAAAAAGCGCTGGCGGAGGAAGTGACCAAACTGG
TTCACGGTGAGGAAGCGCTGCGTCAGGCGATCCGTATTAGCGAAGCGCTGTTTAG
CGGTGATATCGCGAACCTGACCGCGGCGGAGATTGAACAAGGCTTCAAGGACGT
GCCGAGCTTTGTTCACGAAGGTGGCGATGTGCCGCTGGTTGAGCTGCTGGTTAGC
GCGGGTATCAGCCCGAGCAAACGTCAGGCGCGTGAAGACATCCAAAACGGTGCG
ATTTACGTGAACGGCGAGCGTCTGCAAGATGTTGGCGCGATTCTGACCGCGGAA
CACCGTCTGGAAGGTCGTTTTACCGTTATCCGTCGTGGCAAGAAGAAATACTATC
TGATTCGTTATGCGTAA Amino acid sequence:

MASSNLIKQLQERGLVAQVTDEEALAERLAQGPIALYCGFDPTADSLHLGHLVPLLC
LKRFQQAGHRPIALVGGATGLIGDPSGKKSERTLNAKETVEAWSARIKEQLGRFLDF
EADGNPAKIKNNYDWIGPLDVITFLRDVGKHFSVNYMMAKESVQSRIETGISFTEFSY
MMLQAYDFLRLYETEGCRLQIGGSDQWGNITAGLELIRKTKGEARAFGLTIPLVTKA
DGTKFGKTESGTIWLDKEKTSPYEFYQFWINTDDRDVIRYLKYFTFLSKEEIEALEQE
LREAPEKRAAQKALAEEVTKLVHGEEALRQAIRISEALFSGDIANLTAAEIEQGFKDV
PSFVHEGGDVPLVELLVSAGISPSKRQAREDIQNGAIYVNGERLQDVGAILTAEHRLE
GRFTVIRRGKKKYYLIRYA*

Ch2TyrRS-pBPA

Amino acid sequence:

Mutations highlighted in red: Y37G, D179G, L183A

MASSNLIKQLQERGLVAQVTDEEALAERLAQGPIALGCGFDPTADSLHLGHLVPLLC

Figure 15

LKRFQQAGHRPIALVGGATGLIGDPSGKKSERTLNAKETVEAWSARIKEQLGRFLDF
EADGNPAKIKNNYDWIGPLDVITFLRDVGKHFSVNYMMAKESVQSRIETGISFTEFSY
MMLQAYGFLRAYETEGCRLQIGGSDQWGNITAGLELIRKTKGEARAFGLTIPLVTKA
DGTKFGKTESGTIWLDKEKTSPYEFYQFWINTDDRDVIRYLKYFTFLSKEEIEALEQE
LREAPEKRAAQKALAEEVTKLVHGEEALRQAIRISEALFSGDIANLTAAEIEQGFKDV
PSFVHEGGDVPLVELLVSAGISPSKRQAREDIQNGAIYVNGERLQDVGAILTAEHRLE
GRFTVIRRGKKKYYLIRYA*

Ch2TyrRS-poly

Amino acid sequence:

Mutations highlighted in red: Y37V, D176S, F180M, L183A

MASSNLIKQLQERGLVAQVTDEEALAERLAQGPIALVCGFDPTADSLHLGHLVPLLC
LKRFQQAGHRPIALVGGATGLIGDPSGKKSERTLNAKETVEAWSARIKEQLGRFLDF
EADGNPAKIKNNYDWIGPLDVITFLRDVGKHFSVNYMMAKESVQSRIETGISFTEFSY
MMLQAYSMLRAYETEGCRLQIGGSDQWGNITAGLELIRKTKGEARAFGLTIPLVTKA
DGTKFGKTESGTIWLDKEKTSPYEFYQFWINTDDRDVIRYLKYFTFLSKEEIEALEQE
LREAPEKRAAQKALAEEVTKLVHGEEALRQAIRISEALFSGDIANLTAAEIEQGFKDV
PSFVHEGGDVPLVELLVSAGISPSKRQAREDIQNGAIYVNGERLQDVGAILTAEHRLE
GRFTVIRRGKKKYYLIRYA*

Ch6TyrRS-WT

Nucleotide sequence:

atgGCAAGCAGTAACTTGATTAAACAATTGCAAGAGCGGGGGCTGGTAGCCCAGG
TGACGGACGAGGAAGCGTTAGCAGAGCGACTGGCGCAAGGCCCGATCGCGCTCT
ATTGCGGCTTCGATCCTACCGCTGACAGCTTGCATTTGGGGCATCTTGTTCCATTG
TTATGCCTGAAACGCTTCCAGCAGGCGGGCCACAAGCCGGTTGCGCTGGTAGGC
GGCGCGACGGGTCTGATTGGCGACCCGAGCTTCAAAGCTGCCGAGCGTAAGCTG
AACACCGAAGAAACTGTTCAGGAGTGGGTGGACAAAATCCGTAAGCAGGTTGCC
CCGTTCCTCGATTTCGACTGTGGAGAAAACTCTGCTATCGCGGCGAACAACTATG
ACTGGTTCGGCAATATGAATGTGCTGACCTTCCTGCGCGATATTGGCAAACACTT
CTCCGTTAACCAGATGATCAACAAAGAAGCGGTTAAGCAGCGTCTCAACCGTGA
AGATCAGGGGATTTCGTTCACTGAGTTTTCCTACAGCCTGTTGCAGGGTTATGAC
TTCGCCTGTCTGAACAAACAGTACGGTGTGGTGCTGCAAATTGGTGGTTCTGACC
AGTGGGGTAACATCACTTCTGGTATCGACCTGACCCGTCGTCTGCATCAGAATCA
GGTGTTTGGCCTGACCGTTCCGCTGATCACTAAAGCAGATGGCACCAAATTTGGC
AAAACCGAAAGCGGTACCATTTGGCTGGATAAGGAGAAAACCAGCCCGTACGAA
TTCTATCAGTTTTGGATCAACACCGACGATCGTGACGTTATTCGTTACCTGAAGT
ATTTCACCTTTCTGAGCAAAGAGGAAATCGAAGCGCTGGAGCAGGAACTGCGTG
AGGCGCCGGAAAAGCGTGCGGCGCAAAAAGCGCTGGCGGAGGAAGTGACCAAA
CTGGTTCACGGTGAGGAAGCGCTGCGTCAGGCGATCCGTATTAGCGAAGCGCTG
TTTAGCGGTGATATCGCGAACCTGACCGCGGCGGAGATTGAACAAGGCTTCAAG
GACGTGCCGAGCTTTGTTCACGAAGGTGGCGATGTGCCGCTGGTTGAGCTGCTGG

Figure 15 continued

TTAGCGCGGGTATCAGCCCGAGCAAACGTCAGGCGCGTGAAGACATCCAAAACG
GTGCGATTTACGTGAACGGCGAGCGTCTGCAAGATGTTGGCGCGATTCTGACCGC
GGAACACCGTCTGGAAGGTCGTTTTACCGTTATCCGTCGTGGCAAGAAGAAATAC
TATCTGATTCGTTATGCGTAA

Amino acid sequence:

MASSNLIKQLQERGLVAQVTDEEALAERLAQGPIALYCGFDPTADSLHLGHLVPLLC
LKRFQQAGHKPVALVGGATGLIGDPSFKAAERKLNTEETVQEWVDKIRKQVAPFLD
FDCGENSAIAANNYDWFGNMNVLTFLRDIGKHFSVNQMINKEAVKQRLNREDQGIS
FTEFSYSLLQGYDFACLNKQYGVVLQIGGSDQWGNITSGIDLTRRLHQNQVFGLTVP
LITKADGTKFGKTESGTIWLDKEKTSPYEFYQFWINTDDRDVIRYLKYFTFLSKEEIEA
LEQELREAPEKRAAQKALAEEVTKLVHGEEALRQAIRISEALFSGDIANLTAAEIEQG
FKDVPSFVHEGGDVPLVELLVSAGISPSKRQAREDIQNGAIYVNGERLQDVGAILTAE
HRLEGRFTVIRRGKKKYYLIRYA*

Ch6TyrRS-pBPA

Amino acid sequence:

Mutations highlighted in red: Y37G, D182G, L186A

MASSNLIKQLQERGLVAQVTDEEALAERLAQGPIALGCGFDPTADSLHLGHLVPLLC
LKRFQQAGHKPVALVGGATGLIGDPSFKAAERKLNTEETVQEWVDKIRKQVAPFLD
FDCGENSAIAANNYDWFGNMNVLTFLRDIGKHFSVNQMINKEAVKQRLNREDQGIS
FTEFSYSLLQGYGFACANKQYGVVLQIGGSDQWGNITSGIDLTRRLHQNQVFGLTVP
LITKADGTKFGKTESGTIWLDKEKTSPYEFYQFWINTDDRDVIRYLKYFTFLSKEEIEA
LEQELREAPEKRAAQKALAEEVTKLVHGEEALRQAIRISEALFSGDIANLTAAEIEQG
FKDVPSFVHEGGDVPLVELLVSAGISPSKRQAREDIQNGAIYVNGERLQDVGAILTAE
HRLEGRFTVIRRGKKKYYLIRYA*

Figure 15 continued

CHIMERIC THERMOSTABLE AMINOACYL-tRNA SYNTHETASE FOR ENHANCED UNNATURAL AMINO ACID INCORPORATION

RELATED APPLICATIONS

This application is a § 371 National Phase Application of International Application No. PCT/US2020/055834, filed on Oct. 15, 2020, which claims the benefit under 35 U.S.C. § 119(c) of U.S. Provisional Application No. 62/973,599, filed on Oct. 15, 2019, both of which are incorporated herein by reference in their entirety.

GOVERNMENT SUPPORT

The current technology was developed using funds supplied by the National Institutes of Health (NIH) under grant Nos: R01GM126220, R01GM124319 and NIH/NIGMS R35 GM136437. Accordingly, the U.S. Government has certain rights to this invention.

SEQUENCE LISTING

The instant application contains a Sequence Listing which has been submitted electronically in ASCII format and is hereby incorporated by reference in its entirety. Said ASCII copy, created on Oct. 15, 2020, is named 0342_0009WO1_SL.txt and is 87,778 bytes in size.

FIELD OF THE INVENTION

The present invention is directed to the field of biotechnology, focusing on developing efficient platforms for expressing proteins site-specifically incorporating unnatural amino acids.

BACKGROUND OF THE INVENTION

Site-specific incorporation of unnatural amino acids (Uaas) holds much potential to probe and engineer the biology of mammalian cells. Central to this technology is an aminoacyl-tRNA synthetase (aaRS)/tRNA pair, which is engineered to charge the Uaa of interest in response to a nonsense or a frameshift codon, without cross-reacting with any of its host counterparts. Such “orthogonal” aaRS/tRNA pairs are typically imported into the host cell from a different domain of life. Thus, incorporation of Uaas in eukaryotic cells is mainly dependent on aaRS/tRNA pairs derived from bacteria.

So far, three different bacterial aaRS/tRNA pairs have been used for Uaa incorporation in eukaryotes—ones charging tyrosine, leucine, and tryptophan—all derived from *E. coli*. The *E. coli* tyrosyl-tRNA synthetase (EcTyrRS)/tRNA pair was the first pair that was successfully engineered to incorporate Uaas in eukaryotes nearly two decades ago. Yet, the number of Uaa-selective mutants that has been generated using this pair remains very limited. In contrast, an archaea-derived tyrosyl pair, which has a similar active site architecture to EcTyrRS, has been successfully engineered to charge over 100 Uaas with high selectivity and efficiency. However, the archaea-derived tyrosyl pair cannot be used in eukaryotes, as it cross-reacts with its eukaryotic counterpart. The ability to further engineer the bacterial TyrRS/tRNA pair to accept a wider variety of Uaas will be extremely valuable for numerous applications related to probing and engineering protein structure and function in eukaryotic cells.

It has been previously observed that introducing mutations into a protein’s active site to alter its activity is often associated with a decrease in the stability of its tertiary and quaternary structure. It is hypothesized that the outstanding success in engineering the archaeal TyrRS can be explained by its high structural stability, which ensures that a large set of its engineered mutants are still viable at physiological temperature in spite of suffering a drop in overall stability. In contrast, the EcTyrRS exhibits significantly lower thermostability. Consequently, destabilization associated with engineered mutations can more readily lead to proteins that are not viable at the physiological temperature. Such catastrophic loss of stability prevents access to EcTyrRS mutants that can potentially charge a wider assortment of structurally novel Uaas. The ability to develop a more thermostable bacterial TyrRS would overcome this limitation and will provide access to more extensively engineered mutants that charge structurally disparate Uaas. The same concept can be extended to all bacteria-derived aaRS mutants that are or can be engineered for Uaa incorporation in eukaryotic cells.

SUMMARY OF THE INVENTION

As used herein, the term “and/or” includes any and all combinations of one or more of the associated listed items. Further, the singular forms and the articles “a”, “an” and “the” are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof.

The present invention establishes a new strategy to generate chimeric aminoacyl-tRNA synthetase/tRNA pairs derived from bacteria that demonstrate high thermostability, as well as activity, and can be more aggressively engineered to generate mutants that can activate a broader selection of Uaas. Also described herein are compositions, such as the composition of chimeric TyrRS, derived from bacteria which are more stable, active and engineerable than their wild-type counterparts.

Further, the present invention describes a method to generate chimeric bacterial aminoacyl-tRNA synthetase (aaRS) that exhibit enhanced thermostability as well as optimal biological activity to aminoacylate/charge tRNA with unnatural amino acids (also referred to herein as a non-canonical amino acid or ncAA)). Briefly, the methods claimed herein comprise the following steps. First, aaRS homologs from various thermophilic (e.g., *Geobacillus stearothermophilus*) and mesophilic bacteria (e.g., *E. coli*) are evaluated to characterize/identify their activity and thermostability. Next, a series of chimeras are generated by hybridizing the sequences of a thermostable aaRS and its homolog that has high aminoacyl enzymatic activity. The chimeras are characterized to identify ones that exhibit higher thermostability as well as optimal biological activity, wherein the biological activity can be defined as the ability to aminoacylate tRNA. Also described herein are compositions of such chimeric bacterial TyrRSs (ChTyrRS), derived from *E. coli* TyrRS (EcTyrRS) and *Geobacillus stearothermophilus* TyrRS (GsTyrRS). The ChTyrRS show higher thermostability than EcTyrRS and higher activity than both GsTyrRS and EcTyrRS. ChTyrRSs tolerate Uaa-selective mutants better than EcTyrRS, affording higher solubility and activity relative to their wild-type counterparts. Thus, the ChTyrRS compositions described are more engineerable and useful for genetic code expansion (GCE).

In particular, the present invention encompasses compositions comprising a chimeric thermostable aminoacyl-tRNA synthetase derived from a nucleic acid sequence of a bacterial thermostable aminoacyl-tRNA synthetase hybridized to a nucleic acid sequence of its mesophilic bacterial aminoacyl-tRNA synthetase homolog. Thermostable microorganisms typically grow in the range of about 50 degrees C. to about 70-80 degrees centigrade. Mesophilic microorganisms typically grow in more physiological conditions at about 20 degrees centigrade to about 45 degrees centigrade.

A wide variety of thermal stable bacteria are known to those of skill in the art and can include, for example, *Geobacillus stearothermophilis, Bacillus stearothermophilis, Thermus thermophilis* or a *Thermoanaerobacter* species. Many mesophilic bacteria are also known to those skilled in the art and can include, for example, *Escherichia coli*, any *Staphylococcus* species, any *Streptococcus* species, or any *Pseudomonas* species. A particular embodiment of the present invention comprises a chimera wherein the relevant portion of the nucleic acid sequence of the thermostable bacteria is *Geobacillus stearothermophilis* is hybridized to the relevant portion of the nucleic acid sequence of the mesophilic bacteria is *Escherichia coli*. Selection of the relevant portion of the nucleic acid sequences of the individual components of the chimeric bacteria is determined as described herein using techniques known to those of skill in the art.

The chimeric compositions described herein also encompass chimeras comprising a mesophilic bacterial aminoacyl-tRNA synthetase (aaRS) that can be genetically engineered to incorporate one, or more, mutations/variations in its active site, resulting in the alteration of the substrate specificity of the aminoacyl-tRNA synthetase relative to the wild-type aminoacyl-tRNA synthetase (also referred to herein as variant chimeric thermostable aminoacyl-tRNA synthetases). These mutations/variations result in the ability of the aaRS to charge corresponding/cognate tRNAs with unnatural amino acids. The aaRS can be genetically engineered with the selected mutations prior to linkage/hybridization with the thermal stable aaRS. Alternatively. the aaRS can be engineered to incorporate an active site mutation after hybridization/linkage to its thermostable counterpart. The cognate tRNA can be the wild-type tRNA or can be genetically engineered to improve its activity as described in International Application No.: PCT/US2020/038766, the teachings of which are incorporated herein by reference. Importantly, as described herein, the chimeric aminoacyl-tRNA synthetases of the present invention exhibit increased thermostability relative to its individual wild-type mesophilic bacterial progenitor aaRS and higher biological activity (e.g., enhanced structural stability and/or increased solubility at physiological temperatures e.g., up to about 60° C., or increased ability to aminoacylate its cognate tRNA) relative to its individual wild-type thermophilic progenitor aaRS. Thus, the chimeras of the present invention have optimal thermostability and biological activity relative to their wild-type progenitor aminoacyl-tRNA synthetases to incorporate unnatural amino acids into mammalian proteins.

As described herein, the chimeric thermostable aminoacyl-tRNA synthetase of the present invention will have increased thermal stability relative to the mesophilic wild-type bacterial aaRS. The biological activity of the chimeric thermostable bacterial mesophilic aaRS can be defined as activity to aminoacylate/charge its cognate wild-type or variant tRNA with any of the known naturally occurring amino acids, or, if the chimera is a variant chimera, the activity to aminoacylate/charge its cognate tRNA with an unnatural amino acid.

The chimeric aminoacyl-tRNA synthetase variants of the present invention can have increased biological activity over the wild-type aminoacyl-tRNA synthetase to aminoacylate/charge its cognate wild-type or variant tRNA with an unnatural amino acid. Unnatural amino acids (Uaas) are known to those of skill in the art and can include analogs/derivatives of any of the naturally occurring amino acids. Some examples of Uaas of the present invention can include phenylalanine analogs such as p-benzoylphenylalanine (pBpA); tyrosine analogs such as O-methyltyrosine (OMeY); tryptophanyl analogs (5-azidotryptophan, 5-propargyloxytryptophan, 5-aminotryptophan, 5-methoxytryptophan, 5-O-allyltryptophan, or 5-bromotryptophan) or lysyl analogs. These analogs can be purchased from commercial sources (e.g., www.chemimpex.com) or synthesized by one of skill in the art using known methods (also see, for example, U.S. patent Ser. No. 10/717,975, the teachings of which are incorporated herein in their entirety).

A particular embodiment of the present invention is a composition of a chimera that comprises thermostable bacterial aminoacyl-tRNA synthetase GsTyrRS and the mesophilic bacterial aminoacyl-tRNA synthetase EcTyrRS. More specifically, a chimeric composition of the present invention (referred to herein as Ch2TyrRS-WT or ChTyrRS-H2) comprises the nucleic acid sequence which comprises SEQ ID NO:1, SEQ ID NO:41, or a nucleic acid sequence with at least 80% sequence identity to Seq ID NO: 1 or SEQ ID NO:41. or a nucleic acid sequence comprising about 80%, 85%, 86%, 87%, 88%, 89% 90%, 91%, 92%, 93%, 94%, 95%, 96%, 97%, 98%, or 99% sequence identity to SEQ ID NO:1 or SEQ ID NO:41. The amino acid sequence corresponding the this chimers is found in FIG. 15 as SEQ ID NO:42.

Alternatively, the chimeric composition (referred to herein as Ch6TyrRS-WT or ChTyrRS-H6) comprises the chimeric nucleic acid sequence SEQ ID NO:2, SEQ ID NO:45, or a nucleic acid sequence about 80%, 85%, 86%, 87%, 88%, 89% 90%, 91%, 92%, 93%, 94%, 95%, 96%, 97%, 98%, or 99% sequence identity to SEQ ID NO:2 or SEQ ID NO:45. The corresponding amino acid sequence is found in FIG. 15 as SEQ ID NO:46.

It is to be understood that all of the nucleic acid sequences and amino acid sequences described herein include corresponding sequences comprising about 80%, 85%, 86%, 87%, 88%, 89% 90%, 91%, 92%, 93%, 94%, 950%, 96%, 97%, 98%, or 99% sequence identity to the specific SEQ ID NO specifically named.

Further encompassed are variant chimeric thermostable aminoacyl-tRNA synthetases with mutations in the active site, for example, wherein the mutation in the active site results in the enzymatic activity for incorporation of an unnatural amino acid in a mammalian protein. In one embodiment the Uaa is a phenylalanine analog. In a particular embodiment the phenylalanine analog is p-benzoylphenylalanine (pBpA).

More particularly, the amino acid sequence of a chimeric thermostable aaRS that incorporates pBpA into a mammalian protein is referred to herein as Ch2TyrRS-pBpA and comprises SEQ ID NO:43 (with mutations in the active site Y37G, D179G, L183A), or an amino acid sequence with at least 80%, 85%, 86%, 87%, 88%, 89% 90%, 91%, 92%, 93%, 94%, 95%, 96%, 97%, 98%, or 99% sequence identity to SEQ ID NO:43.

Alternatively, the amino acid sequence of a chimeric thermostable aaRS that incorporates pBpA into a mammalian protein is referred to herein as Ch6TyrRS-pBpA and comprises SEQ ID NO: 47 (with mutations in the active site Y37G, D182G, L186A), or an amino acid sequence with at least 80%, 85%, 86%, 87%, 881%, 89% 90%, 91%, 92%, 93%, 94%, 95%, 96%, 97%, 98%, or 99% sequence identity to SEQ ID NO:46.

Also encompassed herein is an aaRS, wherein the mutation in the active site results in the incorporation of a tyrosine analog into a mammalian protein. More specifically, the tyrosine analog can be O-methyltyrosine (OMeY). The amino acid sequence of a chimeric thermostable aaRS that incorporates OMeY into a mammalian protein is referred to herein as Ch2TyrRS-poly and comprises SEQ ID NO:44 (with active site mutations Y37V, D176S, F180M, L183A), or an amino acid sequence with at least 80%, 85%, 86%, 87%, 88%, 89% 90%, 91%, 92%, 93%, 94%, 95%, 96%, 97%, 98%, or 99% sequence identity to SEQ ID NO:44.

Also encompassed by the present invention are cells (either cultured in vitro or in vivo) comprising a chimeric aaRS of the present invention. Such cells can also comprise the chimeric aaRS's cognate tRNA. Such cells can further comprise all cellular components required for translation of polynucleotides into proteins, including translation system components such as, for example, ribosomes, endogenous tRNAs, translation enzymes, mRNA and amino acids, resulting in the ability to produce proteins with naturally-occurring or unnatural amino acids incorporated therein.

The cells of the present invention can be any bacterial cell or eukaryotic cell suitable for use with the chimeric thermostable aaRS/tRNA, or chimeric thermostable aaRS variant/tRNA pairs described herein. For example, the cell can be selected from the group consisting of a yeast cell, insect cell or a mammalian cell. In particular, the bacterial cell is a genetically-engineered *E. coli* cell, or a homologous/analogous bacterial cell. More specifically, the *E. coli* is the ATMY series of strains as described herein.

Also encompassed by the present invention are methods of producing a chimeric thermostable aminoacyl-tRNA synthetase. The first step is to identify the suitable aaRS enzyme sequences to be linked as a chimera. For example, one skilled in the art can identify/evaluate an aminoacyl-tRNA synthetase of interest in a mesophilic microorganism (e.g., bacteria such as *E. coli*). The next step is to identify/evaluate a suitable aaRS homolog from a thermophilic microorganism with increased thermostability relative to the mesophilic microorganism aminoacyl-tRNA synthetase thermostability as described herein.

Once the suitable aaRS sequences are identified and characterized the chimera comprising the relevant sequences of the thermostable aminoacyl-tRNA synthetase and the mesophilic aminoacyl-tRNA synthetase can be constructed as described herein. The chimera can then be evaluated for thermostability and biological activity to aminoacylate/charge its cognate tRNA relative to its wild type progenitor aminoacyl-tRNA synthetases.

More specifically, as described herein, the technique of DNA shuffling was used to produce the chimeras of the present invention. DNA shuffling involves the digestion of a gene or homologous genes into random fragments, and the reassembly of those fragments into a full-length gene by PCR. The reassembled gene sequences are them evaluated/tested for thermophilic and enzymatic activity.

In a particular embodiment described herein, the mesophilic aaRS can be engineered to aminoacylate unnatural amino acid analogs, forming a variant chimeric thermostable aaRS with the enzymatic activity to charge/aminoacylate its cognate tRNA with the unnatural amino acid analog. The Uaa can be a phenylalanine analog, specifically, the phenylalanine analog is p-benzoylphenylalanine (pBpA). Alternatively, the Uaa is a tyrosine analog. More specifically, the tyrosine analog can be O-methyltyrosine (OMeY). Additional tyrosine analogs are known to those skilled in the art and can include, for example, sulpho-tyrosine, iodo-tyrosine, chloro-tyrosine and nitro-benzyl-tyrosine.

Also encompassed herein are methods of producing a protein in a cell with one, or more, unnatural amino acids at specified positions in the protein. The method comprises the following steps:

a. culturing the cell in a culture medium under conditions suitable for growth, wherein the cell comprises a nucleic acid that encodes a protein with one, or more, amber or opal selector codons, wherein the cell further comprises an Ec-tRNA$^{UAA}$ that recognizes the selector codon(s), and wherein the cell further comprises a chimeric thermostable aminoacyl-tRNA synthetase that preferentially aminoacylates the Ec-tRNA$^{UAA}$ with an unnatural amino acid;
b. contacting the cell culture medium with one, or more, unnatural amino acid analogs corresponding to the Uaa of the Ec-tRNA$^{UAA}$ under conditions suitable for incorporation of the one, or more, unnatural amino acids into the protein in response to the selector codon(s), thereby producing the protein with one, or more unnatural amino acids at specified positions of the protein.

In particular, the methods can comprise any of the chimera thermostable aminoacyl-tRNA synthetases described herein. In particular, the chimera can comprise the nucleic acid sequence SEQ ID NO:1 or SEQ ID NO:41, or a nucleic acid sequence with at least 80% sequence identity to SEQ ID NO: 1 or SEQ ID NO:41, or the nucleic acid sequence SEQ ID NO:2 or SEQ ID NO:45, or a nucleic acid sequence with at least 80% sequence identity to SEQ ID NO: 2, or SEQ ID NO:45.

In one embodiment, the unnatural amino acid to be incorporated into the protein is p-benzoylphenylalanine (pBpA) and the chimera is Ch2TryRS-pBpA or Ch6TryRS-pBpA, wherein the amino acid sequence of the Ch2TryRS-pBpA chimera comprises SEQ ID NO:43 or SEQ ID NO: 47, or an amino acid sequence with at least 80% sequence identity to either SEQ ID NO: 43 or SEQ ID NO:47.

In another embodiment, the unnatural amino acid to be incorporated into the protein is unnatural amino acid O-methyltyrosine (OMeY) and the chimera is Ch2TyrRS-poly, wherein the Ch2TyrRS-poly chimera comprises SEQ ID NO:44, or an amino acid sequence with at least 80% sequence identity to either SEQ ID NO:44.

The cell can be an *E. coli* cell or a eukaryotic cell. In one embodiment the eukaryotic cell is a mammalian cell. In another embodiment, the *E. coli* is an ATMY *E. coli* strain.

Further, the present invention covers kits for producing a protein in a cell, wherein the protein comprises one, or more Uaa incorporate into the protein. For example, wherein the protein comprises one, or more pBpA residues, the kit comprises a container containing a polynucleotide sequence encoding an Ec-tRNA$^{pbpa}$ that recognizes an amber or opal selector codon(s) in a nucleic acid of interest in the cell; and a container containing a polynucleotide sequence encoding the chimeric thermostable aminoacyl-tRNA synthetase Ch2TryRS-pBpA or Ch6TyrRS-pBpA.

The polynucleotide encoding the chimera encodes the amino acid sequence of the chimera comprising SEQ ID NO:43 or SEQ ID NO:47, or an amino acid sequence with at least 80% sequence identity to either SEQ ID NO:43 or SEQ ID NO:47. The kit can further comprise one, or more, p-benzoylphenylalanine molecules. and instructions for producing the protein.

Alternatively, the kit can be used for producing a protein in a cell, wherein the protein comprises one, or more O-methyltyrosine (OMeY) residues. The kit can include a container containing a polynucleotide sequence encoding an Ec-tRNA$^{poly}$ that recognizes an amber or opal selector codon(s) in a nucleic acid of interest in the cell, and a container containing a polynucleotide sequence encoding the chimeric thermostable aminoacyl-tRNA synthetase Ch2TyrRS-poly.

The polynucleotide encoding the chimera encodes the amino acid sequence SEQ ID NO:44, or an amino acid sequence comprising at least 80% sequence identity to SEQ ID NO:44. The kit can further comprise one, or more, O-methyltyrosine (OMeY) molecules, and instructions for producing the protein.

The current invention demonstrates features and advantages that will become apparent to one of ordinary skill in the art upon reading the following Description of the Drawings and Detailed Description.

BRIEF DESCRIPTION OF THE DRAWINGS

FIGS. 1A-1C show that engineered TyrRS mutants show lower thermostability. A) EcTyrRS active site, showing bound tyrosine in magenta, and highlighting mutated residues in engineered variants (shown below). B) Western blot analysis of soluble and insoluble fractions of *E. coli* cell free extract expressing EcTyrRS-WT and EcTyrRS-pBpA reveals that the latter is largely insoluble. C) Thermal shift assay of various TyrRS variants. Dot-blot was performed (using an anti-polyhistidine antibody) on the soluble fraction of *E. coli* cell-free extracts expressing the indicated TyrRS variants (left), after incubation at the indicated temperature (top).

FIGS. 4A and 4B show that chimeric TyrRS derived mutants exhibit improved activity for ncAA incorporation in mammalian cells. A) TyrRS-pBpA variants were co-expressed in HEK293T cells with $tRNA_{CUA}^{Tyr}$ and EGFP-39-TAG, in the presence and absence of pBpA, and the expression of the full-length reporter was monitored by its characteristic fluorescence in cell-free extract. The expression level was reported as the % of an identical experiment where wild-type EGFP reporter (no TAG) was used as the reporter. B) The ncAA-incorporation efficiency of Ch2TyrRS-Poly is comparable to the highly active EcTyrRS-Poly. Activity was measured as described in section (A) in the presence and absence of 1 mM OMeY. See FIG. 9 for all associated fluorescence images. FIG. 4C shows that the ChTyrRS-pBpA show enhanced activity relative to either wild-type counterparts. Activity was measured by expressing a GFP-151-TAG reporter in *E. coli* cells in the presence of tRNA-EcTyr (TAG suppressor).

FIG. 5 shows the nucleic acid sequences of ChTyrRS-H2 (SEQ ID NO:1) and ChTyrRS-H6 (SEQ ID NO:2).

Figures 2A, 2B, 2C:
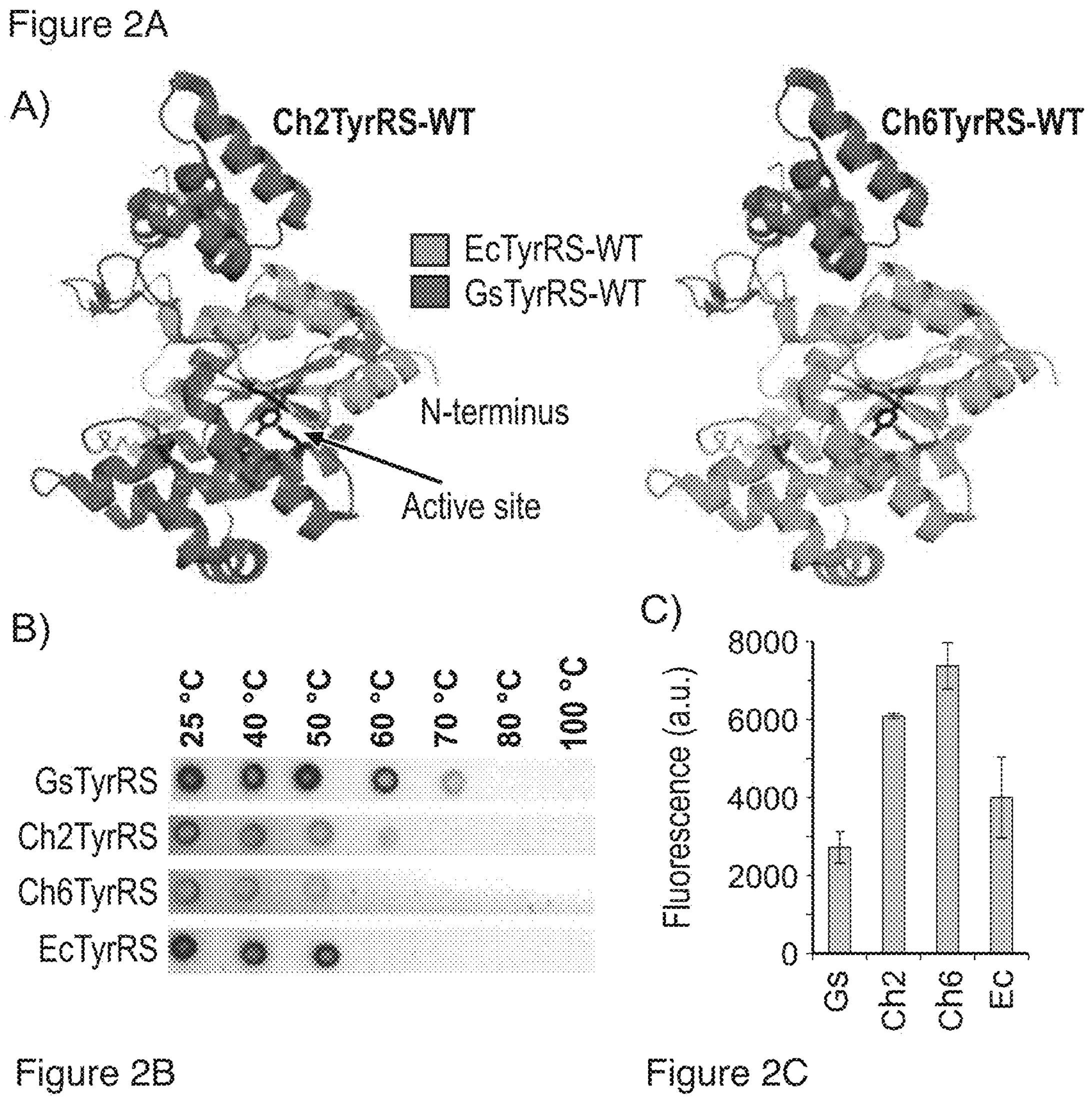
FIGS. 2A-2C show that bacterial TyrRS chimeras created from GsTyrRS and EcTyrRS exhibit higher activity and intermediate thermostability. A) Two chimeras, Ch2TyrRS and Ch6TyrRS, created by fusing EcTyrRS (green) and GsTyrRS (magenta) sequences. The EcTyrRS crystal structure was used to highlight the progenitor sequences in the two chimeras. B) Thermal shift assay of the two chimeras, as well as their wild-type progenitors, in *E. coli* cell-free extract. Dot-blot was performed (using an anti-polyhistidine antibody) on the soluble fraction of *E. coli* cell-free extracts expressing the indicated TyrRS variants (left), after incubation at the indicated temperature (top). C) Activity of the TyrRS variants in ATMY *E. coli* strains, measured using the expression of sfGFP-151TAG reporter in the presence of $tRNA_{CUA}^{Tyr}$. Characteristic fluorescence of the full-length sfGFP-151-TAG reporter was measured in resuspended cells.

The text of the final plasmid maps and sequences are provided below with the following color coding: aaRS highlighted red, antibiotic selectable marker highlighted blue, tRNA highlighted purple, lacI highlighted green, and the origin of replication highlighted orange. The images are not color coded.

FIG. 12 shows the plasmid map and sequences of pBK MCS GsYRS WT and where the active site mutations are located in Ch2TyrRS-pBpA variant, and also where the active site mutations are located in the Ch6TyrRS-pBpA variant. (SEQ ID NOS 31, 1 and 2), respectively, in order of appearance).

FIG. 13 shows the plasmid map and sequences of pET22b 10×N-term His GsYRS (SEQ ID NOS 32-36, respectively, in order of appearance).

FIG. 14 shows the plasmid map and sequences of pBIU Gs-BPA-RS and where the active site mutations are located in the Ch2YyrRS-OMeY variant. (SEQ ID NOS 37-40, respectively, in order of appearance).

FIG. 15 shows the following sequences in order of appearance:

Ch2TyrRS-WT nucleotide sequence (SEQ ID NO: 41) and its encoded amino acid sequence (SEQ ID NO: 42).

Ch2TyrRS-pBpA amino acid SEQ ID NO: 43. Mutations are highlighted in red: Y37G, D179G, L183A.

Ch2TyrRS-poly amino acid SEQ ID NO: 44. Mutations are highlighted in red; Y37V, D176S, F180M, L183A.

Ch6TyrRS-WT nucleotide sequence (SEQ ID NO: 45) and its encoded amino acid sequence (SEQ ID NO: 46).

Ch6TyrRS-pBpA amino acid SEQ ID NO: 47. Mutations are highlighted in red: Y37G, D182G, L186A.

DETAILED DESCRIPTION OF THE PREFERRED EMBODIMENTS

While this invention has been particularly shown and described with references to preferred embodiments thereof, it will be understood by those skilled in the art that various changes in form and details may be made therein without departing from the scope of the invention encompassed by the appended claims.

Non-canonical amino acid (ncAA) mutagenesis of proteins in living cells has emerged as a powerful technology with enormous potential.[1-5] A ncAA of interest can be co-translationally incorporated using an orthogonal aminoacyl-tRNA synthetase (aaRS)/tRNA pair in response to a nonsense or frameshift codon.[1-5] Central to this technology is the ability to engineer the substrate specificity of a natural aaRS through directed evolution. Many useful ncAAs have been genetically encoded in *E. coli* using the *Methanocaldococcus jannaschii* derived tyrosyl-tRNA synthetase (MjTyrRS)/tRNA pair, including those containing bioconjugation handles, photo-affinity probes, biophysical probes, models for natural post-translational modification, etc.[1, 2, 5] While some of these functionalities can also be genetically encoded using other aaRS/tRNA pairs, several others (e.g., those modeling natural post-translational modifications) are reliant on the unique architecture of the TyrRS active site.[1, 2, 5] Unfortunately, however, this enabling toolset cannot be used in eukaryotic cells, as the archaea-derived MjTyrRS/tRNA pair cross-reacts with its eukaryotic counterpart. Typically, bacteria-derived aaRS/tRNA pairs are suitable for ncAA incorporation in eukaryotes, as they tend to be orthogonal in these cells.[1, 3, 5-7] Indeed, the *E. coli* derived tyrosyl-tRNA synthetase (EcTyrRS)/tRNA pair has been established for ncAA incorporation in eukaryotic cells.[8-12] It was first engineered to incorporate ncAAs into proteins expressed in eukaryotic cells nearly two decades ago. Yet, the ncAA-toolbox developed using this pair remains surprisingly limited, particularly when compared to the remarkable success of the MjTyrRS/tRNA pair during the same time period.[1-3, 5, 13] The ability to recapitulate the success of the MjTyrRS/tRNA platform using a bacterial TyrRS/tRNA pair will significantly expand the scope of the genetic code expansion (GCE) technology in eukaryotes by providing access to structurally unique ncAAs that are challenging to genetically encode using alternative aaRS/tRNA pairs.

The limited success of the EcTyrRS/tRNA pair can be, at least partially, attributed to the challenges associated with the directed evolution platform used to alter its substrate specificity.[1, 3, 7, 13] Unlike MjTyrRS, which can be readily engineered using a facile *E. coli* based directed evolution system, a more cumbersome yeast-based selection scheme is needed to engineer EcTyrRS.[8] To address this challenge, a novel strategy was developed that involves the development of unique *E. coli* strains (ATMY strains), where the endogenous EcTyrRS/tRNA pair is functionally substituted with an archaeal counterpart.[1, 3, 7, 13] (see also U.S. patent Ser. No. 10/717,975). It was demonstrated that such strains can be generated without incurring a significant growth penalty.[13] The 'liberated' EcTyrRS/tRNA pair can be subsequently established in the resulting ATMY strains as an orthogonal nonsense suppressor. This has enabled the use of the facile *E. coli* based directed evolution platform to engineer the substrate specificity of EcTyrRS.[13]

Figure 6:
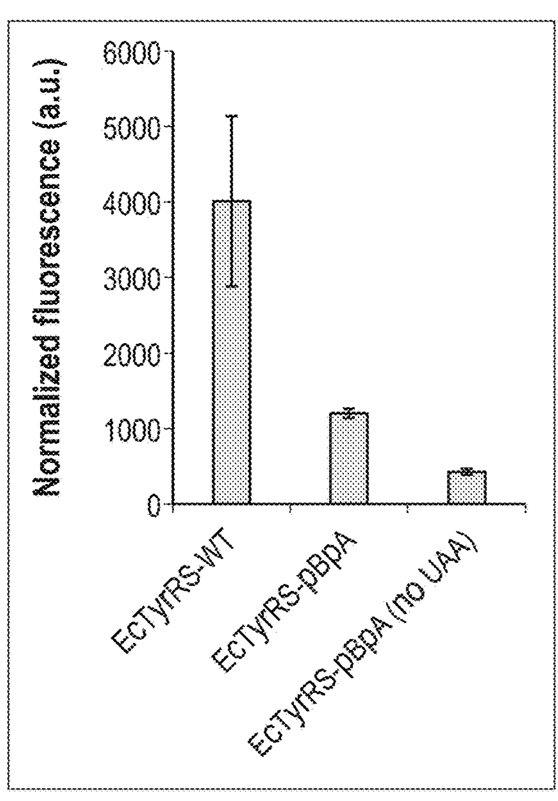
FIG. 6 shows that the activity of EcTyrRS-pBpA is significantly weaker than EcTyrRS-WT. Activity was evaluated using the sfGFP-151-TAG reporter, expressed in ATMY *E. coli*, by measuring the characteristic fluorescence of the full-length reporter in resuspended cells. For EcTyrRS-pBpA, the expression was measured in the presence or absence of 1 mM pBpA.

Although the ability to rapidly engineer the EcTyrRS/tRNA pair using this facile directed evolution platform has provided access to several new ncAAs, in some instances, the resulting engineered mutants demonstrated poor activity. For example, it was attempted to develop an EcTyrRS mutant that efficiently charges p-benzoylphenylalanine (pBpA), a powerful photoaffinity probe that has been useful for capturing weak and transient molecular interactions.[8, 14-17] Even though EcTyrRS was previously engineered using the yeast-based selection platform to selectively charge pBpA, the utility of this mutant has been limited due to its weak activity. When a large EcTyrRS active site mutant library was subjected to the facile selection system, the same mutant was identified that was previously developed by selection in yeast. This indicated that the observed set of mutations indeed optimally recodes the EcTyrRS active site for charging pBpA. The activity of this pBpA-selective EcTyrRS was somewhat low, as measured in the ATMY *E. coli* strain using the sfGFP-151-TAG reporter (FIG. 6). A systematic investigation identified that the EcTyrRS-pBpA mutant was largely insoluble in *E. coli*, potentially explaining its poor activity (FIG. 1B). Western blot analysis of the soluble and insoluble fractions of cell-free extracts of *E. coli* expressing polyhistidine-tagged EcTyrRS-WT and EcTyrRS-pBpA revealed that the latter is nearly exclusively found in the insoluble fraction (FIG. 1B). In contrast, a large portion of the wild-type EcTyrRS was found in the soluble fraction.

It has been previously observed that when a protein is subjected to directed evolution to attain an altered function, the stability of the resulting mutants is often compromised.[18-21] Consequently, the extent to which a protein can be engineered is often limited by how stable it is. It was hypothesized that the success in engineering MjTyrRS, an enzyme derived from a thermophilic archaeon, is likely facilitated by its high structural stability. In contrast, EcTyrRS, derived from mesophilic bacteria, may be a less stable scaffold and have a lower tolerance for active site mutations. To test this notion, a modified cellular thermal shift assay (CETSA) was utilized.[22, 23] In this assay, cell-free extract expressing a target protein is heated to increasing temperatures, and the amount of remaining protein in the soluble fraction is subsequently tested by immunoblotting. The temperature range at which a protein is lost from the soluble fraction provides an estimate of its thermostability. In addition to EcTyrRS-WT and EcTyrRS-pBpA, a polyspecific EcTyrRS mutant (EcTyrRS-Poly) was also tested that is highly active (FIG. 1A). For comparison, MjTyrRS-WT was include, as well as two of its comparable engineered mutants: one selective for pBpA (MjTyrRS-pBpA),[24] and another that exhibits ncAA polyspecificity (MjTyrRS-Poly)

Figure 7:
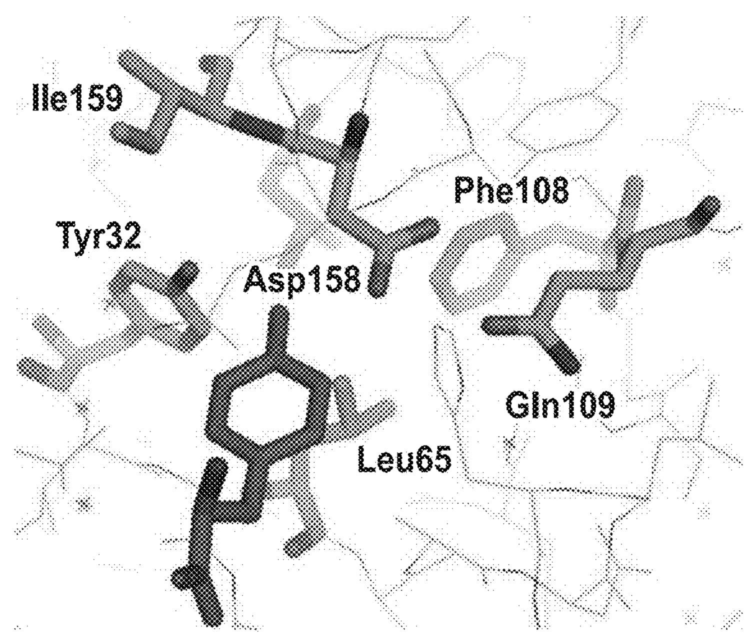
FIG. 7 shows the MjTyrRS mutants used in this study. The active site structure of MjTyrRS is also shown highlighting the key residues mutated to generate non-canonical amino acids (ncAA or Uaa)-selective variants.

(FIG. 7).[25] All of these proteins encoded an N-terminal hexahistidine tag (SEQ ID NO: 3) to facilitate their detection in a dot-blot assay using an anti-polyhistidine antibody. As expected, MjTyrRS was found to be highly thermostable, maintaining solubility up to 80° C. (FIG. 1C). In contrast, EcTyrRS was much less stable, and was lost from the soluble fraction between 50° C. and 60° C. (FIG. 1C). These values are consistent with previously reported thermostability measurements.[26] All of the engineered mutants exhibited reduced stability relative to their wild-type counterparts. MjTyrRS-pBpA mutant was slightly less stable than its polyspecific counterpart, but both were soluble at physiological temperature. In contrast, for EcTyrRS, only the polyspecific mutant was soluble at physiological temperature; the pBpA selective mutant was not detected in the soluble fraction even at the lowest temperature tested (FIG. 1C). These observations support the hypothesis that the lower stability of EcTyrRS negatively impacts its engineerability. While some of its active site mutants, such as EcTyrRS-Poly, are adequately stable and active under physiological conditions, more destabilizing mutants such as EcTyrRS-pBpA are not viable.

Figure 8:
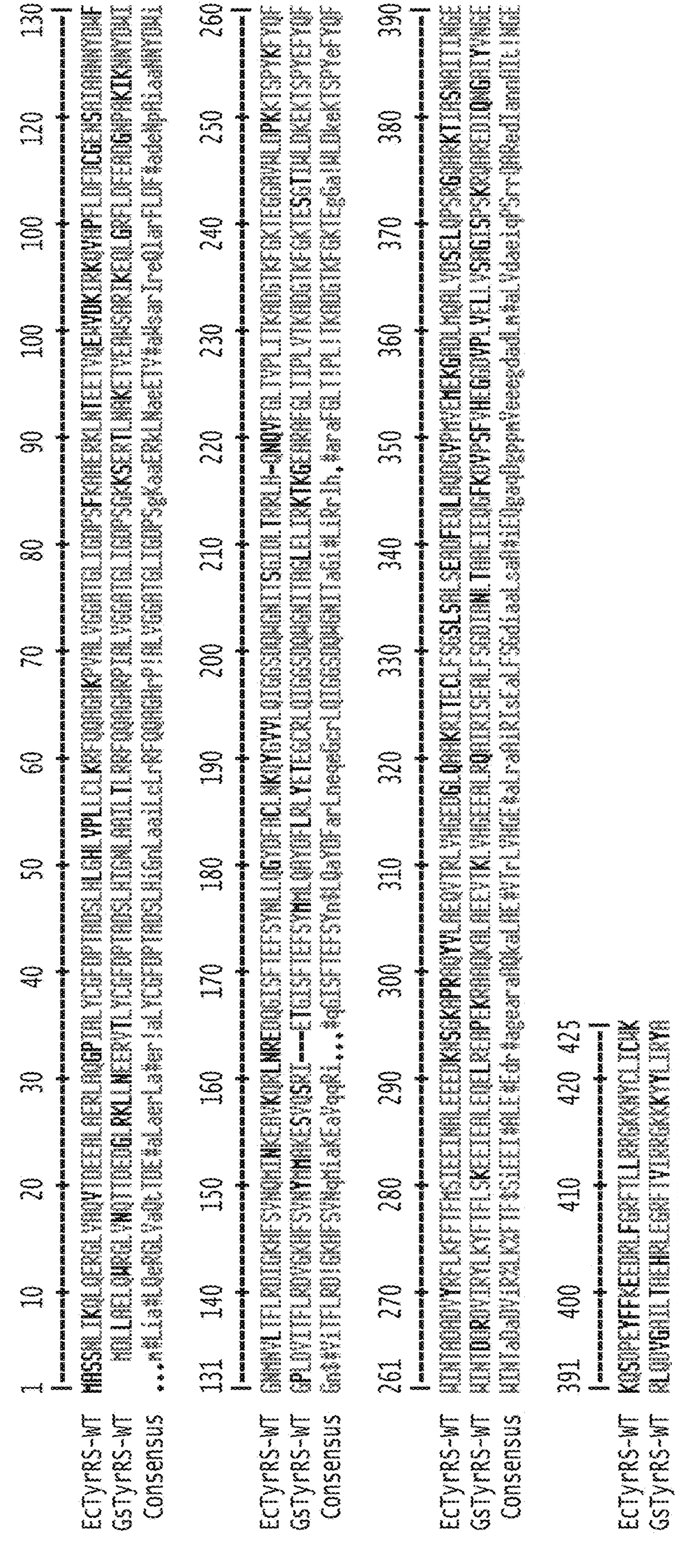
FIG. 8 shows the sequence alignment of EcTyrRS-WT (SEQ ID NO: 29) and GsTyrRS-WT (SEQ ID NO: 30) and its consensus sequence.

To overcome this challenge, the possibility of adapting a TyrRS from a thermophilic bacterium was considered, which might offer a higher degree of engineerability relative to EcTyrRS. Several aminoacyl-tRNA synthetases derived from the thermophilic bacterium *Geobacillus stearothermophilus* have been purified and structurally characterized.[27-29] TyrRS from this bacterium (GsTyrRS) is homologous to EcTyrRS (FIG. 8) but is significantly more thermostable, offering an attractive scaffold for engineering ncAA-selective mutants.[26] The stability and the activity of GsTyrRS was tested using the CETSA and the sfGFP-151-TAG expression assay, as described above (FIG. 2B). GsTyrRS was indeed significantly more stable than EcTyrRS, but its activity was somewhat lower in *E. coli* (FIGS. 2B, 2C). It was previously investigated whether enzymes derived from thermophilic bacteria exhibit weaker activity at lower temperature.[30]

A chimera from EcTyrRS and GsTyrRS was then constructed that exhibited an optimal balance of stability and activity. It has been previously shown that such chimeric enzymes can be excellent scaffolds for protein engineering.[31, 32] As described herein, the technique of DNA shuffling was used to produce the chimeras of the present invention. Briefly, DNA shuffling involves the digestion of a gene or homologous genes into random fragments, and the reassembly of those fragments into a full-length gene by PCR. The gene fragments prime on each other based on sequence homology, and recombination occurs when fragments from one copy of a gene anneal to fragments from another copy, causing a template switch, or crossover event. As described herein, naturally occurring homologous genes such as aminoacyl-tRNA synthetases from mesophilic and thermophilic microorganisms are used as the progenitor sources for the hybrids. The gene(s) are digested/cut into random segments with appropriate restriction enzymes to fragments of about 100 to 300 base pairs long. The segments are then reassembled by using a suitable a DNA polymerase with overlapping segments or by using some version of overlap PCR (see for example, Sheryl B. Rubin-Pitel, et. al., in Bioprocessing for Value-Added Products from Renewable Resources, 2007; H. Kamada, S.-I. Tsunoda, in Biomaterials for Cancer Therapeutics, 2013; David P. Clark, Nanette J Pazdernik, in Biotechnology (Second Edition), 2016). The resulting constructs can then be sequenced and evaluated for the desired characteristics using known protocols.

Figures 3A, 3B:
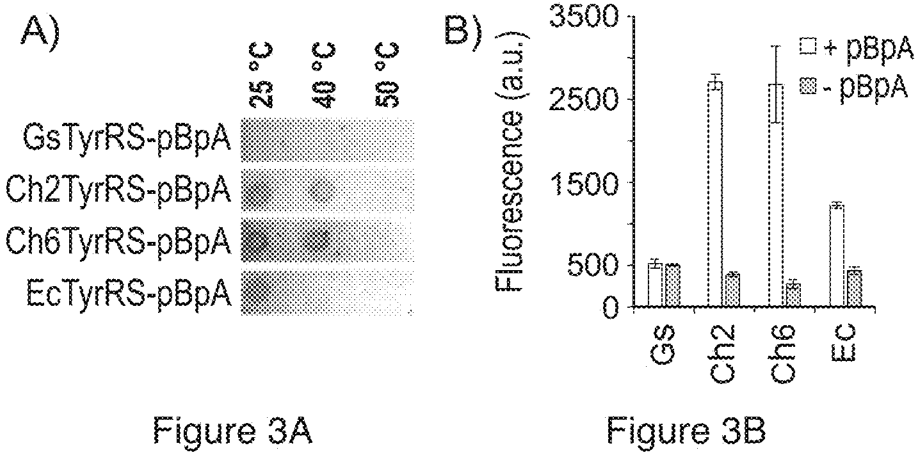
FIGS. 3A-3B show that chimeric TyrRS variants better tolerate pBpA-selective mutations. A) Thermal shift assay of the pBpA selective TyrRS mutants constructed from the two wild-type or chimeric scaffolds, in *E. coli* cell-free extract. Dot-blot was performed (using an anti-polyhistidine antibody) on the soluble fraction of *E. coli* cell-free extracts expressing the indicated TyrRS-pBpA variants (left), after incubation at the indicated temperature (top). B) Activity of the TyrRS-pBpA variants in the ATMY *E. coli* strain, measured using the expression of sfGFP-151TAG reporter in the presence of $tRNA_{CUA}^{Tyr}$ and in the presence and absence of 1 mM pBpA. Characteristic fluorescence of the full-length sfGFP-151-TAG reporter was measured in resuspended cells.

Several chimeras were constructed and tested between EcTyrRS and GsTyrRS and two were identified, Ch2TyrRS and Ch6TyrRS (FIG. 2A), which show higher levels of activity (FIG. 2C) and intermediate thermostability (FIG. 2B) relative to their wild-type progenitors, when expressed in ATMY *E. coli*. Next, pBpA-selective mutants of these TyrRS variants were generated and tested. Both Ch2TyrRS-pBpA and Ch6TyrRS-pBpA were more thermostable than EcTyrRS-pBpA and were also soluble at physiological temperature (FIG. 3A). This was reflected by the significantly higher degree of activity observed for these enzymes (FIG. 3B). Interestingly, even though GsTyrRS was the most thermostable, the corresponding pBpA-selective mutant was found to be largely insoluble and poorly active when expressed in *E. coli* (FIG. 3A, 3B). While the basis of this observation is unclear, it indicates that the chimeras may be better suited for engineering new ncAA-selective variants.

Figures 4A, 4B:
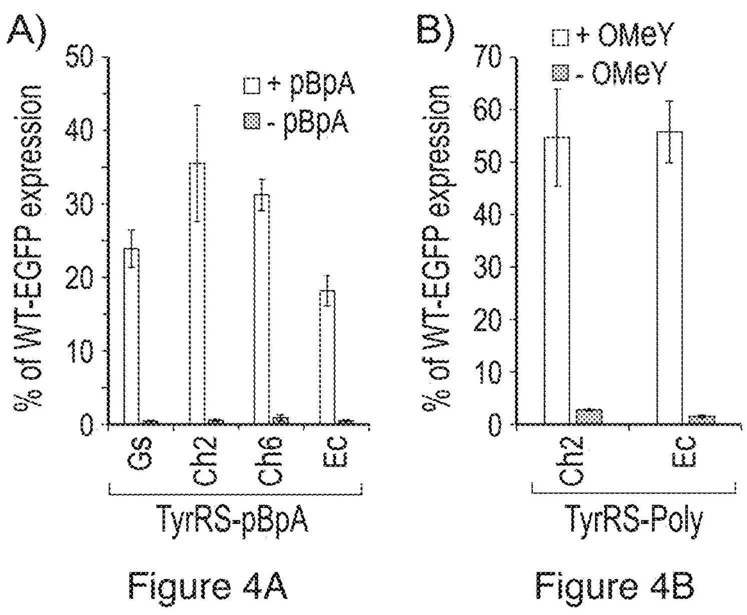
FIGS. 4A-4C.
Figure 4C:
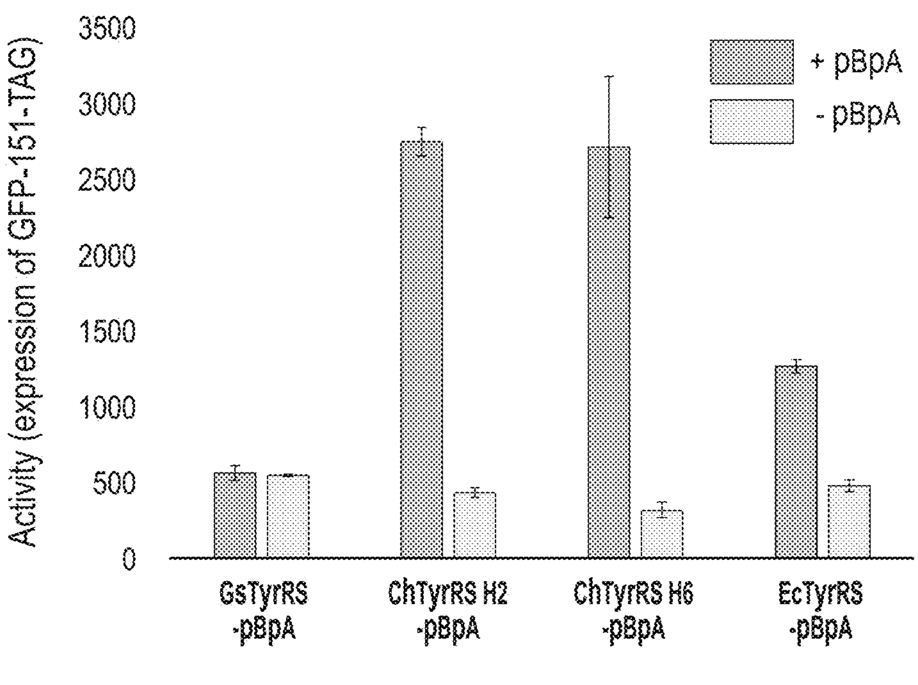
Figure 9:
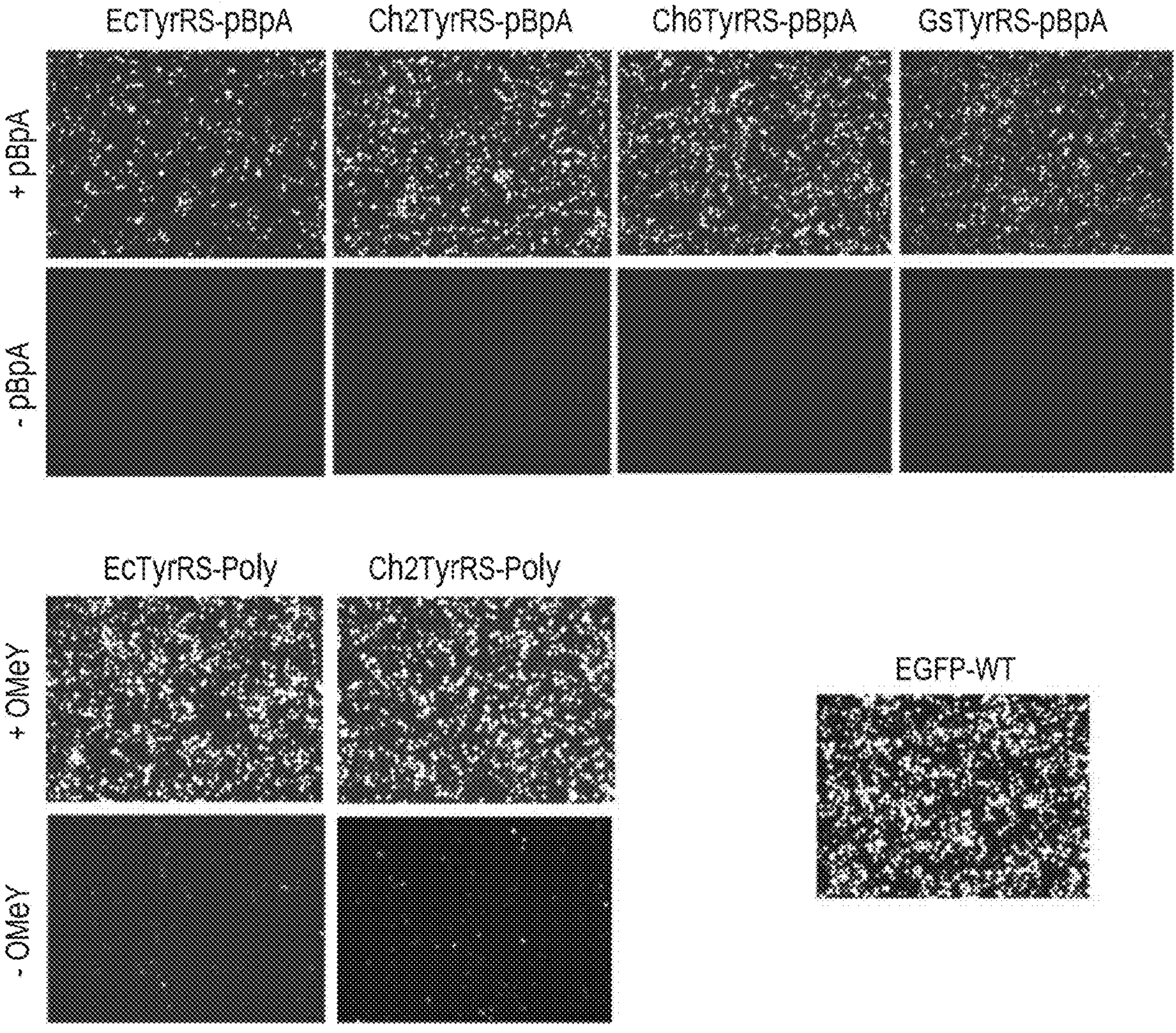
FIG. 9 shows the fluorescence images of mammalian cells expressing EGFP-39-TAG reporter using various TyrRS/tRNA pairs (shown above), in the presence or absence of relevant ncAAs (left). These images correspond to the fluorescence values presented in FIG. 4.
Figure 10:
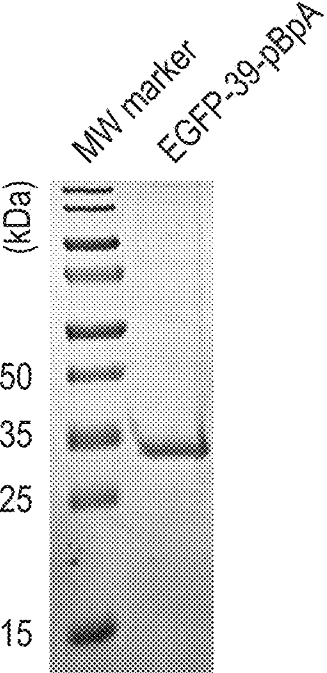
FIG. 10 shows SDS-PAGE analysis of the EGFP-39-pBpA reporter expressed in HEK293T cells using Ch2TyrRS-pBpA.
Figure 11A:
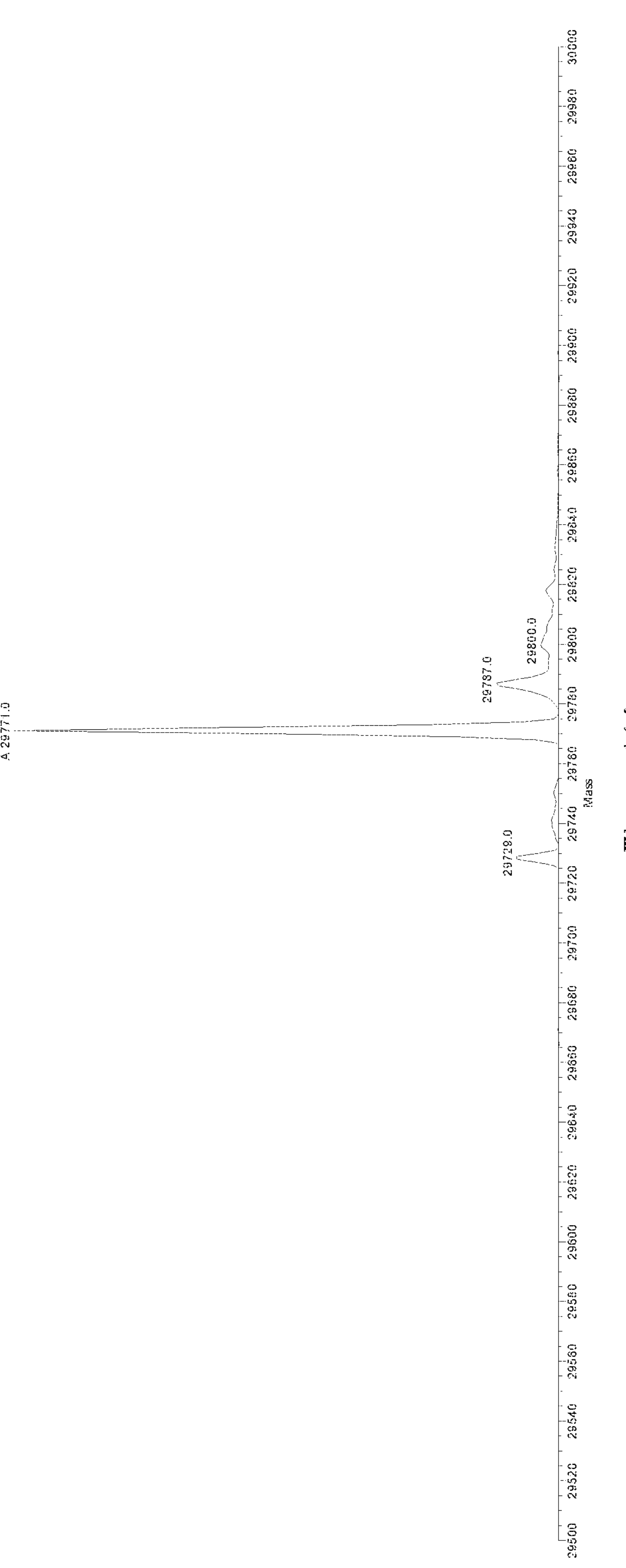
FIGS. 11A-B show the deconvoluted ESI-MS analysis of EGFP-39-pBpA reporter expressed in HEK293T cells using Ch2TyrRS-pBpA. Two different magnifications of the same spectra are shown. The major species (29771 Da) corresponds to the expected mass; 29729 Da peak likely represents the same species lacking N-terminal acetylation (−42 Da), while 29787 Da peak likely arises from oxidation (+16 Da).
Figure 11B:
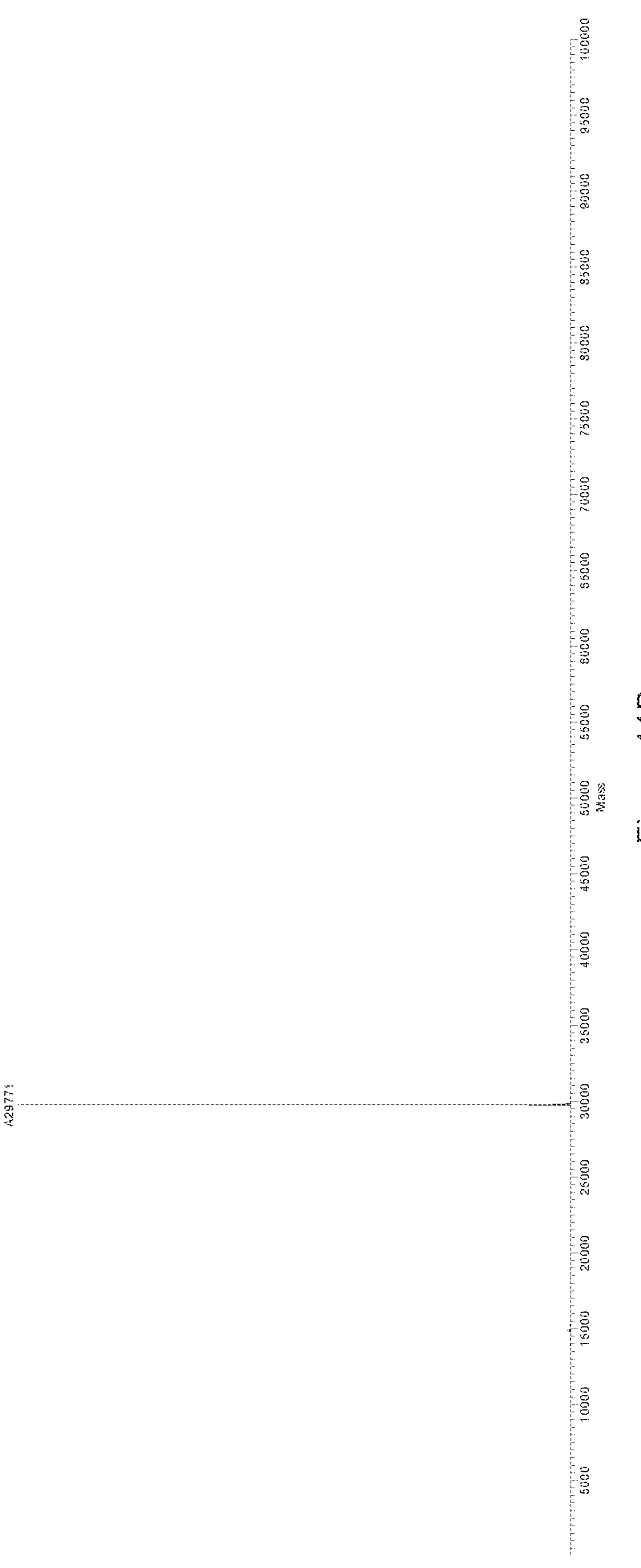

The activity of these engineered pairs was evaluated in the ATMY *E. coli* strain, where it is significantly easier to control parameters affecting the assay performance, such as the expression level of the aaRS/tRNA pairs. To demonstrate the utility of these new tools in eukaryotic cells, the activity of the pBpA-selective TyrRS variants were tested in HEK293T cells. EcTyrRS-pBpA, GsTyrRS-pBpA, Ch2TyrRS-pBpA, and Ch6TyrRS-pBpA were each cloned into a mammalian expression vector under a UbiC promoter, which also encodes 16 copies of the $tRNA^{Tyr}_{CUA}$ expression cassette. The resulting plasmids were co-transfected into HEK293T cells with another plasmid encoding an EGFP-39-TAG reporter, and the full-length reporter expression was monitored in the presence or absence of 1 mM pBpA in the media (FIG. 4A, and FIG. 9). Expression of a wild-type EGFP reporter (no in-frame TAG codon) was also included as a control. All four TyrRS-pBpA variants enabled successful incorporation of pBpA into the reporter. However, Ch2TyrRS-pBpA and Ch6TyrRS-pBpA demonstrated significantly higher activity (up to 36% of wild-type EGFP) relative to EcTyrRS-pBpA and GsTyrRS-pBpA (FIG. 4A). The reporter protein expressed using Ch2TyrRS-pBpA was isolated using Ni-NTA affinity chromatography and characterized by SDS-PAGE (FIG. 10) and mass-spectrometry analysis (FIGS. 11A-B) to confirm successful pBpA incorporation. It is worth noting that the activity of GsTyrRS-pBpA in mammalian cells was found to be significantly higher than what is expected from its assessment in ATMY *E. coli*, where it was found to be nearly inactive. It is possible that the more sophisticated protein folding machinery of the mammalian cells is able to better process unstable engineered proteins like GsTyrRS-pBpA. The TyrRS variants are also expressed more strongly in mammalian cells than in *E. coli*, which may also contribute to the observed difference.

Nonetheless, these results demonstrate that the chimeric TyrRS variants provide improved platforms for the GCE technology in eukaryotes. To further highlight the generality of this approach, Ch2TyrRS-Poly was constructed by introducing previously reported active site mutations for generating EcTyrRS-Poly (FIG. 1A), an engineered mutant that charges several different ncAAs including O-methyltyrosine (OMeY). When tested in HEK293T cells, both EcTyrRS-Poly and Ch2TyrRS-Poly exhibited comparable activity for EGFP-39-TAG reporter expression (FIG. 4B and FIG. 9), confirming that the chimeric TyrRS is able to recapitulate the activity of well-behaved bacterial engineered EcTyrRS mutants, while providing a better scaffold for those with suboptimal stability.

Work in the last two decades have provided a deep insight into how the biophysical properties of a protein influence its evolution.[18-21] It is now clear that the function-altering mutations acquired during experimental or natural evolution can often negatively impact the structural stability of a protein. The work described herein highlights its impact on the GCE technology, which relies on engineered aaRSs that selectively charge ncAAs of interest. The structural robustness of MjTyrRS has been shown and has contributed to its remarkable success as a powerful GCE platform. In contrast, the lower stability of EcTyrRS compromises the extent to which its active site can be altered. It is important to note that the same limitation likely affects the engineerability of several other aaRS/tRNA pairs, derived from mesophilic organisms (e.g., *E. coli* or yeast),[3, 6, 33-35] which have been adapted for ncAA incorporation. Indeed, the success of engineering these platforms for ncAA incorporation has been limited. As a result of the work described herein, a strategy to overcome this challenge by taking advantage of more thermostable aaRS homologs derived from thermophilic organisms is now available.

The chimeras generated from thermophilic and mesophilic aaRS homologs may be even better suited for this purpose. Analogous strategies have been used to create optimal starting points for the directed evolution of enzymes such as cytochrome P450.[31] It is possible that instead of simple aaRS chimeras like the ones reported here, more sophisticated counterparts with even better properties can be created by constructing and selecting a DNA-shuffling library of EcTyrRS and GsTyrRS. Additionally, as shown herein, the relative performance of the same aaRS in different expression systems can be different. For example, the GsTyrRS-pBpA mutant, which is largely insoluble and inactive in *E. coli*, demonstrated robust activity in mammalian cells. This might stem from differences in protein folding machinery in different host cells, as well as other factors such as variable expression level of the aaRS, speed of translation, codon usage, etc.

In summary, here is established the structural robustness of an aaRS as an important factor that significantly impacts its engineerability for GCE. A roadmap for creating more engineerable bacterial aaRS variants by hybridizing homologs from mesophilic and thermophilic bacteria is provided. Mutants generated from such chimeric TyrRSs show robust activity in both ATMY *E. coli* strain as well as in mammalian cells, suggesting that these are more attractive scaffolds for extensive engineering. Directed evolution of these using the facile ATMY *E. coli* based selection system should provide access to new enabling ncAAs. Finally, improved pBpA-incorporation activity of ChTyrRS-pBpA will further facilitate the application of this important photo-crosslinker ncAA for uncovering new biomolecular interactions in eukaryotic cells.

Without further elaboration, it is believed that one skilled in the art can, based on the above description, utilize the present invention to its fullest extent. The following specific embodiments and examples are, therefore, to be construed as merely illustrative, and not limitative of the remainder of the disclosure in any way whatsoever.

EXAMPLES

The following examples are provided to illustrate embodiments of the present invention but are by no means intended to limit its scope. The examples described herein will be understood by one of ordinary skill in the art as exemplary protocols. One of ordinary skill in the art will be able to modify these procedures appropriately and as necessary.

Introduction

The present invention describes the composition of thermostable bacteria-derived TyrRS variants that can be more aggressively engineered for Uaa incorporation than their wild-type counterparts. The invention is not restricted to TyrRS, however; the method to generate such active and thermostable mutants, which is described as a part of this invention, can also be readily extended to all other bacteria-derived aaRSs that can be engineered for Uaa incorporation in eukaryotic cells.

The work described herein with *E. coli* derived TyrRS (EcTyrRS) has revealed that many of the engineered mutants that have already been developed show poor folding and stability in cells. Expression of these mutants followed by analysis of the soluble and insoluble fractions of the proteome by Western blot reveals the majority of the mutant proteins are insoluble. Further analysis using CETSA (Cellular Thermal Stability Assay) show that the EcTyrRS is not as thermostable as its archaea derived counterpart that has been successfully engineered to incorporate numerous Uaas in bacteria. Furthermore, it has been found that the mutants derived from the archaeal TyrRS are also less stable than their wild-type counterpart, but still sufficiently viable at the physiological temperature, highlighting the importance of having a thermostable wild-type aaRS for developing Uaa-selective mutants.

To overcome the poor thermostability of EcTyrRS, a homologous TyrRS from the thermophilic bacteria *Geobacillus stearothermophilus* (GsTyrRS) was identified and evaluated. Although GsTyrRS was more stable, it exhibited significantly lower activity relative to EcTyrRS. This was not unexpected, as the stability and activity of enzymes are often negatively correlated.

The present invention describes a method to generate chimeric aaRS mutants that demonstrate optimal balance between thermostability and activity. By generating a chimera between two homologous aaRS—one highly active but less stable, and the other highly stable (from a thermophile such as *Geobacillus stearothermophilus*)—it is possible to create chimeras that exhibit such optimal properties. For example, by generating chimeras between EcTyrRS and GsTyrRS, novel sequences have been generated that are still significantly more stable than EcTyrRS yet have higher activity in both bacterial and eukaryotic cells. Such chimeras can be generated either by rational fusion of homologous stretches, or by DNA shuffling of the thermostable and the active aaRS sequences.

The method described in this invention for creating stable yet active bacterial aaRS variants is not restricted to any one particular aaRS. The same strategy can be applied to generate optimal chimeric variants of any other bacterial aaRS including, but not limited to, those charging alanine, glycine, serine, cysteine, methionine, tryptophan, phenylalanine, leucine, isoleucine, valine, proline, threonine, selenocysteine, lysine, arginine, asparagine, glutamine, glutamic acid, aspartic acid, and histidine.

The chimeric aaRS variants generated by this method can be more aggressively engineered to create mutants that selectively charge various Uaas. Due to their improved robustness, these would provide access to a wider range of Uaa-selective mutants. In addition to unnatural amino acids, the aaRS mutants can also be used to charge other nonnatural substrates including, but not limited to, hydroxyl-acids, thio-acids, R-amino acids, etc.

These engineered aaRS mutants can be used in any eukaryotic cell along with the appropriate cognate tRNA (suppressing a nonsense or frameshift codon, or a codon composed of one or more nonnatural nucleobases). Such expression hosts include, but are not limited to, yeast, insect cells, and mammalian cells. Additionally, these aaRS/tRNA pairs can also be used for Uaa incorporation in engineered ATM *E. coli* strains, where this bacterial pair has been functionally replaced with a eukaryotic or archaeal counterpart. The present invention describes the composition of thermostable bacteria-derived TyrRS variants that can be more aggressively engineered for Uaa incorporation than their wild-type counterparts. The invention is not restricted to TyrRS, however; the method to generate such active and thermostable mutants, which is described as a part of this invention, can also be readily extended to all other bacteria-derived aaRSs that can be engineered for Uaa incorporation in eukaryotic cells.

Example 1

Materials and Methods
General Materials:

All cloning and plasmid propagation were done in DH10B *E. coli* cells. Restriction enzymes, Phusion HS II High-Fidelity DNA polymerase, and IPTG were obtained from Fisher. T4 DNA ligase was obtained from Enzymatic. DNA extraction and PCR clean up were conducted with Macherey-Nagel Binding Buffer NTI and Epoch mini spin columns from Thermo Fisher Scientific. Media components were obtained from Fisher Scientific. The following antibiotic stock concentrations were used: ampicillin 100 μg/mL, kanamycin 50 μg/mL, spectinomycin 100 μg/mL, chloramphenicol 35 μg/mL for LB Agar plates and cultures. A Cole Parmer Ultrasonic Processor was used for making *E. coli* lysate by sonication. Protein purification was conducted with a HisPur Ni-NTA resin from ThermoScientific. Dot blots were done with GE Healthcare life sciences nitrocellulose blotting membrane (0.45 um). Western blots were conducted with a PVDF membrane, antibodies, and SuperSignal West Dura Extended Duration Substrate for western blot from Thermo Fisher Scientific.

Accession Codes:

*E. coli* tyrosyl-tRNA synthetase (EcTyrRS, NCBI BAA15398.2)

*G. stearothermophilus* tyrosyl-tRNA synthetase (GsTyrRS, NCBI KOR92528.1)

| Bacterial and virus strains | | |
|---|---|---|
| Strain | Source | Catalog Number |
| ATMY6 | Chatterjee lab | N/A |
| *E. coli* DH10B | Thermo Fisher Scientific | 18297010 |

| Chemicals, peptides, and recombinant proteins | | |
|---|---|---|
| Reagent | Source | Catalog Number |
| para-benzoyl-1-phenylalanine | Chem-Impex International | 05110 |
| O-methyl tyrosine | Fisher Scientific | AAH6309606 |

| Experimental models: cell lines | | |
|---|---|---|
| Strain | Source | Catalog Number |
| HEK293T | ATCC | CRL-1573 |

Construction of plasmids to express aaRS for ncAA incorporation into sfGFP and EGFP: The *G. stearothermophilus* tyrosyl-aaRS was PCR amplified from a gBlock purchased from IDT, digested with NdeI/NcoI, and inserted into the pBK vector backbone. The mutant *G. stearothermophilus* tyrosyl-aaRS mutants were then generated via standard site-directed mutagenesis of the appropriate active site residues. The pBK *E. coli* tyrosyl-aaRS wild type and mutants were previously reported.[36,37]

The chimeric H2 and H6 aaRS' were constructed by PCR amplification of the *E. coli* tyrosyl-aaRS N-terminus and the *G. stearothermophilus* C-terminus. The inserts were then made through overlap amplification, digested with NdeI/NcoI, and inserted into the pBK vector backbone. The mutant chimeric aaRS were then generated via standard site-directed mutagenesis.[38]

For expression of the aaRS in mammalian cells, terminal primers were used to PCR amplify the aaRS' from their respective pBK plasmids. This was followed by digestion of the PCR products with NheI/XhoI into the pB1U vector backbone.

Construction of plasmids to express aaRS for CETSA: The *E. coli, G. stearothermophilus*, and chimeric aaRS' were PCR amplified from their respective pBK constructs, digested with NdeI/HindIII, and inserted into the pET22b vector backbone. The N-terminal primer appended a 10×-Histidine tag (SEQ ID NO: 4) to each aaRS for future imaging.

sfGFP* fluorescence analysis and expression: For *E. coli* expression, the pBK aaRS and pEvol T5 EcY-TAG sfGFP151* reporter plasmids were co-transformed into ATMY6 cells.[36] A 5 mL overnight culture was inoculated with a single colony and the appropriate antibiotics. The overnight starter culture was then used to inoculate a 20 mL LB Media culture supplemented with antibiotics. Cultures were grown to an OD600 of 0.6 then induced with a final concentration of 1 mM IPTG, the appropriate ncAA (1 mM), and incubated for 16 hours at 30° C. with shaking (250 rpm). The cultures were then spun down, the LB media was removed, and the cells were resuspended in 1×PBS. Fluorescence readings were collected in a 96-well plate using a SpectraMAX M5 (Molecular Devices) (ex=488 nm and em=534 nm). Mean of two independent experiments were reported, and error bars represent standard deviation.

EGFP* fluorescence analysis, expression and purification: For fluorescence analysis, HEK 293T cells were seeded at a density of 600,000 cells per well for a 12-well plate the day before transfection. A total amount of 1.5 μg DNA (0.75 μg of each plasmid for two-plasmids)+3.5 μL PEI+17.5 μL DMEM was used for transfection of each well. Fluorescence images and EGFP expression analysis were performed 48 hours post transfection following previously mentioned protocols.[39] Fluorescence readings were collected in a 96-well plate using a SpectraMAX M5 (Molecular Devices) (ex=488 nm and em=510 nm). Mean of four independent experiments were reported, and error bars represent standard deviation.

For EGFP protein purification incorporating one ncAA, HEK293T cells were seeded in 100 mm cell culture dishes (5 million per dish) 24 hours prior to transfection.

CETSA assay: For aaRS expression, TOP10 *E. coli* cells were transformed with a single pET22b-N-terminal-10×-Histidine tagged-aaRS plasmid. Overnight cultures were inoculated with a single colony, then used to inoculate 20 mL LB Media cultures with the appropriate antibiotics, grown to an OD600 of 0.6, and induced with IPTG (final concentration of 1 mM) for 15 minutes at 30° C. with shaking. The cultures were then spun down, the LB Media was removed, and the cell pellets were resuspended in 500 μL of sonication buffer (100 mM NaCl, 25 mM Tris HCl, pH 8.0).

For lysate preparation, the cell pellets were treated to three freeze thaw cycles followed by three cycles of sonication (75% power, 20 pulses), spun down, and the supernatant was collected. Each supernatant was divided into 50 μL aliquots and heated at varying temperatures for 5 minutes on a Perkin Elmer Cetus DNA Thermal Cycler 480 and spun down at maximum speed for 10 minutes. Then 3 μL of the supernatant was inoculated on a nitrocellulose membrane and treated to western blot analysis following previously described protocols.[39] Antibodies used for imaging include: mouse anti-Histidine 6× tag (SEQ ID NO: 3) antibody (1:1000 dilution), chicken anti-mouse IgG secondary antibody-HRP conjugate (1:5000 dilution).

Solubility Western: DH10B cells were transformed with a pET22b-N-term-10×-His-aaRS plasmid and an overnight 5 mL culture was inoculated with a starter colony. A 20 mL culture was then inoculated and grown to an OD600 of 0.6, allowed to grow for 4 hours at 30° C., spun down, and lysed by sonication following the same protocol as the aforementioned CETSA assay. This was resolved using 12% SDS-PAGE gel and worked up for a western following previously described protocols.[4] The antibodies used for this protocol were the same as those for the CETSA assay.

Primers and Other DNA Sequences:

```
EcYRS NdeI-F
                                    (SEQ ID NO: 5)
TTTGAGGAATCCCATATGGCAAGCAGTAACTTGATT

AAACAATTGCAAGAG

EcYRS NcoI-R
                                    (SEQ ID NO: 6)
AATTCCATGGTTATTTCCAGCAAATCAGACACTAATTC

GsYRS NdeI-F
                                    (SEQ ID NO: 7)
ATTATTATGAATCCCATATGATGGACCTGCTGGCGG

AACTGCAATG

pBK MCS JI sq-R
                                    (SEQ ID NO: 8)
GAGATCATGTAGGCCTGATAAGCGTAGC

H2 EcYRS-IR
                                    (SEQ ID NO: 9)
GCGATCGGACGGTGACCCGCCTGCTGGAAGCGTTTC

AGGCATAACAATG

H2 Gs YRS-iF
                                   (SEQ ID NO: 10)
CCTGAAACGCTTCCAGCAGGCGGGTCACCGTCCGATC

GCGCTGGTTG
```

-continued

```
H6 EcYRS-IR
                                   (SEQ ID NO: 11)
CCGCTTTCGGTTTTGCCAAATTTGGTGCCATCTGCT

TTAGTGATCAGCGGAACG

H6 GsYRS-iF
                                   (SEQ ID NO: 12)
CACTAAAGCAGATGGCACCAAATTTGGCAAAACCGA

AAGCGGTACCATTTG

EcYRS NheI-F
                                   (SEQ ID NO: 13)
TTTGAGGAATCCGCTAGCGCAAGCAGTAACTTGATT

AAACAATTGCAAGAG

EcYRS XhoI-R
                                   (SEQ ID NO: 14)
AATTCTCGAGTTATTTCCAGCAAATCAGACACTAATTC

GsYRS NheI-F
                                   (SEQ ID NO: 15)
AATAATGCTAGCATGGACCTGCTGGCG

GsYRS XhoI-R
                                   (SEQ ID NO: 16)
AATTCTCGAGTTACGCATAACGAATCAGATAGTATTTC

EcYRS-nterm 10XHis-NdeI-F
                                   (SEQ ID NO: 17)
GAAATTACATATGCATCATCACCATCACCATCATCA

TCATCACGCAAGCAGTAACTTGATTAAACAATTGCA

AGAG

EcYRS-HindIII-R
                                   (SEQ ID NO: 18)
AATTAAGCTTTTATTTCCAGCAAATCAGACACTAATTC

GsYRS-nterm10XHis-NdeI-F
                                   (SEQ ID NO: 19)
GAAATTACATATGCATCATCACCATCACCATCATCA

TCATCACGACCTGCTGGCGGAACTGCAATGG

GsYRS-HindIII-R
                                   (SEQ ID NO: 20)
AATTAAGCTTTTACGCATAACGAATCAGATAGTATTTC

MjYRS-nterm 10XHis-NdeI-F
                                   (SEQ ID NO: 21)
GAAATTACATATGCATCATCACCATCACCATCATCA

TCATCACgacgaatttgaaatgataaagagaaacacatctg

MjYRS-HindIII-R
                                   (SEQ ID NO: 22)
AATTAAGCTTTTATAATCTCTTTCTAATTGGCTCTA

AAATC

GeobacYRS-Y34G-R
                                   (SEQ ID NO: 23)
GCTATCCGCGGTCGGGTCGAAACCGCAACCCAGGGT

CACACGTTCCTCGTTCAGC

GeobacYRS-D176G-R
                                   (SEQ ID NO: 24)
CAGCCTTCGGTTTCGTACAGACGCAGGAAACCATAC

GCTTGCAGCATCATGTAGCTAAAC
```

-continued

GeobacYRS-GGFL-L180A-R (SEQ ID NO: 25)

CAGACGGCAGCCTTCGGTTTCGTAGGCACGCAGGAA

ACCATACGCTTG

GeobacYRS-D176G-F (SEQ ID NO: 26)

GTTTAGCTACATGATGCTGCAAGCGTATGGTTTCCT

GCGTCTGTACGAAACCGAAGGCTG

GeobacYRS-GGFL-L180A-F (SEQ ID NO: 27)

CAAGCGTATGGTTTCCTGCGTGCCTACGAAACCGAA

GGCTGCCGTCTG gBlock sequence of *G. stearothermophilus* tyrosyl aminoacyl-tRNA synthetase (SEQ ID NO: 28)

ATGGCGAGCAGCGACCTGCTGGCGGAACTGCAATGG

CGTGGCCTGGTTAATCAGACCACCGACGAAGATGGC

CTGCGTAAACTGCTGAACGAGGAACGTGTGACCCTG

TATTGCGGTTTCGACCCGACCGCGGATAGCCTGCAC

ATCGGCAACCTGGCGGCGATTCTGACCCTGCGTCGT

TTTCAGCAAGCGGGTCACCGTCCGATCGCGCTGGTT

GGTGGTGCGACCGGTCTGATTGGCGACCCGAGCGGC

AAGAAAAGCGAGCGTACCCTGAACGCGAAGGAAACC

GTTGAAGCGTGGAGCGCGCGTATCAAAGAACAGCTG

GGTCGTTTCCTGGACTTTGAGGCGGATGGCAACCCG

GCGAAGATTAAAAACAACTATGACTGGATCGGTCCG

CTGGATGTGATTACCTTCCTGCGTGATGTGGGCAAG

CACTTTAGCGTTAACTACATGATGGCGAAAGAGAGC

GTTCAGAGCCGTATCGAAACCGGTATTAGCTTCACC

GAGTTTAGCTACATGATGCTGCAAGCGTATGACTTC

CTGCGTCTGTACGAAACCGAAGGCTGCCGTCTGCAG

ATCGGTGGCAGCGATCAATGGGGTAACATCACCGCG

GGCCTGGAACTGATTCGTAAGACCAAAGGTGAAGCG

CGTGCGITTGGCCTGACCATCCCGCTGGTGACCAAA

GGAGAAAACCAGCCCGTACGAATTCTATCAGTTTTG

GATCAACACCGACGATCGTGACGTTATTCGTTACCT

GAAGTATTICACCTTTCTGAGCAAAGAGGAAATCGA

AGCGCTGGAGCAGGAACTGCGIGAGGCGCCGGAAAA

GCGIGCGGCGCAAAAAGCGCTGGCGGAGGAAGTGAC

CAAACTGGTTCACGGTGAGGAAGCGCTGCGTCAGGC

GATCCGTATTAGCGAAGCGCTGTTTAGCGGTGATAT

CGCGAACCTGACCGCGGCGGAGATTGAACAAGGCTT

CAAGGACGTGCCGAGCTTTGTTCACGAAGGTGGCGA

TGTGCCGCTGGTTGAGCTGCTGGTTAGCGCGGGTAT

CAGCCCGAGCAAACGTCAGGCGCGTGAAGACATCCA

-continued

AAACGGTGCGATTTACGTGAACGGCGAGCGTCTGCA

AGATGTTGGCGCGATTCTGACCGCGGAACACCGTCT

GGAAGGTCGTTTTACCGTTATCCGTCGTGGCAAGAA

GAAATACTATCTGATTCGTTATGCGTAA

Example 2

Construction of Tyrosyl-tRNA Synthetase Chimeric Libraries Through DNA Shuffling:

The *G. stearothermophilus* and *E. coli* TyrRS are PCR amplified using external primers that anneal ~70 bp upstream and downstream of the target sequence. The amplified target genes are gel-purified, mixed in equimolar ratio, and were partially digested with DNASe I. The fragmented inserts were gel purified and reassembled following an established stepwise amplification protocol.[40] The reassembled product was then PCR amplified with a second set of primers that anneal ~40 bp upstream and downstream of the target sequence, and cloned into a plasmid behind a constitutively active promoter.

Construction of Tyrosyl-tRNA Synthetase Chimeric Libraries Through StEP:

The *G. stearothermophilus* and *E. coli* TyrRS are PCR amplified using external primers that anneal ~70 bp upstream and downstream of the target sequence. The amplified target genes were gel-purified, mixed at an equimolar ratio, and PCR amplified with Taq-polymerase for 80 cycles (short low-temperature cycles, such as 5 s at 55° C.) with a second set of primers that anneal ~40 bp upstream and downstream of the target sequence.[41] During this amplification, short stretches of the sequences are generated, which can reanneal to a different template in the following cycle, resulting in chimeric constructs. The resulting chimeric constructs were cloned into a plasmid behind a constitutively active promoter.

Construction and Selection of aaRS-GFPmut3 Fusion Fluorescence Reporter Construct:

The library of chimeric TyrRS mutants are first selected for activity. This selection uses the ability of the active TyrRS mutants to enable the expression of a TAG-inactivated antibiotic resistance gene (such as ampicillin or chloramphenicol) and allow the host survive the corresponding antibiotic treatment. Next, the library of active chimeric TyrRS mutants was PCR amplified and fused with a GFP reporter (e.g., the GFPmut3 reporter) using overlap-extension PCR. The full-length fusion insert[42] was cloned into a plasmid under a strong and inducible promoter such as T5-lac. The resulting plasmid library is then transformed into *E. coli* cells and the chimeric proteins are expressed. Those with lower stability would render the fused GFP non-fluorescent, while the stable variants will keep the GFP fluorescent. A FACS selection is then used to enrich the most stable and active mutants. Isolated mutants are individually screened for both their stability and activity.

REFERENCES

The following references are herein incorporated by reference in their entirety.

[1] Chin, J. W. (2017) Expanding and reprogramming the genetic code, *Nature* 550, 53.

[2] Dumas, A., Lercher, L., Spicer, C. D., and Davis, B. G. (2015) Designing logical codon reassignment—Expanding the chemistry in biology, *Chemical Science* 6, 50-69.

[3] Italia, J. S., Zheng, Y., Kelemen, R. E., Erickson, S. B., Addy, P. S., and Chatterjee, A. (2017) Expanding the genetic code of mammalian cells, *Biochemical Society transactions* 45, 555-562.

[4] Mukai, T., Lajoie, M. J., Englert, M., and Söll, D. (2017) Rewriting the genetic code, *Annual review of microbiology* 71, 557-577.

[5] Young, D. D., and Schultz, P. G. (2018) Playing with the molecules of life, *ACS chemical biology.*

[6] Vargas-Rodriguez, O., Sevostyanova, A., Söll, D., and Crnković, A. (2018) Upgrading aminoacyl-tRNA synthetases for genetic code expansion, *Current opinion in chemical biology* 46, 115-122.

[7] Italia, J. S., Addy, P. S., Wrobel, C. J., Crawford, L. A., Lajoie, M. J., Zheng, Y., and Chatterjee, A. (2017) An orthogonalized platform for genetic code expansion in both bacteria and eukaryotes, *Nature chemical biology* 13, 446-450.

[8] Chin, J. W., Cropp, T. A., Anderson, J. C., Mukherji, M., Zhang, Z., and Schultz, P. G. (2003) An expanded eukaryotic genetic code, *Science* 301, 964-967.

[9] Sakamoto, K., Hayashi, A., Sakamoto, A., Kiga, D., Nakayama, H., Soma, A., Kobayashi, T., Kitabatake, M., Takio, K., and Saito, K. (2002) Site-specific incorporation of an unnatural amino acid into proteins in mammalian cells, *Nucleic acids research* 30, 4692-4699.

[10] Chatterjee, A., Xiao, H., Bollong, M., Ai, H. W., and Schultz, P. G. (2013) Efficient viral delivery system for unnatural amino acid mutagenesis in mammalian cells, *Proceedings of the National Academy of Sciences of the United States of America* 110, 11803-11808.

[11] Zheng, Y., Addy, P. S., Mukherjee, R., and Chatterjee, A. (2017) Defining the current scope and limitations of dual noncanonical amino acid mutagenesis in mammalian cells, *Chem Sci* 8, 7211-7217.

[12] Zheng, Y., Lewis, T. L., Jr., Igo, P., Polleux, F., and Chatterjee, A. (2017) Virus-Enabled Optimization and Delivery of the Genetic Machinery for Efficient Unnatural Amino Acid Mutagenesis in Mammalian Cells and Tissues, *ACS synthetic biology* 6, 13-18.

[13] Italia, J. S., Latour, C., Wrobel, C. J., and Chatterjee, A. (2018) Resurrecting the bacterial tyrosyl-tRNA Synthetase/tRNA pair for expanding the genetic code of both *E. coli* and eukaryotes, *Cell chemical biology* 25, 1304-1312. e1305.

[14] Dugan, A., Majmudar, C. Y., Pricer, R., Niessen, S., Lancia, J. K., Fung, H. Y.-H., Cravatt, B. F., and Mapp, A. K. (2016) Discovery of enzymatic targets of transcriptional activators via in vivo covalent chemical capture, *Journal of the American Chemical Society* 138, 12629-12635.

[15] Krishnamurthy, M., Dugan, A., Nwokoye, A., Fung, Y.-H., Lancia, J. K., Majmudar, C. Y., and Mapp, A. K. (2011) Caught in the act: Covalent cross-linking captures activator-coactivator interactions in vivo, *ACS chemical biology* 6, 1321-1326.

[16] Hino, N., Okazaki, Y., Kobayashi, T., Hayashi, A., Sakamoto, K., and Yokoyama, S. (2005) Protein photo-cross-linking in mammalian cells by site-specific incorporation of a photoreactive amino acid, *Nature methods* 2, 201.

[17] Wilkins, B. J., Rall, N. A., Ostwal, Y., Kruitwagen, T., Hiragami-Hamada, K., Winkler, M., Barral, Y., Fischle, W., and Neumann, H. (2014) A cascade of histone modifications induces chromatin condensation in mitosis, *Science* 343, 77-80.

[18] Tokuriki, N., and Tawfik, D. S. (2009) Stability effects of mutations and protein evolvability, *Current opinion in structural biology* 19, 596-604.

[19] Tokuriki, N., and Tawfik, D. S. (2009) Protein dynamism and evolvability, *Science* 324, 203-207.

[20] Socha, R. D., and Tokuriki, N. (2013) Modulating protein stability-directed evolution strategies for improved protein function, *The FEBS journal* 280, 5582-5595.

[21] Trudeau, D. L., and Tawfik, D. S. (2019) Protein engineers turned evolutionists—the quest for the optimal starting point, *Current opinion in biotechnology* 60, 46-52.

[22] Martinez Molina, D., and Nordlund, P. (2016) The cellular thermal shift assay: a novel biophysical assay for in situ drug target engagement and mechanistic biomarker studies, *Annual review of pharmacology and toxicology* 56, 141-161.

[23] Martinez, D. M., Jafari, R., Ignatushchenko, M., Seki, T., Larsson, E. A., Dan, C., Sreekumar, L., Cao, Y., and Nordlund, P. (2013) Monitoring drug target engagement in cells and tissues using the cellular thermal shift assay, *Science* (New York, N.Y.) 341, 84-87.

[24] Chin, J. W., Martin, A. B., King, D. S., Wang, L., and Schultz, P. G. (2002) Addition of a photocrosslinking amino acid to the genetic code of *Escherichia coli, Proceedings of the National Academy of Sciences* 99, 11020-11024.

[25] Young, D. D., Young, T. S., Jahnz, M., Ahmad, I., Spraggon, G., and Schultz, P. G. (2011) An evolved aminoacyl-tRNA synthetase with atypical polysubstrate specificity, *Biochemistry* 50, 1894-1900.

[26] Guez-Ivanier, V., Hermann, M., Baldwin, D., and Bedouelle, H. (1993) Mapping the stability determinants of bacterial tyrosyl transfer RNA synthetases by an experimental evolutionary approach, *Journal of molecular biology* 234, 209-221.

[27] Laowanapiban, P., Kapustina, M., Vonrhein, C., Delarue, M., Koehl, P., and Carter, C. W., Jr. (2009) Independent saturation of three TrpRS subsites generates a partially assembled state similar to those observed in molecular simulations, *Proceedings of the National Academy of Sciences of the United States of America* 106, 1790-1795.

[28] Sakurama, H., Takita, T., Mikami, B., Itoh, T., Yasukawa, K., and Inouye, K. (2009) Two crystal structures of lysyl-tRNA synthetase from *Bacillus stearothermophilus* in complex with lysyladenylate-like compounds: insights into the irreversible formation of the enzyme-bound adenylate of L-lysine hydroxamate, *Journal of biochemistry* 145, 555-563.

[29] Brick, P., Bhat, T. N., and Blow, D. M. (1989) Structure of tyrosyl-tRNA synthetase refined at 2.3 A resolution. Interaction of the enzyme with the tyrosyl adenylate intermediate, *J Mol Biol* 208, 83-98.

[30] Wolf-Watz, M., Thai, V., Henzler-Wildman, K., Hadjipavlou, G., Eisenmesser, E. Z., and Kern, D. (2004) Linkage between dynamics and catalysis in a thermophilic-mesophilic enzyme pair, *Nature structural & molecular biology* 11, 945.

[31] Li, Y., Drummond, D. A., Sawayama, A. M., Snow, C. D., Bloom, J. D., and Arnold, F. H. (2007) A diverse family of thermostable cytochrome P450s created by recombination of stabilizing fragments, *Nature biotechnology* 25, 1051.

[32] Jermutus, L., Tessier, M., Pasamontes, L., van Loon, A. P., and Lehmann, M. (2001) Structure-based chimeric enzymes as an alternative to directed enzyme evolution: phytase as a test case, *Journal of biotechnology* 85, 15-24.

[33] Zheng, Y., Mukherjee, R., Chin, M. A., Igo, P., Gilgenast, M. J., and Chatterjee, A. (2017) Expanding the scope of single- and double-noncanonical amino acid mutagenesis in mammalian cells using orthogonal polyspecific leucyl-tRNA synthetases, *Biochemistry* 57, 441-445.

[34] Chatterjee, A., Xiao, H., Yang, P. Y., Soundararajan, G., and Schultz, P. G. (2013) A Tryptophanyl-tRNA Synthetase/tRNA Pair for Unnatural Amino Acid Mutagenesis in *E. coli, Angewandte Chemie International Edition* 52, 5106-5109.

[35] Wu, N., Deiters, A., Cropp, T. A., King, D., and Schultz, P. G. (2004) A genetically encoded photocaged amino acid, *Journal of the American Chemical Society* 126, 14306-14307.

[36] J. S. Italia, C. Latour, C. J. J. Wrobel, A. Chatterjee, *Cell Chem. Biol,* 2018, 25, 1304-1312.

[37] J. W. Chin, A. B. Martin, D. S. King, L. Wang, P. G. Schultz, *Proc. Natl. Acad Sci. U.S.A.,* 2002, 99, 11020-11024.

[38] V. Guez-Ivanier, M. Hermann, D. Baldwin, H. Bedouelle, *J. Mol. Biol.,* 1993, 234, 209-221.

[39] Y. Zheng, T. L. Lewis, P. Igo, F. Polleux, A. Chatterjee, *ACS Synth. Biol,* 2017, 6, 13-18.

[40] A. J. Meyer, J. W. Ellefson, A. D. Ellington, *Curr Protoc Mol Biol.,* 2015, 105, Unit-15.12.

[41] H. Zhao, W. Zha, *Nature Protocols,* 2006, 1, 1865-1871.

[42] E. E. Wrenbeck, M. A. Bedewitz, J. R. Klesmith, S. Noshin, C. S. Barry, T. A. Whitehead, *ACS Synth. Biol.,* 2019, 8, 3, 474-481.

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition comprising a polynucleotide encoding a biologically-active chimeric thermostable tyrosyl aminoacyl-tRNA synthetase, comprising an *Escherichia coli* (*E. coli*) tyrosyl aminoacyl-tRNA synthetase and a thermostable *Geobacillus stearothermophilis* (*G. stearothermophilis*) tyrosyl aminoacyl-tRNA synthetase constructed from a nucleic acid sequence of a mesophilic bacterial *E. coli* tyrosyl aminoacyl-tRNA synthetase and a nucleic acid sequence of a thermostable *G. stearothermophilis* tyrosyl aminoacyl-tRNA synthetase of a thermostable bacterial homolog, wherein the thermostable bacteria is selected from the group consisting of: *Geobacillus stearothermophilis, Bacillus stearothermophilis, Thermus thermophilis* or a *Thermoanaerobacter* species;

wherein the mesophilic bacteria is selected from the group consisting of *Escherichia coli*, a *Staphylococcus* species, a *Streptococcus* species, or a *Pseudomonas* species;

wherein the chimeric thermostable *E.* coli-*G. stearothermophilis* tyrosyl aminoacyl-tRNA synthetase aminoacylates an *E. coli* $tRNA^{tyr}$ with a tyrosine amino acid or a tyrosine amino acid analog in bacterial or mammalian cells;

wherein the chimeric thermostable tyrosyl aminoacyl-tRNA synthetase has increased thermostability compared to the mesophilic *E. coli* wild-type tyrosyl aminoacyl-tRNA synthetase in bacterial or mammalian cells; and wherein the amino acid sequence of the chimera comprises an amino acid sequence selected from the group consisting of:

SEQ ID NOs: 42, 43, 44, 46 or 47, or an amino acid sequence with at least 90% sequence identity to SEQ ID NOs: 42, 43, 44, 46 or 47.

2. The composition of claim 1, wherein the mesophilic bacterial *E. coli* tyrosyl aminoacyl-tRNA synthetase of the chimera is a variant *E. coli* aminoacyl-tRNA synthetase comprising a mutation in its active site, resulting in the increase of the enzymatic activity of the variant aminoacyl-tRNA synthetase to aminoacylate its cognate tRNA with an unnatural amino acid compared to the wild-type mesophilic bacterial aminoacyl-tRNA synthetase wherein the amino acid sequence of the chimera comprises an amino acid sequence selected from the group consisting of: SEQ ID NOs: 43, 44 or 47, or an amino acid sequence comprising at least 90% sequence identity to SEQ ID NOs: 43, 44 or 47; and wherein the variant *E. coli* tyrosyl aminoacyl-tRNA synthetase of the chimera aminoacylates/charges its cognate *E. coli* $tRNA^{tyr}$ with a tyrosine amino acid analog.

3. The composition of claim 1, wherein the chimeric thermostable tyrosyl aminoacyl-tRNA synthetase is soluble up to about 60° C.

4. The composition of claim 1, wherein the *E. coli* tyrosyl aminoacyl-tRNA synthetase of the chimeric thermostable chimeric aminoacyl-tRNA synthetase comprises SEQ ID NO: 42 or 46, or an amino acid sequence comprising at least 90% sequence identity to SEQ ID NO: 42 or 46; and wherein the *E. coli* tyrosyl aminoacyl-tRNA synthetase of the chimera aminoacylates/charges its cognate wild-type RNA *E. coli* $tRNA^{tyr}$ with a naturally occurring tyrosine amino acid.

5. The composition of claim 2, wherein the mutation in the active site results in the incorporation of the unnatural amino acid p-benzoylphenylalanine (pBpA) in a mammalian protein.

6. The composition of claim 5, wherein the amino acid sequence of the chimera comprises SEQ ID NO:43 or SEQ ID NO:47, or an amino acid sequence with at least 90% sequence identity to either SEQ ID NO:43 or SEQ ID NO: 47.

7. The composition of claim 2, wherein the mutation in the active site results in the incorporation of the unnatural amino acid O-methyltyrosine (OMeY) in a mammalian protein.

8. The composition of claim 7, wherein the amino acid sequence comprises SEQ ID NO:44, or an amino acid sequence with at least 90% sequence identity to SEQ ID NO:44.

* * * * *

SEQUENCE LISTING

```
<160> NUMBER OF SEQ ID NOS: 47

<210> SEQ ID NO 1
<211> LENGTH: 1269
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1

atggcaagca gtaacttgat taaacaattg caagagcggg ggctggtagc ccaggtgacg      60

gacgaggaag cgttagcaga gcgactggcg caaggcccga tcgcgctcta ttgcggcttc     120

gatcctaccg ctgacagctt gcatttgggg catcttgttc cattgttatg cctgaaacgc     180

ttccagcagg cgggtcaccg tccgatcgcg ctggttggtg gtgcgaccgg tctgattggc     240

gacccgagcg gcaagaaaag cgagcgtacc ctgaacgcga aggaaaccgt tgaagcgtgg     300

agcgcgcgta tcaaagaaca gctgggtcgt ttcctggact ttgaggcgga tggcaacccg     360

gcgaagatta aaaacaacta tgactggatc ggtccgctgg atgtgattac cttcctgcgt     420

gatgtgggca agcactttag cgttaactac atgatggcga aagagagcgt tcagagccgt     480

atcgaaaccg gtattagctt caccgagttt agctacatga tgctgcaagc gtatgatttc     540

ctgcgtctgt acgaaaccga aggctgccgt ctgcagatcg gtggcagcga tcaatggggt     600

aacatcaccg cgggcctgga actgattcgt aagaccaaag gtgaagcgcg tgcgtttggc     660

ctgaccatcc cgctggtgac caaggcggac ggtaccaagt ttggcaaaac cgaaagcggt     720

accatttggc tggataagga gaaaaccagc ccgtacgaat tctatcagtt ttggatcaac     780

accgacgatc gtgacgttat tcgttacctg aagtatttca cctttctgag caaagaggaa     840

atcgaagcgc tggagcagga actgcgtgag gcgccggaaa agcgtgcggc gcaaaaagcg     900

ctggcggagg aagtgaccaa actggttcac ggtgaggaag cgctgcgtca ggcgatccgt     960

attagcgaag cgctgtttag cggtgatatc gcgaacctga ccgcggcgga gattgaacaa    1020

ggcttcaagg acgtgccgag ctttgttcac gaaggtggcg atgtgccgct ggttgagctg    1080

ctggttagcg cgggtatcag cccgagcaaa cgtcaggcgc gtgaagacat ccaaaacggt    1140
```

gcgatttacg tgaacggcga gcgtctgcaa gatgttggcg cgattctgac cgcggaacac 1200
cgtctggaag gtcgttttac cgttatccgt cgtggcaaga agaaatacta tctgattcgt 1260
tatgcgtaa 1269

<210> SEQ ID NO 2
<211> LENGTH: 1275
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 2
atggcaagca gtaacttgat taaacaattg caagagcggg ggctggtagc ccaggtgacg 60
gacgaggaag cgttagcaga gcgactggcg caaggcccga tcgcgctcta ttgcggcttc 120
gatcctaccg ctgacagctt gcatttgggg catcttgttc cattgttatg cctgaaacgc 180
ttccagcagg cgggccacaa gccggttgcg ctggtaggcg gcgcgacggg tctgattggc 240
gacccgagtt tcaaagctgc cgagcgtaag ctgaacaccg aagaaactgt tcaggagtgg 300
gtggacaaaa tccgtaagca ggttgccccg ttcctcgatt tcgactgtgg agaaaactct 360
gctatcgcgg cgaacaacta tgactggttc ggcaatatga atgtgctgac cttcctgcgc 420
gatattggca aacacttctc cgttaaccag atgatcaaca aagaagcggt taagcagcgt 480
ctcaaccgtg aagatcaggg gatttcgttc actgagtttt cctacagcct gttgcagggt 540
tatgacttcg cctgtctgaa caaacagtac ggtgtggtgc tgcaaattgg tggttctgac 600
cagtggggta acatcacttc tggtatcgac ctgacccgtc gtctgcatca gaatcaggtg 660
tttggcctga ccgttccgct gatcactaaa gcagatggca ccaaatttgg caaaaccgaa 720
agcggtacca tttggctgga taaggagaaa accagcccgt acgaattcta tcagttttgg 780
atcaacaccg acgatcgtga cgttattcgt tacctgaagt atttcacctt tctgagcaaa 840
gaggaaatcg aagcgctgga gcaggaactg cgtgaggcgc cggaaaagcg tgcggcgcaa 900
aaagcgctgg cggaggaagt gaccaaactg gttcacggtg aggaagcgct gcgtcaggcg 960
atccgtatta gcgaagcgct gtttagcggt gatatcgcga acctgaccgc ggcggagatt 1020
gaacaaggct tcaaggacgt gccgagcttt gttcacgaag gtggcgatgt gccgctggtt 1080
gagctgctgg ttagcgcggg tatcagcccg agcaaacgtc aggcgcgtga agacatccaa 1140
aacggtgcga tttacgtgaa cggcgagcgt ctgcaagatg ttggcgcgat tctgaccgcg 1200
gaacaccgtc tggaaggtcg ttttaccgtt atccgtcgtg gcaagaagaa atactatctg 1260
attcgttatg cgtaa 1275

<210> SEQ ID NO 3
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 6xHis tag"

<400> SEQUENCE: 3

His His His His His His
1 5

<210> SEQ ID NO 4

<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic 10xHis tag"

<400> SEQUENCE: 4

His His His His His His His His His His
1 5 10

<210> SEQ ID NO 5
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 5
tttgaggaat cccatatggc aagcagtaac ttgattaaac aattgcaaga g 51

<210> SEQ ID NO 6
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 6
aattccatgg ttatttccag caaatcagac actaattc 38

<210> SEQ ID NO 7
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 7
attattatga atcccatatg atggacctgc tggcggaact gcaatg 46

<210> SEQ ID NO 8
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 8
gagatcatgt aggcctgata agcgtagc 28

<210> SEQ ID NO 9
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 9
gcgatcggac ggtgacccgc ctgctggaag cgtttcaggc ataacaatg 49

<210> SEQ ID NO 10
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 10
cctgaaacgc ttccagcagg cgggtcaccg tccgatcgcg ctggttg 47

<210> SEQ ID NO 11
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 11
ccgctttcgg ttttgccaaa tttggtgcca tctgctttag tgatcagcgg aacg 54

<210> SEQ ID NO 12
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 12
cactaaagca gatggcacca aatttggcaa aaccgaaagc ggtaccattt g 51

<210> SEQ ID NO 13
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 13
tttgaggaat ccgctagcgc aagcagtaac ttgattaaac aattgcaaga g 51

<210> SEQ ID NO 14
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 14
aattctcgag ttatttccag caaatcagac actaattc 38

<210> SEQ ID NO 15
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 15
aataatgcta gcatggacct gctggcg 27

<210> SEQ ID NO 16
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 16
aattctcgag ttacgcataa cgaatcagat agtatttc 38

<210> SEQ ID NO 17
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 17
gaaattacat atgcatcatc accatcacca tcatcatcat cacgcaagca gtaacttgat 60
taaacaattg caagag 76

<210> SEQ ID NO 18
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 18
aattaagctt ttatttccag caaatcagac actaattc 38

<210> SEQ ID NO 19
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 19
gaaattacat atgcatcatc accatcacca tcatcatcat cacgacctgc tggcggaact 60
gcaatgg 67

<210> SEQ ID NO 20
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 20
aattaagctt ttacgcataa cgaatcagat agtatttc 38

<210> SEQ ID NO 21
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 21
gaaattacat atgcatcatc accatcacca tcatcatcat cacgacgaat ttgaaatgat 60
aaagagaaac acatctg 77

<210> SEQ ID NO 22
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 22
aattaagctt ttataatctc tttctaattg gctctaaaat c 41

<210> SEQ ID NO 23
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 23
gctatccgcg gtcgggtcga aaccgcaacc cagggtcaca cgttcctcgt tcagc 55

<210> SEQ ID NO 24
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 24
cagccttcgg tttcgtacag acgcaggaaa ccatacgctt gcagcatcat gtagctaaac 60

<210> SEQ ID NO 25
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 25
cagacggcag ccttcggttt cgtaggcacg caggaaacca tacgcttg 48

<210> SEQ ID NO 26
<211> LENGTH: 60

<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 26
gtttagctac atgatgctgc aagcgtatgg tttcctgcgt ctgtacgaaa ccgaaggctg 60

<210> SEQ ID NO 27
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 27
caagcgtatg gtttcctgcg tgcctacgaa accgaaggct gccgtctg 48

<210> SEQ ID NO 28
<211> LENGTH: 1269
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28
atggcgagca gcgacctgct ggcggaactg caatggcgtg gcctggttaa tcagaccacc 60
gacgaagatg gcctgcgtaa actgctgaac gaggaacgtg tgaccctgta ttgcggtttc 120
gacccgaccg cggatagcct gcacatcggc aacctggcgg cgattctgac cctgcgtcgt 180
tttcagcaag cgggtcaccg tccgatcgcg ctggttggtg gtgcgaccgg tctgattggc 240
gacccgagcg gcaagaaaag cgagcgtacc ctgaacgcga aggaaaccgt tgaagcgtgg 300
agcgcgcgta tcaaagaaca gctgggtcgt ttcctggact ttgaggcgga tggcaacccg 360
gcgaagatta aaaacaacta tgactggatc ggtccgctgg atgtgattac cttcctgcgt 420
gatgtgggca agcactttag cgttaactac atgatggcga aagagagcgt tcagagccgt 480
atcgaaaccg gtattagctt caccgagttt agctacatga tgctgcaagc gtatgacttc 540
ctgcgtctgt acgaaaccga aggctgccgt ctgcagatcg gtggcagcga tcaatggggt 600
aacatcaccg cgggcctgga actgattcgt aagaccaaag gtgaagcgcg tgcgtttggc 660
ctgaccatcc cgctggtgac caaggcggac ggtaccaagt ttggcaaaac cgaaagcggt 720
accatttggc tggataagga gaaaaccagc ccgtacgaat tctatcagtt ttggatcaac 780
accgacgatc gtgacgttat tcgttacctg aagtatttca cctttctgag caaagaggaa 840
atcgaagcgc tggagcagga actgcgtgag gcgccggaaa agcgtgcggc gcaaaaagcg 900
ctggcggagg aagtgaccaa actggttcac ggtgaggaag cgctgcgtca ggcgatccgt 960
attagcgaag cgctgtttag cggtgatatc gcgaacctga ccgcggcgga gattgaacaa 1020
ggcttcaagg acgtgccgag ctttgttcac gaaggtggcg atgtgccgct ggttgagctg 1080
ctggttagcg cgggtatcag cccgagcaaa cgtcaggcgc gtgaagacat ccaaaacggt 1140
gcgatttacg tgaacggcga gcgtctgcaa gatgttggcg cgattctgac cgcggaacac 1200
cgtctggaag gtcgttttac cgttatccgt cgtggcaaga agaaatacta tctgattcgt 1260

```
tatgcgtaa                                                                1269


<210> SEQ ID NO 29
<211> LENGTH: 424
<212> TYPE: PRT
<213> ORGANISM: Escherichia coli

<400> SEQUENCE: 29

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Tyr Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Asp Phe Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Asp Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365
```

```
Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420


<210> SEQ ID NO 30
<211> LENGTH: 419
<212> TYPE: PRT
<213> ORGANISM: Geobacillus stearothermophilus

<400> SEQUENCE: 30

Met Asp Leu Leu Ala Glu Leu Gln Trp Arg Gly Leu Val Asn Gln Thr
1               5                   10                  15

Thr Asp Glu Asp Gly Leu Arg Lys Leu Leu Asn Glu Glu Arg Val Thr
            20                  25                  30

Leu Tyr Cys Gly Phe Asp Pro Thr Ala Asp Ser Leu His Ile Gly Asn
        35                  40                  45

Leu Ala Ala Ile Leu Thr Leu Arg Arg Phe Gln Gln Ala Gly His Arg
    50                  55                  60

Pro Ile Ala Leu Val Gly Gly Ala Thr Gly Leu Ile Gly Asp Pro Ser
65                  70                  75                  80

Gly Lys Lys Ser Glu Arg Thr Leu Asn Ala Lys Glu Thr Val Glu Ala
                85                  90                  95

Trp Ser Ala Arg Ile Lys Glu Gln Leu Gly Arg Phe Leu Asp Phe Glu
            100                 105                 110

Ala Asp Gly Asn Pro Ala Lys Ile Lys Asn Asn Tyr Asp Trp Ile Gly
        115                 120                 125

Pro Leu Asp Val Ile Thr Phe Leu Arg Asp Val Gly Lys His Phe Ser
    130                 135                 140

Val Asn Tyr Met Met Ala Lys Glu Ser Val Gln Ser Arg Ile Glu Thr
145                 150                 155                 160

Gly Ile Ser Phe Thr Glu Phe Ser Tyr Met Met Leu Gln Ala Tyr Asp
                165                 170                 175

Phe Leu Arg Leu Tyr Glu Thr Glu Gly Cys Arg Leu Gln Ile Gly Gly
            180                 185                 190

Ser Asp Gln Trp Gly Asn Ile Thr Ala Gly Leu Glu Leu Ile Arg Lys
        195                 200                 205

Thr Lys Gly Glu Ala Arg Ala Phe Gly Leu Thr Ile Pro Leu Val Thr
    210                 215                 220

Lys Ala Asp Gly Thr Lys Phe Gly Lys Thr Glu Ser Gly Thr Ile Trp
225                 230                 235                 240

Leu Asp Lys Glu Lys Thr Ser Pro Tyr Glu Phe Tyr Gln Phe Trp Ile
                245                 250                 255

Asn Thr Asp Asp Arg Asp Val Ile Arg Tyr Leu Lys Tyr Phe Thr Phe
            260                 265                 270

Leu Ser Lys Glu Glu Ile Glu Ala Leu Glu Gln Glu Leu Arg Glu Ala
        275                 280                 285

Pro Glu Lys Arg Ala Ala Gln Lys Ala Leu Ala Glu Glu Val Thr Lys
    290                 295                 300

Leu Val His Gly Glu Glu Ala Leu Arg Gln Ala Ile Arg Ile Ser Glu
305                 310                 315                 320
```

```
Ala Leu Phe Ser Gly Asp Ile Ala Asn Leu Thr Ala Ala Glu Ile Glu
                325                 330                 335

Gln Gly Phe Lys Asp Val Pro Ser Phe Val His Glu Gly Gly Asp Val
            340                 345                 350

Pro Leu Val Glu Leu Leu Val Ser Ala Gly Ile Ser Pro Ser Lys Arg
        355                 360                 365

Gln Ala Arg Glu Asp Ile Gln Asn Gly Ala Ile Tyr Val Asn Gly Glu
    370                 375                 380

Arg Leu Gln Asp Val Gly Ala Ile Leu Thr Ala Glu His Arg Leu Glu
385                 390                 395                 400

Gly Arg Phe Thr Val Ile Arg Arg Gly Lys Lys Lys Tyr Tyr Leu Ile
                405                 410                 415

Arg Tyr Ala


<210> SEQ ID NO 31
<211> LENGTH: 3241
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31

cttttgctga gttgaaggat ccgcggccgc tcgggttgtc agcctgtccc gcttataaga     60

tcatacgccg ttatacgttg tttacgcttt gaggaatccc atatgatgga cctgctggcg    120

gaactgcaat ggcgtggcct ggttaatcag accaccgacg aagatggcct gcgtaaactg    180

ctgaacgagg aacgtgtgac cctgtattgc ggtttcgacc cgaccgcgga tagcctgcac    240

atcggcaacc tggcggcgat tctgaccctg cgtcgttttc agcaagcggg tcaccgtccg    300

atcgcgctgg ttggtggtgc gaccggtctg attggcgacc cgagcggcaa gaaaagcgag    360

cgtaccctga acgcgaagga aaccgttgaa gcgtggagcg cgcgtatcaa agaacagctg    420

ggtcgtttcc tggactttga ggcggatggc aacccggcga agattaaaaa caactatgac    480

tggatcggtc cgctggatgt gattaccttc ctgcgtgatg tgggcaagca ctttagcgtt    540

aactacatga tggcgaaaga gagcgttcag agccgtatcg aaaccggtat tagcttcacc    600

gagtttagct acatgatgct gcaagcgtat gacttcctgc gtctgtacga aaccgaaggc    660

tgccgtctgc agatcggtgg cagcgatcaa tggggtaaca tcaccgcggg cctggaactg    720

attcgtaaga ccaaaggtga agcgcgtgcg tttggcctga ccatcccgct ggtgaccaag    780

gcggacggta ccaagtttgg caaaaccgaa agcggtacca tttggctgga taaggagaaa    840

accagcccgt acgaattcta tcagttttgg atcaacaccg acgatcgtga cgttattcgt    900

tacctgaagt atttcacctt tctgagcaaa gaggaaatcg aagcgctgga gcaggaactg    960

cgtgaggcgc cggaaaagcg tgcggcgcaa aaagcgctgg cggaggaagt gaccaaactg   1020

gttcacggtg aggaagcgct gcgtcaggcg atccgtatta gcgaagcgct gtttagcggt   1080

gatatcgcga acctgaccgc ggcggagatt gaacaaggct tcaaggacgt gccgagcttt   1140

gttcacgaag gtggcgatgt gccgctggtt gagctgctgg ttagcgcggg tatcagcccg   1200

agcaaacgtc aggcgcgtga agacatccaa aacggtgcga tttacgtgaa cggcgagcgt   1260

ctgcaagatg ttggcgcgat tctgaccgcg gaacaccgtc tggaaggtcg ttttaccgtt   1320

atccgtcgtg gcaagaagaa atactatctg attcgttatg cgtaaggtac catggctgca   1380
```

-continued gtttcaaacg ctaaattgcc tgatgcgcta cgcttatcag gcctacatga tctctgcaat 1440
atattgagtt tgcgtgcttt tgtaggccgg ataaggcgtt cacgccgcat ccggcaagaa 1500
acagcaaaca atccaaaacg ccgcgttcag cggcgttttt tctgcttttc ttcgcgaatt 1560
aattccgctt cgcacatgtg agcaaaaggc cagcaaaagg ccaggaaccg taaaaaggcc 1620
gcgttgctgg cgtttttcca taggctccgc ccccctgacg agcatcacaa aaatcgacgc 1680
tcaagtcaga ggtggcgaaa cccgacagga ctataaagat accaggcgtt tccccctgga 1740
agctccctcg tgcgctctcc tgttccgacc ctgccgctta ccggatacct gtccgccttt 1800
ctcccttcgg gaagcgtggc gctttctcat agctcacgct gtaggtatct cagttcggtg 1860
taggtcgttc gctccaagct gggctgtgtg cacgaacccc ccgttcagcc cgaccgctgc 1920
gccttatccg gtaactatcg tcttgagtcc aacccggtaa gacacgactt atcgccactg 1980
gcagcagcca ctggtaacag gattagcaga gcgaggtatg taggcggtgc tacagagttc 2040
ttgaagtggt ggcctaacta cggctacact agaaggacag tatttggtat ctgcgctctg 2100
ctgaagccag ttaccttcgg aaaaagagtt ggtagctctt gatccggcaa acaaaccacc 2160
gctggtagcg gtggtttttt tgtttgcaag cagcagatta cgcgcagaaa aaaaggatct 2220
caagaagatc ctttgatctt ttctacgggg tctgacgctc agtggaacga aaactcacgt 2280
taagggattt tggtcatgaa caataaaact gtctgcttac ataaacagta atacaagggg 2340
tgttatgagc catattcaac gggaaacgtc ttgctcgagg ccgcgattaa attccaacat 2400
ggatgctgat ttatatgggt ataaatgggc tcgcgataat gtcgggcaat caggtgcgac 2460
aatctatcga ttgtatggga agcccgatgc gccagagttg tttctgaaac atggcaaagg 2520
tagcgttgcc aatgatgtta cagatgagat ggtcagacta aactggctga cggaatttat 2580
gcctcttccg accatcaagc attttatccg tactcctgat gatgcatggt tactcaccac 2640
tgcgatcccc gggaaaacag cattccaggt attagaagaa tatcctgatt caggtgaaaa 2700
tattgttgat gcgctggcag tgttcctgcg ccggttgcat tcgattcctg tttgtaattg 2760
tccttttaac agcgatcgcg tatttcgtct cgctcaggcg caatcacgaa tgaataacgg 2820
tttggttgat gcgagtgatt ttgatgacga gcgtaatggc tggcctgttg aacaagtctg 2880
gaaagaaatg cataagcttt tgccattctc accggattca gtcgtcactc atggtgattt 2940
ctcacttgat aaccttattt ttgacgaggg gaaattaata ggttgtattg atgttggacg 3000
agtcggaatc gcagaccgat accaggatct tgccatccta tggaactgcc tcggtgagtt 3060
ttctccttca ttacagaaac ggctttttca aaaatatggt attgataatc ctgatatgaa 3120
taaattgcag tttcatttga tgctcgatga gtttttctaa tcagaattgg ttaattggtt 3180
gtaacactgg cagagcatta cgctgacttg acgggacggc ggctttgttg aataaatcga 3240
a 3241

<210> SEQ ID NO 32
<211> LENGTH: 6931
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 32
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120

```
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg agacaataac cctgataaat gcttcaataa tattgaaaaa ggaagagtat    600
gagtattcaa catttccgtg tcgcccttat tccctttttt gcggcatttt gccttcctgt    660
ttttgctcac ccagaaacgc tggtgaaagt aaaagatgct gaagatcagt tgggtgcacg    720
agtgggttac atcgaactgg atctcaacag cggtaagatc cttgagagtt ttcgccccga    780
agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataacac tgcggccaac ttacttctga caacgatcgg   1020
aggaccgaag gagctaaccg cttttttgca caacatgggg gatcatgtaa ctcgccttga   1080
tcgttgggaa ccggagctga atgaagccat accaaacgac gagcgtgaca ccacgatgcc   1140
tgcagcaatg gcaacaacgt tgcgcaaact attaactggc gaactactta ctctagcttc   1200
ccggcaacaa ttaatagact ggatggaggc ggataaagtt gcaggaccac ttctgcgctc   1260
ggcccttccg gctggctggt ttattgctga taaatctgga gccggtgagc gtgggtctcg   1320
cggtatcatt gcagcactgg ggccagatgg taagccctcc cgtatcgtag ttatctacac   1380
gacggggagt caggcaacta tggatgaacg aaatagacag atcgctgaga taggtgcctc   1440
actgattaag cattggtaac tgtcagacca agtttactca tatatacttt agattgattt   1500
aaaacttcat ttttaattta aaaggatcta ggtgaagatc ctttttgata atctcatgac   1560
caaaatccct taacgtgagt tttcgttcca ctgagcgtca gaccccgtag aaaagatcaa   1620
aggatcttct tgagatcctt tttttctgcg cgtaatctgc tgcttgcaaa caaaaaaacc   1680
accgctacca gcggtggttt gtttgccgga tcaagagcta ccaactcttt ttccgaaggt   1740
aactggcttc agcagagcgc agataccaaa tactgtcctt ctagtgtagc cgtagttagg   1800
ccaccacttc aagaactctg tagcaccgcc tacatacctc gctctgctaa tcctgttacc   1860
agtggctgct gccagtggcg ataagtcgtg tcttaccggg ttggactcaa gacgatagtt   1920
accggataag gcgcagcggt cgggctgaac ggggggttcg tgcacacagc ccagcttgga   1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100
cacgagggag cttccagggg gaaacgcctg gtatctttat agtcctgtcg ggtttcgcca   2160
cctctgactt gagcgtcgat ttttgtgatg ctcgtcaggg gggcggagcc tatggaaaaa   2220
cgccagcaac gcggcctttt tacggttcct ggccttttgc tggccttttg ctcacatgtt   2280
ctttcctgcg ttatcccctg attctgtgga taaccgtatt accgcctttg agtgagctga   2340
taccgctcgc cgcagccgaa cgaccgagcg cagcgagtca gtgagcgagg aagcggaaga   2400
gcgcctgatg cggtattttc tccttacgca tctgtgcggt atttcacacc gcatatatgg   2460
```

-continued

```
tgcactctca gtacaatctg ctctgatgcc gcatagttaa gccagtatac actccgctat   2520
cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
catcagcgtg gtcgtgaagc gattcacaga tgtctgcctg ttcatccgcg tccagctcgt   2760
tgagtttctc cagaagcgtt aatgtctggc ttctgataaa gcgggccatg ttaagggcgg   2820
tttttcctg tttggtcact gatgcctccg tgtaaggggg atttctgttc atgggggtaa   2880
tgataccgat gaaacgagag aggatgctca cgatacgggt tactgatgat gaacatgccc   2940
ggttactgga acgttgtgag ggtaaacaac tggcggtatg gatgcggcgg gaccagagaa   3000
aaatcactca gggtcaatgc cagcgcttcg ttaatacaga tgtaggtgtt ccacagggta   3060
gccagcagca tcctgcgatg cagatccgga acataatggt gcagggcgct gacttccgcg   3120
tttccagact ttacgaaaca cggaaaccga agaccattca tgttgttgct caggtcgcag   3180
acgttttgca gcagcagtcg cttcacgttc gctcgcgtat cggtgattca ttctgctaac   3240
cagtaaggca accccgccag cctagccggg tcctcaacga caggagcacg atcatgcgca   3300
cccgtggggc cgccatgccg gcgataatgg cctgcttctc gccgaaacgt ttggtggcgg   3360
gaccagtgac gaaggcttga gcgagggcgt gcaagattcc gaataccgca agcgacaggc   3420
cgatcatcgt cgcgctccag cgaaagcggt cctcgccgaa aatgacccag agcgctgccg   3480
gcacctgtcc tacgagttgc atgataaaga agacagtcat aagtgcggcg acgatagtca   3540
tgccccgcgc ccaccggaag gagctgactg ggttgaaggc tctcaagggc atcggtcgag   3600
atcccggtgc ctaatgagtg agctaactta cattaattgc gttgcgcgtg gtgaatgtga   3660
aaccagtaac gttatacgat gtcgcagagt atgccggtgt ctcttatcag accgtttccc   3720
gcgtggtgaa ccaggccagc cacgtttctg cgaaaacgcg ggaaaaagtg gaagcggcga   3780
tggcggagct gaattacatt cccaaccgcg tggcacaaca actggcgggc aaacagtcgt   3840
tgctgattgg cgttgccacc tccagtctgg ccctgcacgc gccgtcgcaa attgtcgcgg   3900
cgattaaatc tcgcgccgat caactgggtg ccagcgtggt ggtgtcgatg gtagaacgaa   3960
gcggcgtcga agcctgtaaa gcggcggtgc acaatcttct cgcgcaacgc gtcagtgggc   4020
tgatcattaa ctatccgctg gatgaccagg atgccattgc tgtggaagct gcctgcacta   4080
atgttccggc gttatttctt gatgtctctg accagacacc catcaacagt attattttct   4140
cccatgaaga cggtacgcga ctgggcgtgg agcatctggt cgcattgggt caccagcaaa   4200
tcgcgctgtt agcgggccca ttaagttctg tctcggcgcg tctgcgtctg gctggctggc   4260
ataaatatct cactcgcaat caaattcagc cgatagcgga acgggaaggc gactggagtg   4320
ccatgtccgg ttttcaacaa accatgcaaa tgctgaatga gggcatcgtt cccactgcga   4380
tgctggttgc caacgatcag atggcgctgg gcgcaatgcg cgccattacc gagtccgggc   4440
tgcgcgttgg tgcggatatc tcggtagtgg gatacgacga taccgaagac agctcatgtt   4500
atatcccgcc gttaaccacc atcaaacagg attttcgcct gctggggcaa accagcgtgg   4560
accgcttgct gcaactctct cagggccagg cggtgaaggg caatcagctg ttgcccgtct   4620
cactggtgaa aagaaaaacc accctggcgc ccaatacgca aaccgcctct ccccgcgcgt   4680
tggccgattc attaatgcag ctggcacgac aggtttcccg actggaaagc gggcagtgac   4740
ctgaattgac tctcttccgg gcgctatcat gccataccgc gaaaggtttt gcgccattcg   4800
atggtgtccg ggatctcgac gctctccctt atgcgactcc tgcattagga agcagcccag   4860
```

```
tagtaggttg aggccgttga gcaccgccgc cgcaaggaat ggtgcatgca aggagatggc   4920

gcccaacagt cccccggcca cggggcctgc caccataccc acgccgaaac aagcgctcat   4980

gagcccgaag tggcgagccc gatcttcccc atcggtgatg tcggcgatat aggcgccagc   5040

aaccgcacct gtggcgccgg tgatgccggc cacgatgcgt ccggcgtaga ggatcgagat   5100

ctcgatcccg cgaaattaat acgactcact ataggggaat tgtgagcgga taacaattcc   5160

cctctagagt ttgacagcat tatcatcgat ctcgagaaat cataaaaaat ttatttgctt   5220

tgtgagcgga taacaattat aatagattca attgtgagcg gataacaatt tcacacagaa   5280

ttcattaaag aggagaaatt acatatgcat catcaccatc accatcatca tcatcacgca   5340

agcagtaact tgattaaaca attgcaagag gacctgctgg cggaactgca atggcgtggc   5400

ctggttaatc agaccaccga cgaagatggc ctgcgtaaac tgctgaacga ggaacgtgtg   5460

accctgtatt gcggtttcga cccgaccgcg gatagcctgc acatcggcaa cctggcggcg   5520

attctgaccc tgcgtcgttt tcagcaagcg ggtcaccgtc cgatcgcgct ggttggtggt   5580

gcgaccggtc tgattggcga cccgagcggc aagaaaagcg agcgtaccct gaacgcgaag   5640

gaaaccgttg aagcgtggag cgcgcgtatc aaagaacagc tgggtcgttt cctggacttt   5700

gaggcggatg gcaacccggc gaagattaaa aacaactatg actggatcgg tccgctggat   5760

gtgattacct tcctgcgtga tgtgggcaag cactttagcg ttaactacat gatggcgaaa   5820

gagagcgttc agagccgtat cgaaaccggt attagcttca ccgagtttag ctacatgatg   5880

ctgcaagcgt atgacttcct gcgtctgtac gaaaccgaag gctgccgtct gcagatcggt   5940

ggcagcgatc aatggggtaa catcaccgcg ggcctggaac tgattcgtaa gaccaaaggt   6000

gaagcgcgtg cgtttggcct gaccatcccg ctggtgacca aggcggacgg taccaagttt   6060

ggcaaaaccg aaagcggtac catttggctg gataaggaga aaaccagccc gtacgaattc   6120

tatcagtttt ggatcaacac cgacgatcgt gacgttattc gttacctgaa gtatttcacc   6180

tttctgagca aagaggaaat cgaagcgctg gagcaggaac tgcgtgaggc gccggaaaag   6240

cgtgcggcgc aaaaagcgct ggcggaggaa gtgaccaaac tggttcacgg tgaggaagcg   6300

ctgcgtcagg cgatccgtat tagcgaagcg ctgtttagcg gtgatatcgc gaacctgacc   6360

gcggcggaga ttgaacaagg cttcaaggac gtgccgagct ttgttcacga aggtggcgat   6420

gtgccgctgg ttgagctgct ggttagcgcg ggtatcagcc cgagcaaacg tcaggcgcgt   6480

gaagacatcc aaaacggtgc gatttacgtg aacggcgagc gtctgcaaga tgttggcgcg   6540

attctgaccg cggaacaccg tctggaaggt cgttttaccg ttatccgtcg tggcaagaag   6600

aaatactatc tgattcgtta tgcgtaaaag cttaattagc tgagcttgga ctcctgttga   6660

tagatccagt aatgacctca gaactccatc tggatttgtt cagaacgctc ggttgccgcc   6720

gggcgttttt tattggtgag aatccaagct agcttggcgg cggccgcact cgagcaccac   6780

caccaccacc actgagatcc ggctgctaac aaagcccgaa aggaagctga gttggctgct   6840

gccaccgctg agcaataact agcataaccc cttggggcct ctaaacgggt cttgaggggt   6900

tttttgctga aaggaggaac tatatccgga t                                   6931
```

<210> SEQ ID NO 33
<211> LENGTH: 918
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"
<220> FEATURE:
<221> NAME/KEY: modified_base
<222> LOCATION: (91)..(93)
<223> OTHER INFORMATION: a, c, t, g, unknown or other
<220> FEATURE:
<221> NAME/KEY: modified_base
<222> LOCATION: (190)..(192)
<223> OTHER INFORMATION: a, c, t, g, unknown or other
<220> FEATURE:
<221> NAME/KEY: modified_base
<222> LOCATION: (205)..(207)
<223> OTHER INFORMATION: a, c, t, g, unknown or other
<220> FEATURE:
<221> NAME/KEY: modified_base
<222> LOCATION: (319)..(324)
<223> OTHER INFORMATION: a, c, t, g, unknown or other
<220> FEATURE:
<221> NAME/KEY: modified_base
<222> LOCATION: (460)..(462)
<223> OTHER INFORMATION: a, c, t, g, unknown or other
<220> FEATURE:
<221> NAME/KEY: modified_base
<222> LOCATION: (469)..(474)
<223> OTHER INFORMATION: a, c, t, g, unknown or other
<220> FEATURE:
<221> NAME/KEY: modified_base
<222> LOCATION: (481)..(483)
<223> OTHER INFORMATION: a, c, t, g, unknown or other

<400> SEQUENCE: 33
gacgaatttg aaatgataaa gagaaacaca tctgaaatta tcagcgagga agagttaaga 60
gaggttttaa aaaaagatga aaaatctgct nnnataggtt ttgaaccaag tggtaaaata 120
catttagggc attatctcca aataaaaaag atgattgatt tacaaaatgc tggatttgat 180
ataattatan nnttggctga tttannngcc tatttaaacc agaaaggaga gttggatgag 240
attagaaaaa taggagatta taacaaaaaa gtttttgaag caatggggtt aaaggcaaaa 300
tatgtttatg gaagtgaann nnnncttgat aaggattata cactgaatgt ctatagattg 360
gctttaaaaa ctaccttaaa aagagcaaga aggagtatgg aacttatagc aagagaggat 420
gaaaatccaa aggttgctga agttatctat ccaataatgn nngttaatnn nnnncattat 480
nnnggcgttg atgttgcagt tggagggatg gagcagagaa aaatacacat gttagcaagg 540
gagcttttac caaaaaaggt tgtttgtatt cacaaccctg tcttaacggg tttggatgga 600
gaaggaaaga tgagttcttc aaaagggaat tttatagctg ttgatgactc tccagaagag 660
attagggcta agataaagaa agcatactgc ccagctggag ttgttgaagg aaatccaata 720
atggagatag ctaaatactt ccttgaatat cctttaacca taaaaaggcc agaaaaattt 780
ggtggagatt tgacagttaa tagctatgag gagttagaga gtttatttaa aaataaggaa 840
ttgcatccaa tggatttaaa aaatgctgta gctgaagaac ttataaagat tttagagcca 900
attagaaaga gattataa 918

<210> SEQ ID NO 34
<211> LENGTH: 1272
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 34
gcaagcagta acttgattaa acaattgcaa gagcgggggc tggtagccca ggtgacggac 60
gaggaagcgt tagcagagcg actggcgcaa ggcccgatcg cgctctattg cggcttcgat 120

```
cctaccgctg acagcttgca tttggggcat cttgttccat tgttatgcct gaaacgcttc    180

cagcaggcgg gccacaagcc ggttgcgctg gtaggcggcg cgacgggtct gattggcgac    240

ccgagcttca aagctgccga gcgtaagctg aacaccgaag aaactgttca ggagtgggtg    300

gacaaaatcc gtaagcaggt tgccccgttc ctcgatttcg actgtggaga aaactctgct    360

atcgcggcga acaactatga ctggttcggc aatatgaatg tgctgacctt cctgcgcgat    420

attggcaaac acttctccgt taaccagatg atcaacaaag aagcggttaa gcagcgtctc    480

aaccgtgaag atcaggggat ttcgttcact gagttttcct acaacctgtt gcagggttat    540

gacttcgcat gtctgaacaa acagtacggt gtggtgctgc aaattggtgg ttctgaccag    600

tggggtaaca tcacttctgg tatcgacctg acccgtcgtc tgcatcagaa tcaggtgttt    660

ggcctgaccg ttccgctgat cactaaagca gatggcacca aatttggtaa aactgaaggc    720

ggcgcagtct ggttagatcc gaagaaaacc agcccgtaca aattctacca gttctggatc    780

aacactgcgg acgccgacgt ttaccgcttc ctgaagttct tcacctttat gagcattgaa    840

gagatcaacg ccctggaaga agaagataaa aacagcggta aagcaccgcg cgcccagtat    900

gtactggcgg agcaggtgac tcgtctggtt cacggtgaag aaggtttaca ggcggcaaaa    960

cgtattaccg aatgcctgtt cagcggttct ttgagtgcgc tgagtgaagc ggacttcgaa   1020

cagctggcgc aggacggcgt accgatggtt gagatggaaa agggcgcaga cctgatgcag   1080

gcactggtcg attctgaact gcaaccttcc cgtggtcagg cacgtaaaac tatcgcctcc   1140

aatgccatca ccattaacgg tgaaaaacag tccgatcctg aatacttctt taaagaagaa   1200

gatcgtctgt ttggtcgttt taccttactg cgtcgcggta aaaagaatta ctgtctgatt   1260

tgctggaaat aa                                                        1272
```

<210> SEQ ID NO 35
<211> LENGTH: 1266
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 35

```
gcaagcagta acttgattaa acaattgcaa gagcgggggc tggtagccca ggtgacggac     60

gaggaagcgt tagcagagcg actggcgcaa ggcccgatcg cgctctattg cggcttcgat    120

cctaccgctg acagcttgca tttggggcat cttgttccat tgttatgcct gaaacgcttc    180

cagcaggcgg gtcaccgtcc gatcgcgctg gttggtggtg cgaccggtct gattggcgac    240

ccgagcggca agaaaagcga gcgtaccctg aacgcgaagg aaaccgttga agcgtggagc    300

gcgcgtatca aagaacagct gggtcgtttc ctggactttg aggcggatgg caacccggcg    360

aagattaaaa acaactatga ctggatcggt ccgctggatg tgattacctt cctgcgtgat    420

gtgggcaagc actttagcgt taactacatg atggcgaaag agagcgttca gagccgtatc    480

gaaaccggta ttagcttcac cgagtttagc tacatgatgc tgcaagcgta tgatttcctg    540

cgtctgtacg aaaccgaagg ctgccgtctg cagatcggtg gcagcgatca atggggtaac    600

atcaccgcgg gcctggaact gattcgtaag accaaaggtg aagcgcgtgc gtttggcctg    660

accatcccgc tggtgaccaa ggcggacggt accaagtttg gcaaaaccga aagcggtacc    720

atttggctgg ataaggagaa aaccagcccg tacgaattct atcagttttg gatcaacacc    780
```

```
gacgatcgtg acgttattcg ttacctgaag tatttcacct ttctgagcaa agaggaaatc    840

gaagcgctgg agcaggaact gcgtgaggcg ccggaaaagc gtgcggcgca aaaagcgctg    900

gcggaggaag tgaccaaact ggttcacggt gaggaagcgc tgcgtcaggc gatccgtatt    960

agcgaagcgc tgtttagcgg tgatatcgcg aacctgaccg cggcggagat tgaacaaggc   1020

ttcaaggacg tgccgagctt tgttcacgaa ggtggcgatg tgccgctggt tgagctgctg   1080

gttagcgcgg gtatcagccc gagcaaacgt caggcgcgtg aagacatcca aaacggtgcg   1140

atttacgtga acggcgagcg tctgcaagat gttggcgcga ttctgaccgc ggaacaccgt   1200

ctggaaggtc gttttaccgt tatccgtcgt ggcaagaaga aatactatct gattcgttat   1260

gcgtaa                                                              1266
```

<210> SEQ ID NO 36
<211> LENGTH: 1272
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 36

```
gcaagcagta acttgattaa acaattgcaa gagcgggggc tggtagccca ggtgacggac     60

gaggaagcgt tagcagagcg actggcgcaa ggcccgatcg cgctctattg cggcttcgat    120

cctaccgctg acagcttgca tttggggcat cttgttccat tgttatgcct gaaacgcttc    180

cagcaggcgg gccacaagcc ggttgcgctg gtaggcggcg cgacgggtct gattggcgac    240

ccgagtttca aagctgccga gcgtaagctg aacaccgaag aaactgttca ggagtgggtg    300

gacaaaatcc gtaagcaggt tgccccgttc ctcgatttcg actgtggaga aaactctgct    360

atcgcggcga acaactatga ctggttcggc aatatgaatg tgctgacctt cctgcgcgat    420

attggcaaac acttctccgt taaccagatg atcaacaaag aagcggttaa gcagcgtctc    480

aaccgtgaag atcaggggat ttcgttcact gagttttcct acagcctgtt gcagggttat    540

gacttcgcct gtctgaacaa acagtacggt gtggtgctgc aaattggtgg ttctgaccag    600

tggggtaaca tcacttctgg tatcgacctg acccgtcgtc tgcatcagaa tcaggtgttt    660

ggcctgaccg ttccgctgat cactaaagca gatggcacca aatttggcaa aaccgaaagc    720

ggtaccattt ggctggataa ggagaaaacc agcccgtacg aattctatca gttttggatc    780

aacaccgacg atcgtgacgt tattcgttac ctgaagtatt tcacctttct gagcaaagag    840

gaaatcgaag cgctggagca ggaactgcgt gaggcgccgg aaaagcgtgc ggcgcaaaaa    900

gcgctggcgg aggaagtgac caaactggtt cacggtgagg aagcgctgcg tcaggcgatc    960

cgtattagcg aagcgctgtt tagcggtgat atcgcgaacc tgaccgcggc ggagattgaa   1020

caaggcttca aggacgtgcc gagctttgtt cacgaaggtg gcgatgtgcc gctggttgag   1080

ctgctggtta gcgcgggtat cagcccgagc aaacgtcagg cgcgtgaaga catccaaaac   1140

ggtgcgattt acgtgaacgg cgagcgtctg caagatgttg gcgcgattct gaccgcggaa   1200

caccgtctgg aaggtcgttt taccgttatc cgtcgtggca agaagaaata ctatctgatt   1260

cgttatgcgt aa                                                       1272
```

<210> SEQ ID NO 37
<211> LENGTH: 13907
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 37

```
ttctctgtca cagaatgaaa atttttctgt catctcttcg ttattaatgt ttgtaattga     60
ctgaatatca acgcttattt gcagcctgaa tggcgaatgg gacgcgccct gtagcggcgc    120
attaagcgcg gcgggtgtgg tggttacgcg cagcgtgacc gctacacttg ccagcgccct    180
agcgcccgct cctttcgctt tcttcccttc ctttctcgcc acgttcgccg gctttccccg    240
tcaagctcta aatcgggggc tccctttagg gttccgattt agtgctttac ggcacctcga    300
ccccaaaaaa cttgattagg gtgatggttc acgtagtggg ccatcgccct gatagacggt    360
ttttcgccct ttgacgttgg agtccacgtt ctttaatagt ggactcttgt tccaaactgg    420
aacaacactc aaccctatct cggtctattc ttttgattta taagggattt tgccgatttc    480
ggcctattgg ttaaaaaatg agctgattta acaaaaattt aacgcgaatt ttaacaaaat    540
attaacgttt acaatttcag gtggcacttt tcggggaaat gtgcgcggaa cccctatttg    600
tttatttttc taaatacatt caaatatgta tccgctcatg agacaataac cctgataaat    660
gcttcaataa tattgaaaaa ggaagagtat gagtattcaa catttccgtg tcgcccttat    720
tccctttttt gcggcatttt gccttcctgt ttttgctcac ccagaaacgc tggtgaaagt    780
aaaagatgct gaagatcagt tgggtgcacg agtgggttac atcgaactgg atctcaacag    840
cggtaagatc cttgagagtt ttcgccccga agaacgtttt ccaatgatga gcacttttaa    900
agttctgcta tgtggcgcgg tattatcccg tattgacgcc gggcaagagc aactcggtcg    960
ccgcatacac tattctcaga atgacttggt tgagtactca ccagtcacag aaaagcatct   1020
tacggatggc atgacagtaa gagaattatg cagtgctgcc ataaccatga gtgataacac   1080
tgcggccaac ttacttctga caacgatcgg aggaccgaag gagctaaccg cttttttgca   1140
caacatgggg gatcatgtaa ctcgccttga tcgttgggaa ccggagctga atgaagccat   1200
accaaacgac gagcgtgaca ccacgatgcc tgtagcaatg gcaacaacgt tgcgcaaact   1260
attaactggc gaactactta ctctagcttc ccggcaacaa ttaatagact ggatggaggc   1320
ggataaagtt gcaggaccac ttctgcgctc ggcccttccg gctggctggt ttattgctga   1380
taaatctgga gccggtgagc gtgggtctcg cggtatcatt gcagcactgg ggccagatgg   1440
taagccctcc cgtatcgtag ttatctacac gacggggagt caggcaacta tggatgaacg   1500
aaatagacag atcgctgaga taggtgcctc actgattaag cattggtaac tgtcagacca   1560
agtttactca tatatacttt agattgattt aaaacttcat ttttaattta aaaggatcta   1620
ggtgaagatc ctttttgata atctcatgac caaaatccct taacgtgagt tttcgttcca   1680
ctgagcgtca gaccccgtag aaaagatcaa aggatcttct tgagatcctt tttttctgcg   1740
cgtaatctgc tgcttgcaaa caaaaaaacc accgctacca gcggtggttt gtttgccgga   1800
tcaagagcta ccaactcttt ttccgaaggt aactggcttc agcagagcgc agataccaaa   1860
tactgtcctt ctagtgtagc cgtagttagg ccaccacttc aagaactctg tagcaccgcc   1920
tacatacctc gctctgctaa tcctgttacc agtggctgct gccagtggcg ataagtcgtg   1980
tcttaccggg ttggactcaa gacgatagtt accggataag gcgcagcggt cgggctgaac   2040
ggggggttcg tgcacacagc ccagcttgga gcgaacgacc tacaccgaac tgagatacct   2100
acagcgtgag cattgagaaa gcgccacgct tcccgaaggg agaaaggcgg acaggtatcc   2160
```

```
ggtaagcggc agggtcggaa caggagagcg cacgagggag cttccagggg gaaacgcctg   2220
gtatctttat agtcctgtcg ggtttcgcca cctctgactt gagcgtcgat ttttgtgatg   2280
ctcgtcaggg gggcggagcc tatggaaaaa cgccagcaac gcggcctttt tacggttcct   2340
ggccttttgc tggccttttg ctcacatgtt ctttcctgcg ttatcccctg attctgtgga   2400
taaccgtatt accgcctttg agtgagctga taccgctcgc cgcagccgaa cgaccgagcg   2460
cagcgagtca gtgagcgagg aagcggaaga gcgcctgatg cggtattttc tccttacgca   2520
tctgtgcggt atttcacacc gcagaccagc cgcgtaacct ggcaaaatcg gttacggttg   2580
agtaataaat ggatgccctg cgtaagcggg tgtgggcgga caataaagtc ttaaactgaa   2640
caaaatagat ctaaactatg acaataaagt cttaaactag acagaatagt tgtaaactga   2700
aatcagtcca gttatgctgt gaaaaagcat actggacttt tgttatggct aaagcaaact   2760
cttcattttc tgaagtgcaa attgcccgtc gtattaaaga ggggcgtggc caagggcatg   2820
gtaaagacta tattcgcggc gttgtgacaa tttaccgaac aactccgcgg ccgggaagcc   2880
gatctcggct tgaacgaatt gatgttacgc agcagcaacg atgttacgca gcagggcagt   2940
cgccctaaaa caaagttagg tggctcaagt atgggcatca ttcgcacatg taggctcggc   3000
cctgaccaag tcaaatccat gcgggctgct cttgatcttt tcggtcgtga gttcggagac   3060
gtagccacct actcccaaca tcagccggac tccgattacc tcgggaactt gctccgtagt   3120
aagacattca tcgcgcttgc tgccttcgac caagaagcgg ttgttggcgc tctcgcggct   3180
tacgttctgc ccaggtttga gcagccgcgt agtgagatct atatctatga tctcgcagtc   3240
tccggcgagc accggaggca gggcattgcc accgcgctca tcaatctcct caagcatgag   3300
gccaacgcgc ttggtgctta tgtgatctac gtgcaagcag attacggtga cgatcccgca   3360
gtggctctct atacaaagtt gggcatacgg gaagaagtga tgcactttga tatcgaccca   3420
agtaccgcca cctaacgttg ctgctccata acatcaaaca tcgacccacg gcgtaacgcg   3480
cttgctgctt ggatgcccga ggcatagact gtacaaaaaa acagtcataa caagccatga   3540
aaaccgccac tgcgccgtta ccaccgctgc gttcggtcaa ggttctggac cagttgcgtg   3600
agcgcatacg ctacttgcat tacagtttac gaaccgaaca ggcttatgtc aactgggttc   3660
gtgccttcat ccgtttccac ggtgtgcgtc acccggcaac cttgggcagc agcgaagtcg   3720
aggcatttct gtcctggctg gcgaacgagc gcaaggtttc ggtctccacg catcgtcagg   3780
cattggcggc cttgctgttc ttctacggca aggtgctgtg cacggatctg ccctggcttc   3840
aggagatcgg tagacctcgg ccgtcgcggc gcttgccggt ggtgctgacc ccggatgaag   3900
tggttcgcat cctcggtttt ctggaaggcg agcatcgttt gttcgcccag gactctagct   3960
atagttctag tggttggcta cgtacccgta gtggctatgg cagggcttgc gcttaatgcg   4020
ccgctacagg gcgcgtgggg atacccccta gagccccagc tggttctttc cgcctcagaa   4080
gccatagagc ccaccgcatc cccagcatgc ctgctattgt cttcccaatc ctcccccttg   4140
ctgtcctgcc ccaccccacc ccccagaata gaatgacacc tactcagaca atgcgatgca   4200
atttcctcat tttattagga aaggacagtg ggagtggcac cttccagggt caaggaaggc   4260
acgggggagg ggcaaacaac agatggctgg caactagaag gcacagtcga ggctgatcag   4320
cgggtttaaa cgggccctct agactcgagt taaagtcgac ttaacgcgtt gaattcttac   4380
gcataacgaa tcagatagta tttcttcttg ccacgacgga taacggtaaa acgaccttcc   4440
agacggtgtt ccgcggtcag aatcgcgcca acatcttgca gacgctcgcc gttcacgtaa   4500
atcgcaccgt tttggatgtc ttcacgcgcc tgacgtttgc tcgggctgat acccgcgcta   4560
```

```
accagcagct caaccagcgg cacatcgcca ccttcgtgaa caaagctcgg cacgtccttg   4620
aagccttgtt caatctccgc cgcggtcagg ttcgcgatat caccgctaaa cagcgcttcg   4680
ctaatacgga tcgcctgacg cagcgcttcc tcaccgtgaa ccagtttggt cacttcctcc   4740
gccagcgctt tttgcgccgc acgcttttcc ggcgcctcac gcagttcctg ctccagcgct   4800
tcgatttcct ctttgctcag aaaggtgaaa tacttcaggt aacgaataac gtcacgatcg   4860
tcggtgttga tccaaaactg atagaattcg tacgggctgg ttttctcctt atccagccaa   4920
atggtaccgc tttcggtttt gccaaacttg gtaccgtccg ccttggtcac cagcgggatg   4980
gtcaggccaa acgcacgcgc ttcacctttg gtcttacgaa tcagttccag gcccgcggtg   5040
atgttacccc attgatcgct gccaccgatc tgcagacggc agccttcggt ttcgtaggca   5100
cgcaggaaac catacgcttg cagcatcatg tagctaaact cggtgaagct aataccggtt   5160
tcgatacggc tctgaacgct ctctttcgcc atcatgtagt taacgctaaa gtgcttgccc   5220
acatcacgca ggaaggtaat cacatccagc ggaccgatcc agtcatagtt gtttttaatc   5280
ttcgccgggt tgccatccgc ctcaaagtcc aggaaacgac ccagctgttc tttgatacgc   5340
gcgctccacg cttcaacggt ttccttcgcg ttcagggtac gctcgctttt cttgccgctc   5400
gggtcgccaa tcagaccggt cgcaccacca accagcgcga tcggacggtg acccgcttgc   5460
tgaaaacgac gcagggtcag aatcgccgcc aggttgccga tgtgcaggct atccgcggtc   5520
gggtcgaaac cgcaacccag ggtcacacgt tcctcgttca gcagtttacg caggccatct   5580
tcgtcggtgg tctgattaac caggccacgc cattgcagtt ccgccagcag gtccatggtg   5640
gcgctagcca gcttgggtct ccctatagtg agtcgtatta atttcgataa gccagtaagc   5700
agtgggttct ctagttagcc agagagctct agaccaagtg acgatcacag cgatccacaa   5760
acaagaaccg cgacccaaat cccggctgcg acggaactag ctgtgccaca cccggcgcgt   5820
ccttatataa tcatcggcgt tcaccgcccc acggagatcc ctccgcagaa tcgccgagaa   5880
gggactactt ttcctcgcct gttccgctct ctggaaagaa aaccagtgcc ctagagtcac   5940
ccaagtcccg tcctaaaatg tccttctgct gatactgggg ttctaaggcc gagtcttatg   6000
agcagcgggc cgctgtcctg agcgtccggg cggaaggatc aggacgctcg ctgcgccctt   6060
cgtctgacgt ggcagcgctc gccgtgagga gggggcgcc cgcgggaggc gccaaaaccc   6120
ggcgcggagg ccttcgaacg gccactagca aaaaatggag ggggacggat tcgaaccgcc   6180
gaacccaaag ggagcggatt tgaagtccgc cgcgtttagc cacttcgcta cccctccggg   6240
gatctgtggt ctcatacaga acttataaga ttcccaaatc caaagacatt tcacgtttat   6300
ggtgatttcc cagaacacat agcgacatgc aaatattgca gggcgccact cccctgtccc   6360
tcacagccat cttcctgcca gggcgcacgc gcgctgggtg ttcccgccta gtgacactgg   6420
gcccgcgatt ccttggagcg ggttgatgac gtcagcgttc gaattcctag caaaaaatgg   6480
tgggggaagg attcgaacct tcgaagtctg tgacggcaga tttgaagtct gctccctttg   6540
gccgctcggg aaccccaccg gtgtttcgtc ctttccacaa gatatataaa gccaagaaat   6600
cgaaatactt tcaagttacg gtaagcatat gatagtccat tttaaaacat aattttaaaa   6660
ctgcaaacta cccaagaaat tattactttc tacgtcacgt attttgtact aatatctttg   6720
tgtttacagt caaattaatt ctaattatct ctctaacagc cttgtatcgt atatgcaaat   6780
atgaaggaat catgggaaat aggccctctt cctgcccgac ctagcaaaaa atggaggggg   6840
acggattcga accgccgaac ccaaagggag cggatttgaa gtccgccgcg tttagccact   6900
```

```
tcgctacccc tccggggatc tgtggtctca tacagaactt ataagattcc caaatccaaa   6960
gacatttcac gtttatggtg atttcccaga acacatagcg acatgcaaat attgcagggc   7020
gccactcccc tgtccctcac agccatcttc ctgccagggc gcacgcgcgc tgggtgttcc   7080
cgcctagtga cactgggccc gcgattcctt ggagcgggtt gatgacgtca gcgttcgaat   7140
tcctagcaaa aaatggtggg ggaaggattc gaaccttcga agtctgtgac ggcagatttg   7200
aagtctgctc cctttggccg ctcgggaacc ccaccggtgt ttcgtccttt ccacaagata   7260
tataaagcca agaaatcgaa atactttcaa gttacggtaa gcatatgata gtccatttta   7320
aaacataatt ttaaaactgc aaactaccca agaaattatt actttctacg tcacgtattt   7380
tgtactaata tctttgtgtt tacagtcaaa ttaattctaa ttatctctct aacagccttg   7440
tatcgtatat gcaaatatga aggaatcatg ggaaataggc cctcttcctg cccgacctag   7500
caaaaaatgg agggggacgg attcgaaccg ccgaacccaa agggagcgga tttgaagtcc   7560
gccgcgttta gccacttcgc taccccctccg gggatctgtg gtctcataca gaacttataa   7620
gattcccaaa tccaaagaca tttcacgttt atggtgattt cccagaacac atagcgacat   7680
gcaaatattg cagggcgcca ctcccctgtc cctcacagcc atcttcctgc cagggcgcac   7740
gcgcgctggg tgttcccgcc tagtgacact gggcccgcga ttccttggag cgggttgatg   7800
acgtcagcgt tcgaattcct agcaaaaaat ggtgggggaa ggattcgaac cttcgaagtc   7860
tgtgacggca gatttgaagt ctgctccctt tggccgctcg ggaaccccac cggtgtttcg   7920
tcctttccac aagatatata aagccaagaa atcgaaatac tttcaagtta cggtaagcat   7980
atgatagtcc attttaaaac ataattttaa aactgcaaac tacccaagaa attattactt   8040
tctacgtcac gtattttgta ctaatatctt tgtgtttaca gtcaaattaa ttctaattat   8100
ctctctaaca gccttgtatc gtatatgcaa atatgaagga atcatgggaa ataggccctc   8160
ttcctgcccg acctagcaaa aaaggagggg tagcgaagtg gctaaacgcg gcggacttca   8220
aatccgctcc ctttgggttc ggcggttcga atccgtcccc ctccagggga tctgtggtct   8280
catacagaac ttataagatt cccaaatcca aagacatttc acgtttatgg tgatttccca   8340
gaacacatag cgacatgcaa atattgcagg gcgccactcc cctgtccctc acagccatct   8400
tcctgccagg gcgcacgcgc gctgggtgtt cccgcctagt gacactgggc ccgcgattcc   8460
ttggagcggg ttgatgacgt cagcgttcga attcctagca aaaaatggtg ggggaaggat   8520
tcgaaccttc gaagtctgtg acggcagatt tgaagtctgc tccctttggc cgctcgggaa   8580
ccccaccggt gtttcgtcct ttccacaaga tatataaagc caagaaatcg aaatactttc   8640
aagttacggt aagcatatga tagtccattt taaaacataa ttttaaaact gcaaactacc   8700
caagaaatta ttactttcta cgtcacgtat tttgtactaa tatctttgtg tttacagtca   8760
aattaattct aattatctct ctaacagcct tgtatcgtat atgcaaatat gaaggaatca   8820
tgggaaatag gccctcttcc tgcccgacct agcaaaaaag gaggggtagc gaagtggcta   8880
aacgcggcgg acttcaaatc cgctcccttt gggttcggcg gttcgaatcc gtccccctcc   8940
aggggatctg tggtctcata cagaacttat aagattccca aatccaaaga catttcacgt   9000
ttatggtgat ttcccagaac acatagcgac atgcaaatat tgcagggcgc cactcccctg   9060
tccctcacag ccatcttcct gccagggcgc acgcgcgctg ggtgttcccg cctagtgaca   9120
ctgggcccgc gattccttgg agcgggttga tgacgtcagc gttcgaattc ctagcaaaaa   9180
atggtggggg aaggattcga accttcgaag tctgtgacgg cagatttgaa gtctgctccc   9240
tttggccgct cgggaacccc accggtgttt cgtcctttcc acaagatata taaagccaag   9300
```

```
aaatcgaaat actttcaagt tacggtaagc atatgatagt ccattttaaa acataatttt   9360
aaaactgcaa actacccaag aaattattac tttctacgtc acgtattttg tactaatatc   9420
tttgtgttta cagtcaaatt aattctaatt atctctctaa cagccttgta tcgtatatgc   9480
aaatatgaag gaatcatggg aaataggccc tcttcctgcc cgacctagca aaaaatggag   9540
ggggacggat tcgaaccgcc gaacccaaag ggagcggatt tgaagtccgc cgcgtttagc   9600
cacttcgcta cccctccggg gatctgtggt ctcatacaga acttataaga ttcccaaatc   9660
caaagacatt tcacgtttat ggtgatttcc cagaacacat agcgacatgc aaatattgca   9720
gggcgccact cccctgtccc tcacagccat cttcctgcca gggcgcacgc gcgctgggtg   9780
ttcccgccta gtgacactgg gcccgcgatt ccttggagcg ggttgatgac gtcagcgttc   9840
gaattcctag caaaaaatgg tgggggaagg attcgaacct tcgaagtctg tgacggcaga   9900
tttgaagtct gctccctttg gccgctcggg aaccccaccg gtgtttcgtc ctttccacaa   9960
gatatataaa gccaagaaat cgaaatactt tcaagttacg gtaagcatat gatagtccat  10020
tttaaaacat aattttaaaa ctgcaaacta cccaagaaat tattactttc tacgtcacgt  10080
attttgtact aatatctttg tgtttacagt caaattaatt ctaattatct ctctaacagc  10140
cttgtatcgt atatgcaaat atgaaggaat catgggaaat aggccctctt cctgcccgac  10200
ctagcaaaaa aggaggggta gcgaagtggc taaacgcggc ggacttcaaa tccgctccct  10260
ttgggttcgg cggttcgaat ccgtcccccct ccaggggatc tgtggtctca tacagaactt  10320
ataagattcc caaatccaaa gacatttcac gtttatggtg atttcccaga acacatagcg  10380
acatgcaaat attgcagggc gccactcccc tgtccctcac agccatcttc ctgccagggc  10440
gcacgcgcgc tgggtgttcc cgcctagtga cactgggccc gcgattcctt ggagcgggtt  10500
gatgacgtca gcgttcgaat tcctagcaaa aaatggtggg ggaaggattc gaaccttcga  10560
agtctgtgac ggcagatttg aagtctgctc cctttggccg ctcgggaacc ccaccggtgt  10620
ttcgtccttt ccacaagata tataaagcca agaaatcgaa atactttcaa gttacggtaa  10680
gcatatgata gtccatttta aaacataatt ttaaaactgc aaactaccca agaaattatt  10740
actttctacg tcacgtattt tgtactaata tctttgtgtt tacagtcaaa ttaattctaa  10800
ttatctctct aacagccttg tatcgtatat gcaaatatga aggaatcatg ggaaataggc  10860
cctcttcctg cccgacctag caaaaaagga ggggtagcga agtggctaaa cgcggcggac  10920
ttcaaatccg ctccctttgg gttcggcggt tcgaatccgt cccccctccag gggatctgtg  10980
gtctcataca gaacttataa gattcccaaa tccaaagaca tttcacgttt atggtgattt  11040
cccagaacac atagcgacat gcaaatattg cagggcgcca ctcccctgtc cctcacagcc  11100
atcttcctgc cagggcgcac gcgcgctggg tgttcccgcc tagtgacact gggcccgcga  11160
ttccttggag cgggttgatg acgtcagcgt tcgaattcct agcaaaaaat ggtgggggaa  11220
ggattcgaac cttcgaagtc tgtgacggca gatttgaagt ctgctccctt tggccgctcg  11280
ggaaccccac cggtgtttcg tcctttccac aagatatata aagccaagaa atcgaaatac  11340
tttcaagtta cggtaagcat atgatagtcc attttaaaac ataattttaa aactgcaaac  11400
tacccaagaa attattactt tctacgtcac gtattttgta ctaatatctt tgtgtttaca  11460
gtcaaattaa ttctaattat ctctctaaca gccttgtatc gtatatgcaa atatgaagga  11520
atcatgggaa ataggccctc ttcctgcccg acctagtcaa taatcaatgt caacgcgtat  11580
atctggcccg tacatcgcga agcagcgcaa aacggatcct gcaggtattt gcggccgcgg  11640
```

```
tccgtatact ccggaatatt aatagatcat ggagataatt aaaatgataa ccatctcgca  11700

aataaataag tattttactg ttttcgtaac agttttgtaa taaaaaaacc tataaatatt  11760

ccggattatt cataccgtcc caccatcggg cgcgaactcc taaaaaaccg ccaccatgaa  11820

gtgccttttg tacttagcct ttttattcat tggggtgaat tgcaagttca ccatagtttt  11880

tccacacaac caaaaaggaa actggaaaaa tgttccttct aattaccatt attgcccgtc  11940

aagctcagat ttaaattggc ataatgactt aataggcaca gccttacaag tcaaaatgcc  12000

caagagtcac aaggctattc aagcagacgg ttggatgtgt catgcttcca aatgggtcac  12060

tacttgtgat ttccgctggt atggaccgaa gtatataaca cattccatcc gatccttcac  12120

tccatctgta gaacaatgca aggaaagcat tgaacaaacg aaacaaggaa cttggctgaa  12180

tccaggcttc cctcctcaaa gttgtggata tgcaactgtg acggatgccg aagcagtgat  12240

tgtccaggtg actcctcacc atgtgctggt tgatgaatac acaggagaat gggttgattc  12300

acagttcatc aacggaaaat gcagcaatta catatgcccc actgtccata actctacaac  12360

ctggcattct gactataagg tcaaagggct atgtgattct aacctcattt ccatggacat  12420

caccttcttc tcagaggacg gagagctatc atccctggga aaggagggca cagggttcag  12480

aagtaactac tttgcttatg aaactggagg caaggcctgc aaaatgcaat actgcaagca  12540

ttggggagtc agactcccat caggtgtctg gttcgagatg gctgataagg atctctttgc  12600

tgcagccaga ttccctgaat gcccagaagg gtcaagtatc tctgctccat ctcagacctc  12660

agtggatgta agtctaattc aggacgttga gaggatcttg gattattccc tctgccaaga  12720

aacctggagc aaaatcagag cgggtcttcc aatctctcca gtggatctca gctatcttgc  12780

tcctaaaaac ccaggaaccg gtcctgcttt caccataatc aatggtaccc taaaatactt  12840

tgagaccaga tacatcagag tcgatattgc tgctccaatc ctctcaagaa tggtcggaat  12900

gatcagtgga actaccacag aaagggaact gtgggatgac tggggcacccat atgaagacgt  12960

ggaaattgga cccaatggag ttctgaggac cagttcagga tataagtttc ctttatacat  13020

gattggacat ggtatgttgg actccgatct tcatcttagc tcaaaggctc aggtgttcga  13080

acatcctcac attcaagacg ctgcttcgca acttcctgat gatgagagtt tatttttttgg  13140

tgatactggg ctatccaaaa atccaatcga gcttgtagaa ggttggttca gtagttggaa  13200

aagctctatt gcctcttttt tctttatcat agggttaatc attggactat tcttggttct  13260

ccgagttggt atccatcttt gcattaaatt aaagcacacc aagaaaagac agatttatac  13320

agacatagag atgaaccgac ttggaaagtg ataaggccag gccggccaag cttgtcgaga  13380

agtactagag gatcataatc agccatacca catttgtaga ggttttactt gctttaaaaa  13440

acctcccaca cctccccctg aacctgaaac ataaaatgaa tgcaattgtt gttgttaact  13500

tgtttattgc agcttataat ggttacaaat aaagcaatag catcacaaat ttcacaaata  13560

aagcattttt ttcactgcat tctagttgtg gtttgtccaa actcatcaat gtatcttatc  13620

atgtctggat ctgatcactg cttgagccta ggagatccga accagataag tgaaatctag  13680

ttccaaacta ttttgtcatt tttaattttc gtattagctt acgacgctac acccagttcc  13740

catctatttt gtcactcttc cctaaataat ccttaaaaac tccatttcca cccctcccag  13800

ttcccaacta ttttgtccgc ccacagcggg gcatttttct tcctgttatg tttttaatca  13860

aacatcctgc caactccatg tgacaaaccg tcatcttcgg ctacttt               13907
```

```
<210> SEQ ID NO 38
<211> LENGTH: 1275
```

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 38

```
atggcaagca gtaacttgat taaacaattg caagagcggg ggctggtagc ccaggtgacg     60

gacgaggaag cgttagcaga gcgactggcg caaggcccga tcgcgctcgg ttgcggcttc    120

gatcctaccg ctgacagctt gcatttgggg catcttgttc cattgttatg cctgaaacgc    180

ttccagcagg cgggccacaa gccggttgcg ctggtaggcg gcgcgacggg tctgattggc    240

gacccgagct tcaaagctgc cgagcgtaag ctgaacaccg aagaaactgt tcaggagtgg    300

gtggacaaaa tccgtaagca ggttgccccg ttcctcgatt tcgactgtgg agaaaactct    360

gctatcgcgg cgaacaacta tgactggttc ggcaatatga atgtgctgac cttcctgcgc    420

gatattggca aacacttctc cgttaaccag atgatcaaca aagaagcggt taagcagcgt    480

ctcaaccgtg aagatcaggg gatttcgttc actgagtttt cctacaacct gttgcagggt    540

tatggtttcg catgtgctaa caaacagtac ggtgtggtgc tgcaaattgg tggttctgac    600

cagtggggta acatcacttc tggtatcgac ctgacccgtc gtctgcatca gaatcaggtg    660

tttggcctga ccgttccgct gatcactaaa gcagatggca ccaaatttgg taaaactgaa    720

ggcggcgcag tctggttaga tccgaagaaa accagcccgt acaaattcta ccagttctgg    780

atcaacactg cgcgtgccga cgtttaccgc ttcctgaagt tcttcacctt tatgagcatt    840

gaagagatca acgccctgga agaagaagat aaaaacagcg gtaaagcacc gcgcgcccag    900

tatgtactgg cggagcaggt gactcgtctg gttcacggtg aagaaggttt acaggcggca    960

aaacgtatta ccgaatgcct gttcagcggt tctttgagtg cgctgagtga agcggacttc   1020

gaacagctgg cgcaggacgg cgtaccgatg gttgagatgg aaaagggcgc agacctgatg   1080

caggcactgg tcgattctga actgcaacct tcccgtggtc aggcacgtaa aactatcgcc   1140

tccaatgcca tcaccattaa cggtgaaaaa cagtccgatc ctgaatactt ctttaaagaa   1200

gaagatcgtc tgtttggtcg ttttacctta ctgcgtcgcg gtaaaaagaa ttactgtctg   1260

atttgctgga aataa                                                    1275
```

<210> SEQ ID NO 39
<211> LENGTH: 1269
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 39

```
atggcaagca gtaacttgat taaacaattg caagagcggg ggctggtagc ccaggtgacg     60

gacgaggaag cgttagcaga gcgactggcg caaggcccga tcgcgctcgg gtgcggcttc    120

gatcctaccg ctgacagctt gcatttgggg catcttgttc cattgttatg cctgaaacgc    180

ttccagcagg cgggtcaccg tccgatcgcg ctggttggtg gtgcgaccgg tctgattggc    240

gacccgagcg gcaagaaaag cgagcgtacc ctgaacgcga aggaaaccgt tgaagcgtgg    300

agcgcgcgta tcaaagaaca gctgggtcgt ttcctggact ttgaggcgga tggcaacccg    360

gcgaagatta aaaacaacta tgactggatc ggtccgctgg atgtgattac cttcctgcgt    420
```

```
gatgtgggca agcactttag cgttaactac atgatggcga aagagagcgt tcagagccgt     480

atcgaaaccg gtattagctt caccgagttt agctacatga tgctgcaagc gtatggtttc     540

ctgcgtgcct acgaaaccga aggctgccgt ctgcagatcg gtggcagcga tcaatggggt     600

aacatcaccg cgggcctgga actgattcgt aagaccaaag gtgaagcgcg tgcgtttggc     660

ctgaccatcc cgctggtgac caaggcggac ggtaccaagt ttggcaaaac cgaaagcggt     720

accatttggc tggataagga gaaaaccagc ccgtacgaat tctatcagtt ttggatcaac     780

accgacgatc gtgacgttat tcgttacctg aagtatttca cctttctgag caaagaggaa     840

atcgaagcgc tggagcagga actgcgtgag gcgccggaaa agcgtgcggc gcaaaaagcg     900

ctggcggagg aagtgaccaa actggttcac ggtgaggaag cgctgcgtca ggcgatccgt     960

attagcgaag cgctgtttag cggtgatatc gcgaacctga ccgcggcgga gattgaacaa    1020

ggcttcaagg acgtgccgag ctttgttcac gaaggtggcg atgtgccgct ggttgagctg    1080

ctggttagcg cgggtatcag cccgagcaaa cgtcaggcgc gtgaagacat ccaaaacggt    1140

gcgatttacg tgaacggcga gcgtctgcaa gatgttggcg cgattctgac cgcggaacac    1200

cgtctggaag gtcgttttac cgttatccgt cgtggcaaga agaaatacta tctgattcgt    1260

tatgcgtaa                                                            1269
```

```
<210> SEQ ID NO 40
<211> LENGTH: 1275
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40

atggcaagca gtaacttgat taaacaattg caagagcggg ggctggtagc ccaggtgacg      60

gacgaggaag cgttagcaga gcgactggcg caaggcccga tcgcgctcgg gtgcggcttc     120

gatcctaccg ctgacagctt gcatttgggg catcttgttc cattgttatg cctgaaacgc     180

ttccagcagg cgggccacaa gccggttgcg ctggtaggcg gcgcgacggg tctgattggc     240

gacccgagtt tcaaagctgc cgagcgtaag ctgaacaccg aagaaactgt tcaggagtgg     300

gtggacaaaa tccgtaagca ggttgccccg ttcctcgatt tcgactgtgg agaaaactct     360

gctatcgcgg cgaacaacta tgactggttc ggcaatatga atgtgctgac cttcctgcgc     420

gatattggca aacacttctc cgttaaccag atgatcaaca aagaagcggt taagcagcgt     480

ctcaaccgtg aagatcaggg gatttcgttc actgagtttt cctacagcct gttgcagggt     540

tatgggttcg cctgtgctaa caaacagtac ggtgtggtgc tgcaaattgg tggttctgac     600

cagtggggta acatcacttc tggtatcgac ctgacccgtc gtctgcatca gaatcaggtg     660

tttggcctga ccgttccgct gatcactaaa gcagatggca ccaaatttgg caaaaccgaa     720

agcggtacca tttggctgga taaggagaaa accagcccgt acgaattcta tcagttttgg     780

atcaacaccg acgatcgtga cgttattcgt tacctgaagt atttcacctt tctgagcaaa     840

gaggaaatcg aagcgctgga gcaggaactg cgtgaggcgc cggaaaagcg tgcggcgcaa     900

aaagcgctgg cggaggaagt gaccaaactg gttcacggtg aggaagcgct gcgtcaggcg     960

atccgtatta gcgaagcgct gtttagcggt gatatcgcga acctgaccgc ggcggagatt    1020

gaacaaggct tcaaggacgt gccgagcttt gttcacgaag gtggcgatgt gccgctggtt    1080

gagctgctgg ttagcgcggg tatcagcccg agcaaacgtc aggcgcgtga agacatccaa    1140
```

```
aacggtgcga tttacgtgaa cggcgagcgt ctgcaagatg ttggcgcgat tctgaccgcg   1200

gaacaccgtc tggaaggtcg ttttaccgtt atccgtcgtg gcaagaagaa atactatctg   1260

attcgttatg cgtaa                                                    1275


<210> SEQ ID NO 41
<211> LENGTH: 1269
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41

atggcaagca gtaacttgat taaacaattg caagagcggg ggctggtagc ccaggtgacg     60

gacgaggaag cgttagcaga gcgactggcg caaggcccga tcgcgctcta ttgcggcttc    120

gatcctaccg ctgacagctt gcatttgggg catcttgttc cattgttatg cctgaaacgc    180

ttccagcagg cgggtcaccg tccgatcgcg ctggttggtg gtgcgaccgg tctgattggc    240

gacccgagcg gcaagaaaag cgagcgtacc ctgaacgcga aggaaaccgt tgaagcgtgg    300

agcgcgcgta tcaaagaaca gctgggtcgt ttcctggact ttgaggcgga tggcaacccg    360

gcgaagatta aaaacaacta tgactggatc ggtccgctgg atgtgattac cttcctgcgt    420

gatgtgggca agcactttag cgttaactac atgatggcga aagagagcgt tcagagccgt    480

atcgaaaccg gtattagctt caccgagttt agctacatga tgctgcaagc gtatgacttc    540

ctgcgtctgt acgaaaccga aggctgccgt ctgcagatcg gtggcagcga tcaatggggt    600

aacatcaccg cgggcctgga actgattcgt aagaccaaag gtgaagcgcg tgcgtttggc    660

ctgaccatcc cgctggtgac caaggcggac ggtaccaagt ttggcaaaac cgaaagcggt    720

accatttggc tggataagga gaaaaccagc ccgtacgaat tctatcagtt ttggatcaac    780

accgacgatc gtgacgttat tcgttacctg aagtatttca cctttctgag caaagaggaa    840

atcgaagcgc tggagcagga actgcgtgag gcgccggaaa agcgtgcggc gcaaaaagcg    900

ctggcggagg aagtgaccaa actggttcac ggtgaggaag cgctgcgtca ggcgatccgt    960

attagcgaag cgctgtttag cggtgatatc gcgaacctga ccgcggcgga gattgaacaa   1020

ggcttcaagg acgtgccgag ctttgttcac gaaggtggcg atgtgccgct ggttgagctg   1080

ctggttagcg cgggtatcag cccgagcaaa cgtcaggcgc gtgaagacat ccaaaacggt   1140

gcgatttacg tgaacggcga gcgtctgcaa gatgttggcg cgattctgac cgcggaacac   1200

cgtctggaag gtcgttttac cgttatccgt cgtggcaaga agaaatacta tctgattcgt   1260

tatgcgtaa                                                           1269


<210> SEQ ID NO 42
<211> LENGTH: 422
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
```

```
            20                  25                  30

Pro Ile Ala Leu Tyr Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Arg Pro Ile Ala Leu Val Gly Gly Ala Thr Gly Leu Ile Gly
65                  70                  75                  80

Asp Pro Ser Gly Lys Lys Ser Glu Arg Thr Leu Asn Ala Lys Glu Thr
                85                  90                  95

Val Glu Ala Trp Ser Ala Arg Ile Lys Glu Gln Leu Gly Arg Phe Leu
            100                 105                 110

Asp Phe Glu Ala Asp Gly Asn Pro Ala Lys Ile Lys Asn Asn Tyr Asp
        115                 120                 125

Trp Ile Gly Pro Leu Asp Val Ile Thr Phe Leu Arg Asp Val Gly Lys
    130                 135                 140

His Phe Ser Val Asn Tyr Met Met Ala Lys Glu Ser Val Gln Ser Arg
145                 150                 155                 160

Ile Glu Thr Gly Ile Ser Phe Thr Glu Phe Ser Tyr Met Met Leu Gln
                165                 170                 175

Ala Tyr Asp Phe Leu Arg Leu Tyr Glu Thr Glu Gly Cys Arg Leu Gln
            180                 185                 190

Ile Gly Gly Ser Asp Gln Trp Gly Asn Ile Thr Ala Gly Leu Glu Leu
        195                 200                 205

Ile Arg Lys Thr Lys Gly Glu Ala Arg Ala Phe Gly Leu Thr Ile Pro
    210                 215                 220

Leu Val Thr Lys Ala Asp Gly Thr Lys Phe Gly Lys Thr Glu Ser Gly
225                 230                 235                 240

Thr Ile Trp Leu Asp Lys Glu Lys Thr Ser Pro Tyr Glu Phe Tyr Gln
                245                 250                 255

Phe Trp Ile Asn Thr Asp Asp Arg Asp Val Ile Arg Tyr Leu Lys Tyr
            260                 265                 270

Phe Thr Phe Leu Ser Lys Glu Glu Ile Glu Ala Leu Glu Gln Glu Leu
        275                 280                 285

Arg Glu Ala Pro Glu Lys Arg Ala Ala Gln Lys Ala Leu Ala Glu Glu
    290                 295                 300

Val Thr Lys Leu Val His Gly Glu Glu Ala Leu Arg Gln Ala Ile Arg
305                 310                 315                 320

Ile Ser Glu Ala Leu Phe Ser Gly Asp Ile Ala Asn Leu Thr Ala Ala
                325                 330                 335

Glu Ile Glu Gln Gly Phe Lys Asp Val Pro Ser Phe Val His Glu Gly
            340                 345                 350

Gly Asp Val Pro Leu Val Glu Leu Leu Val Ser Ala Gly Ile Ser Pro
        355                 360                 365

Ser Lys Arg Gln Ala Arg Glu Asp Ile Gln Asn Gly Ala Ile Tyr Val
    370                 375                 380

Asn Gly Glu Arg Leu Gln Asp Val Gly Ala Ile Leu Thr Ala Glu His
385                 390                 395                 400

Arg Leu Glu Gly Arg Phe Thr Val Ile Arg Arg Gly Lys Lys Lys Tyr
                405                 410                 415

Tyr Leu Ile Arg Tyr Ala
            420
```

<210> SEQ ID NO 43

<211> LENGTH: 422
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Gly Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Arg Pro Ile Ala Leu Val Gly Gly Ala Thr Gly Leu Ile Gly
65                  70                  75                  80

Asp Pro Ser Gly Lys Lys Ser Glu Arg Thr Leu Asn Ala Lys Glu Thr
                85                  90                  95

Val Glu Ala Trp Ser Ala Arg Ile Lys Glu Gln Leu Gly Arg Phe Leu
            100                 105                 110

Asp Phe Glu Ala Asp Gly Asn Pro Ala Lys Ile Lys Asn Asn Tyr Asp
        115                 120                 125

Trp Ile Gly Pro Leu Asp Val Ile Thr Phe Leu Arg Asp Val Gly Lys
    130                 135                 140

His Phe Ser Val Asn Tyr Met Met Ala Lys Glu Ser Val Gln Ser Arg
145                 150                 155                 160

Ile Glu Thr Gly Ile Ser Phe Thr Glu Phe Ser Tyr Met Met Leu Gln
                165                 170                 175

Ala Tyr Gly Phe Leu Arg Ala Tyr Glu Thr Glu Gly Cys Arg Leu Gln
            180                 185                 190

Ile Gly Gly Ser Asp Gln Trp Gly Asn Ile Thr Ala Gly Leu Glu Leu
        195                 200                 205

Ile Arg Lys Thr Lys Gly Glu Ala Arg Ala Phe Gly Leu Thr Ile Pro
    210                 215                 220

Leu Val Thr Lys Ala Asp Gly Thr Lys Phe Gly Lys Thr Glu Ser Gly
225                 230                 235                 240

Thr Ile Trp Leu Asp Lys Glu Lys Thr Ser Pro Tyr Glu Phe Tyr Gln
                245                 250                 255

Phe Trp Ile Asn Thr Asp Asp Arg Asp Val Ile Arg Tyr Leu Lys Tyr
            260                 265                 270

Phe Thr Phe Leu Ser Lys Glu Glu Ile Glu Ala Leu Glu Gln Glu Leu
        275                 280                 285

Arg Glu Ala Pro Glu Lys Arg Ala Ala Gln Lys Ala Leu Ala Glu Glu
    290                 295                 300

Val Thr Lys Leu Val His Gly Glu Glu Ala Leu Arg Gln Ala Ile Arg
305                 310                 315                 320

Ile Ser Glu Ala Leu Phe Ser Gly Asp Ile Ala Asn Leu Thr Ala Ala
                325                 330                 335

Glu Ile Glu Gln Gly Phe Lys Asp Val Pro Ser Phe Val His Glu Gly
            340                 345                 350

Gly Asp Val Pro Leu Val Glu Leu Leu Val Ser Ala Gly Ile Ser Pro
        355                 360                 365
```

```
Ser Lys Arg Gln Ala Arg Glu Asp Ile Gln Asn Gly Ala Ile Tyr Val
    370                 375                 380

Asn Gly Glu Arg Leu Gln Asp Val Gly Ala Ile Leu Thr Ala Glu His
385                 390                 395                 400

Arg Leu Glu Gly Arg Phe Thr Val Ile Arg Arg Gly Lys Lys Lys Tyr
                405                 410                 415

Tyr Leu Ile Arg Tyr Ala
            420


<210> SEQ ID NO 44
<211> LENGTH: 422
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Val Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Arg Pro Ile Ala Leu Val Gly Gly Ala Thr Gly Leu Ile Gly
65                  70                  75                  80

Asp Pro Ser Gly Lys Lys Ser Glu Arg Thr Leu Asn Ala Lys Glu Thr
                85                  90                  95

Val Glu Ala Trp Ser Ala Arg Ile Lys Glu Gln Leu Gly Arg Phe Leu
            100                 105                 110

Asp Phe Glu Ala Asp Gly Asn Pro Ala Lys Ile Lys Asn Asn Tyr Asp
        115                 120                 125

Trp Ile Gly Pro Leu Asp Val Ile Thr Phe Leu Arg Asp Val Gly Lys
    130                 135                 140

His Phe Ser Val Asn Tyr Met Met Ala Lys Glu Ser Val Gln Ser Arg
145                 150                 155                 160

Ile Glu Thr Gly Ile Ser Phe Thr Glu Phe Ser Tyr Met Met Leu Gln
                165                 170                 175

Ala Tyr Ser Met Leu Arg Ala Tyr Glu Thr Glu Gly Cys Arg Leu Gln
            180                 185                 190

Ile Gly Gly Ser Asp Gln Trp Gly Asn Ile Thr Ala Gly Leu Glu Leu
        195                 200                 205

Ile Arg Lys Thr Lys Gly Glu Ala Arg Ala Phe Gly Leu Thr Ile Pro
    210                 215                 220

Leu Val Thr Lys Ala Asp Gly Thr Lys Phe Gly Lys Thr Glu Ser Gly
225                 230                 235                 240

Thr Ile Trp Leu Asp Lys Glu Lys Thr Ser Pro Tyr Glu Phe Tyr Gln
                245                 250                 255

Phe Trp Ile Asn Thr Asp Asp Arg Asp Val Ile Arg Tyr Leu Lys Tyr
            260                 265                 270

Phe Thr Phe Leu Ser Lys Glu Glu Ile Glu Ala Leu Glu Gln Glu Leu
        275                 280                 285

Arg Glu Ala Pro Glu Lys Arg Ala Ala Gln Lys Ala Leu Ala Glu Glu
```

```
    290                 295                 300

Val Thr Lys Leu Val His Gly Glu Glu Ala Leu Arg Gln Ala Ile Arg
305                 310                 315                 320

Ile Ser Glu Ala Leu Phe Ser Gly Asp Ile Ala Asn Leu Thr Ala Ala
                325                 330                 335

Glu Ile Glu Gln Gly Phe Lys Asp Val Pro Ser Phe Val His Glu Gly
            340                 345                 350

Gly Asp Val Pro Leu Val Glu Leu Leu Val Ser Ala Gly Ile Ser Pro
        355                 360                 365

Ser Lys Arg Gln Ala Arg Glu Asp Ile Gln Asn Gly Ala Ile Tyr Val
    370                 375                 380

Asn Gly Glu Arg Leu Gln Asp Val Gly Ala Ile Leu Thr Ala Glu His
385                 390                 395                 400

Arg Leu Glu Gly Arg Phe Thr Val Ile Arg Arg Gly Lys Lys Lys Tyr
                405                 410                 415

Tyr Leu Ile Arg Tyr Ala
            420
```

<210> SEQ ID NO 45
<211> LENGTH: 1275
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 45

```
atggcaagca gtaacttgat taaacaattg caagagcggg ggctggtagc ccaggtgacg     60

gacgaggaag cgttagcaga gcgactggcg caaggcccga tcgcgctcta ttgcggcttc    120

gatcctaccg ctgacagctt gcatttgggg catcttgttc cattgttatg cctgaaacgc    180

ttccagcagg cgggccacaa gccggttgcg ctggtaggcg gcgcgacggg tctgattggc    240

gacccgagct tcaaagctgc cgagcgtaag ctgaacaccg aagaaactgt tcaggagtgg    300

gtggacaaaa tccgtaagca ggttgccccg ttcctcgatt tcgactgtgg agaaaactct    360

gctatcgcgg cgaacaacta tgactggttc ggcaatatga atgtgctgac cttcctgcgc    420

gatattggca aacacttctc cgttaaccag atgatcaaca aagaagcggt taagcagcgt    480

ctcaaccgtg aagatcaggg gatttcgttc actgagtttt cctacagcct gttgcagggt    540

tatgacttcg cctgtctgaa caaacagtac ggtgtggtgc tgcaaattgg tggttctgac    600

cagtggggta acatcacttc tggtatcgac ctgacccgtc gtctgcatca gaatcaggtg    660

tttggcctga ccgttccgct gatcactaaa gcagatggca ccaaatttgg caaaaccgaa    720

agcggtacca tttggctgga taaggagaaa accagcccgt acgaattcta tcagttttgg    780

atcaacaccg acgatcgtga cgttattcgt tacctgaagt atttcacctt tctgagcaaa    840

gaggaaatcg aagcgctgga gcaggaactg cgtgaggcgc cggaaaagcg tgcggcgcaa    900

aaagcgctgg cggaggaagt gaccaaactg gttcacggtg aggaagcgct gcgtcaggcg    960

atccgtatta gcgaagcgct gtttagcggt gatatcgcga acctgaccgc ggcggagatt   1020

gaacaaggct tcaaggacgt gccgagcttt gttcacgaag gtggcgatgt gccgctggtt   1080

gagctgctgg ttagcgcggg tatcagcccg agcaaacgtc aggcgcgtga agacatccaa   1140

aacggtgcga tttacgtgaa cggcgagcgt ctgcaagatg ttggcgcgat tctgaccgcg   1200

gaacaccgtc tggaaggtcg ttttaccgtt atccgtcgtg gcaagaagaa atactatctg   1260
```

attcgttatg cgtaa 1275

<210> SEQ ID NO 46
<211> LENGTH: 424
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Tyr Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Ser
                165                 170                 175

Leu Leu Gln Gly Tyr Asp Phe Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Ser Gly Thr Ile Trp Leu Asp Lys Glu Lys Thr Ser Pro Tyr Glu Phe
                245                 250                 255

Tyr Gln Phe Trp Ile Asn Thr Asp Asp Arg Asp Val Ile Arg Tyr Leu
            260                 265                 270

Lys Tyr Phe Thr Phe Leu Ser Lys Glu Glu Ile Glu Ala Leu Glu Gln
        275                 280                 285

Glu Leu Arg Glu Ala Pro Glu Lys Arg Ala Ala Gln Lys Ala Leu Ala
    290                 295                 300

Glu Glu Val Thr Lys Leu Val His Gly Glu Glu Ala Leu Arg Gln Ala
305                 310                 315                 320

Ile Arg Ile Ser Glu Ala Leu Phe Ser Gly Asp Ile Ala Asn Leu Thr
                325                 330                 335

Ala Ala Glu Ile Glu Gln Gly Phe Lys Asp Val Pro Ser Phe Val His
```

```
            340                 345                 350

Glu Gly Gly Asp Val Pro Leu Val Glu Leu Leu Val Ser Ala Gly Ile
        355                 360                 365

Ser Pro Ser Lys Arg Gln Ala Arg Glu Asp Ile Gln Asn Gly Ala Ile
    370                 375                 380

Tyr Val Asn Gly Glu Arg Leu Gln Asp Val Gly Ala Ile Leu Thr Ala
385                 390                 395                 400

Glu His Arg Leu Glu Gly Arg Phe Thr Val Ile Arg Arg Gly Lys Lys
                405                 410                 415

Lys Tyr Tyr Leu Ile Arg Tyr Ala
            420


<210> SEQ ID NO 47
<211> LENGTH: 424
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Gly Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Ser
                165                 170                 175

Leu Leu Gln Gly Tyr Gly Phe Ala Cys Ala Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Ser Gly Thr Ile Trp Leu Asp Lys Glu Lys Thr Ser Pro Tyr Glu Phe
                245                 250                 255

Tyr Gln Phe Trp Ile Asn Thr Asp Asp Arg Asp Val Ile Arg Tyr Leu
            260                 265                 270
```

-continued

```
Lys Tyr Phe Thr Phe Leu Ser Lys Glu Glu Ile Glu Ala Leu Glu Gln
        275                 280                 285

Glu Leu Arg Glu Ala Pro Glu Lys Arg Ala Ala Gln Lys Ala Leu Ala
    290                 295                 300

Glu Glu Val Thr Lys Leu Val His Gly Glu Glu Ala Leu Arg Gln Ala
305                 310                 315                 320

Ile Arg Ile Ser Glu Ala Leu Phe Ser Gly Asp Ile Ala Asn Leu Thr
                325                 330                 335

Ala Ala Glu Ile Glu Gln Gly Phe Lys Asp Val Pro Ser Phe Val His
            340                 345                 350

Glu Gly Gly Asp Val Pro Leu Val Glu Leu Leu Val Ser Ala Gly Ile
        355                 360                 365

Ser Pro Ser Lys Arg Gln Ala Arg Glu Asp Ile Gln Asn Gly Ala Ile
    370                 375                 380

Tyr Val Asn Gly Glu Arg Leu Gln Asp Val Gly Ala Ile Leu Thr Ala
385                 390                 395                 400

Glu His Arg Leu Glu Gly Arg Phe Thr Val Ile Arg Arg Gly Lys Lys
                405                 410                 415

Lys Tyr Tyr Leu Ile Arg Tyr Ala
            420
```